(12) United States Patent
Kahvejian et al.

(10) Patent No.: US 11,274,158 B2
(45) Date of Patent: Mar. 15, 2022

(54) METHODS AND COMPOSITIONS FOR TREATING INFLAMMATORY OR AUTOIMMUNE DISEASES OR CONDITIONS USING CALCITONIN RECEPTOR ACTIVATORS

(71) Applicant: Flagship Pioneering Innovations V, Inc., Cambridge, MA (US)

(72) Inventors: Avak Kahvejian, Lexington, MA (US); Jordi Mata-Fink, Baltimore, MD (US); Jonathan Barry Hurov, Bedford, MA (US); Chengyi Jenny Shu, Cambridge, MA (US); George Huck Neubauer, Malden, MA (US); Manuel Andreas Fankhauser, Bern (CH); Julian Alexander Stanley, Oregon City, OR (US)

(73) Assignee: Flagship Pioneering Innovations V, Inc., Cambridge, MA (US)

( * ) Notice: Subject to any disclaimer, the term of this patent is extended or adjusted under 35 U.S.C. 154(b) by 0 days.

(21) Appl. No.: 16/140,224

(22) Filed: Sep. 24, 2018

(65) Prior Publication Data
US 2019/0233527 A1 Aug. 1, 2019

Related U.S. Application Data

(60) Provisional application No. 62/623,885, filed on Jan. 30, 2018.

(51) Int. Cl.
*C07K 16/28* (2006.01)
*A61P 1/00* (2006.01)

(52) U.S. Cl.
CPC ............ *C07K 16/2869* (2013.01); *A61P 1/00* (2018.01); *C07K 2317/54* (2013.01); *C07K 2317/565* (2013.01); *C07K 2317/72* (2013.01); *C07K 2317/75* (2013.01); *C07K 2319/30* (2013.01)

(58) Field of Classification Search
CPC ................................. C07K 16/2869; A61P 1/00
See application file for complete search history.

(56) References Cited

U.S. PATENT DOCUMENTS

| | | | |
|---|---|---|---|
| 5,858,978 A | 1/1999 | Vignery | |
| 7,396,936 B1 | 7/2008 | Pryor et al. | |
| 8,617,550 B2 | 12/2013 | Nishimoto et al. | |
| 9,593,149 B2 | 3/2017 | Kruse et al. | |
| 2002/0010133 A1* | 1/2002 | Young | A61K 38/22 514/1.1 |
| 2002/0037846 A1* | 3/2002 | Cadieux | A61K 38/23 514/11.9 |
| 2006/0189532 A1* | 8/2006 | DeLuca | A61K 31/593 514/11.9 |
| 2006/0194722 A1* | 8/2006 | Azria | A61K 9/0031 514/11.9 |
| 2007/0105774 A1* | 5/2007 | DeLuca | A61K 31/59 514/11.9 |
| 2008/0207501 A1* | 8/2008 | Erickson | C07K 14/575 514/6.9 |
| 2008/0226737 A1* | 9/2008 | Azria | A61K 31/609 424/489 |
| 2010/0204116 A1* | 8/2010 | Bevec | A61K 38/23 514/6.9 |
| 2010/0204117 A1* | 8/2010 | Bevec | A61K 38/22 514/1.1 |
| 2010/0278881 A1* | 11/2010 | Azria | A61K 9/0031 424/400 |
| 2012/0071410 A1* | 3/2012 | Mehta | A61K 38/23 514/11.9 |
| 2012/0219603 A1* | 8/2012 | Azria | A61K 31/609 424/400 |
| 2012/0294797 A1* | 11/2012 | Kovacevich | C07K 16/26 424/1.11 |
| 2013/0295088 A1* | 11/2013 | Poulsen | C07K 16/18 424/133.1 |
| 2014/0249085 A1* | 9/2014 | Mehta | A61K 38/23 514/11.9 |
| 2014/0271735 A1* | 9/2014 | Azria | A61K 9/0031 424/400 |
| 2016/0317623 A1* | 11/2016 | Shen | A61K 9/0019 |
| 2016/0339082 A1* | 11/2016 | Mehta | A61K 38/23 |
| 2017/0106068 A1* | 4/2017 | Bourinbaiar | A61K 39/001144 |

FOREIGN PATENT DOCUMENTS

| WO | WO-2005/025504 A2 | 3/2005 |
|---|---|---|
| WO | WO-2018/022664 A1 | 2/2018 |
| WO | WO-2018/211111 A1 | 11/2018 |

OTHER PUBLICATIONS

Kiriyama et al., 2001, Calcitonin Induces IL-6 Production via Both PKA and PKC Pathways in the Pituitary Folliculo-Stellate Cell Line, Endocrinology, 142(8): 3563-3569.*
Abdel-Magied et al., "Serum interleukin-6 in systemic sclerosis and its correlation with disease parameters and cardiopulmonary involvement," Sarcoidosis Vasc Diffuse Lung Dis. 33(4):321-330 (2016).
Alloca et al., "Anti-IL-6 treatment for inflammatory bowel diseases: next cytokine, next target," Curr Drug Targets. 14(12):1508-21 (2013).

(Continued)

*Primary Examiner* — Amber D Steele
(74) *Attorney, Agent, or Firm* — Clark & Elbing LLP

(57) ABSTRACT

The present invention provides methods for treating inflammatory or autoimmune disease using calcitonin receptor activators, such as calcitonin receptor activating antibodies, among others. The invention also features compositions containing calcitonin receptor activators, methods of diagnosing patients with calcitonin receptor-associated inflammatory or autoimmune disease, and methods of predicting the response of an inflammatory or autoimmune disease or condition in a subject to treatment with calcitonin receptor activators.

10 Claims, No Drawings
Specification includes a Sequence Listing.

(56) References Cited

OTHER PUBLICATIONS

Aricha et al., "Blocking of IL-6 suppresses experimental autoimmune myasthenia gravis," J Autoimmun. 36(2):135-41 (2011).
Atreya et al., "Involvement of IL-6 in the pathogenesis of inflammatory bowel disease and colon cancer," Clin Rev Allergy Immunol. 28(3):187-96 (2005).
Boras et al., "The significance of salivary and serum interleukin 6 and basic fibroblast growth factor levels in patients with Sjögren's syndrome," Coll Antropol. 28(Suppl. 2): 305-309 (2004) (6 pages).
Chu et al., "Therapeutic potential of anti-IL-6 therapies for granulocytic airway inflammation in asthma," Allergy Asthma Clin Immunol. 11(1):14 (2015) (6 pages).
Fielding et al., "Interleukin-6 signaling drives fibrosis in unresolved inflammation," Immunity. 40(1):40-50 (2014).
Grossman et al., "Interleukin 6 is expressed in high levels in psoriatic skin and stimulates proliferation of cultured human keratinocytes," Proc Natl Acad Sci U S A. 86(16):6367-71 (1989).
Hundhausen et al., "Enhanced T cell responses to IL-6 in type 1 diabetes are associated with early clinical disease and increased IL-6 receptor expression," Sci Transl Med. 8(356):356ra119 (2016) (26 pages).
Ito, "Anti-interleukin-6 therapy for Crohn's disease," Curr Pharm Des. 9(4):295-305 (2003).
Le et al., "Blockade of IL-6 trans signaling attenuates pulmonary fibrosis," J Immunol. 193(7):3755-68 (2014).
Maurer et al., "IL-6 and Akt are involved in muscular pathogenesis in myasthenia gravis," Acta Neuropathol Commun. 3:1 (2015) (14 pages).
O'Reilly et al., "Interleukin-6: a new therapeutic target in systemic sclerosis?," Clin Transl Immunology. 2(4):e4 (2013) (6 pages).
Rincon et al., "Role of IL-6 in asthma and other inflammatory pulmonary diseases," Int J Biol Sci. 8(9):1281-90 (2012).
Ripley et al., "Raised levels of interleukin 6 in systemic lupus erythematosus correlate with anaemia," Ann Rheum Dis. 64(6):849-53 (2005).
Roescher et al., "Cytokines in Sjögren's syndrome: potential therapeutic targets," available in PMC Feb. 24, 2011, published in final edited form as: Ann Rheum Dis. 69(6):945-8 (2010).
Saggini et al., "IL-6 as a druggable target in psoriasis: focus on pustular variants," J Immunol Res. 2014:964069 (2014) (10 pages).
Serada et al., "IL-6 blockade inhibits the induction of myelin antigen-specific Th17 cells and Th1 cells in experimental autoimmune encephalomyelitis," Proc Natl Acad Sci U S A. 105(26):9041-6 (2008).
Srirangan et al., "The role of interleukin 6 in the pathophysiology of rheumatoid arthritis," Ther Adv Musculoskelet Dis. 2(5):247-56 (2010).
Stelmasiak et al., "Interleukin-6 concentration in serum and cerebrospinal fluid in multiple sclerosis patients," Med Sci Monit. 6(6):1104-8 (2000).
Stone et al., "Trial of Tocilizumab in Giant-Cell Arteritis," N Engl J Med. 377(4):317-328 (2017).
Tackey et al., "Rationale for interleukin-6 blockade in systemic lupus erythematosus," available in PMC Oct. 11, 2007, published in final edited form as: Lupus. 13(5):339-43 (2004) (8 pages).
Duan et al., "Calcitonin gene-related peptide exerts anti-inflammatory property through regulating murine macrophages polarization in vitro," Mol Immunol. 91:105-13 (2017).
International Search Report and Written Opinion for International Application No. PCT/US2019/015844, dated Jun. 3, 2019 (13 pages).
Kasashima et al., "Upregulated interleukins (IL-6, IL-10, and IL-13) in immunoglobulin G4-related aortic aneurysm patients," J Vasc Surg. 67(4):1248-1262 (2018).
Kasashima et al., "Inflammatory features, including symptoms, increased serum interleukin-6, and C-reactive protein, in IgG4-related vascular diseases," Heart Vessels. 33(12):1471-1481 (2018).
Perez et al., "Loss of occludin expression and impairment of blood-testis barrier permeability in rats with autoimmune orchitis: effect of interleukin 6 on Sertoli cell tight junctions," Biol Reprod. 87(5):122 (2012) (12 pages).
Rival et al., "Interleukin-6 and IL-6 receptor cell expression in testis of rats with autoimmune orchitis," J Reprod Immunol. 70(1-2):43-58 (2006).
Ulvestad et al., "Acute phase haemolysis in chronic cold agglutinin disease," Scand J Immunol. 54(1-2):239-42 (2001).

* cited by examiner

SEQUENCE LISTING

<160> NUMBER OF SEQ ID NOS: 3

<210> SEQ ID NO 1
<211> LENGTH: 32
<212> TYPE: PRT
<213> ORGANISM: Homo sapiens

<400> SEQUENCE: 1

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 2
<211> LENGTH: 37
<212> TYPE: PRT
<213> ORGANISM: Homo sapiens

<400> SEQUENCE: 2

Ala Cys Asp Thr Ala Thr Cys Val Thr His Arg Leu Ala Gly Leu Leu
1               5                   10                  15

Ser Arg Ser Gly Gly Val Val Lys Asn Asn Phe Val Pro Thr Asn Val
            20                  25                  30

Gly Ser Lys Ala Phe
        35

<210> SEQ ID NO 3
<211> LENGTH: 89
<212> TYPE: PRT
<213> ORGANISM: Homo sapiens

<400> SEQUENCE: 3

Met Gly Ile Leu Lys Leu Gln Val Phe Leu Ile Val Leu Ser Val Ala
1               5                   10                  15

Leu Asn His Leu Lys Ala Thr Pro Ile Glu Ser His Gln Val Glu Lys
            20                  25                  30

Arg Lys Cys Asn Thr Ala Thr Cys Ala Thr Gln Arg Leu Ala Asn Phe
        35                  40                  45

Leu Val His Ser Ser Asn Asn Phe Gly Ala Ile Leu Ser Ser Thr Asn
    50                  55                  60

Val Gly Ser Asn Thr Tyr Gly Lys Arg Asn Ala Val Glu Val Leu Lys
65                  70                  75                  80

Arg Glu Pro Leu Asn Tyr Leu Pro Leu
                85

METHODS AND COMPOSITIONS FOR TREATING INFLAMMATORY OR AUTOIMMUNE DISEASES OR CONDITIONS USING CALCITONIN RECEPTOR ACTIVATORS

BACKGROUND

Epidemiological data provide evidence of a steady rise in inflammatory and autoimmune disease throughout westernized societies over the last decades. The net % increase/year incidence and prevalence of autoimmune diseases worldwide have been reported to be 19% and 12%, respectively (Lerner et al., Intl J Celiac Dis. 3:151, 2015). Thus, there remains a need in the field for treatments of immune conditions such as autoimmune disease.

SUMMARY OF THE INVENTION

The present invention provides methods for treating inflammatory or autoimmune disease using calcitonin receptor activators, such as calcitonin receptor activating antibodies, among others. The invention also features compositions containing calcitonin receptor activators, methods of diagnosing patients with calcitonin receptor-associated inflammatory or autoimmune disease, and methods of predicting the response of an inflammatory or autoimmune disease or condition in a subject to treatment with calcitonin receptor activators.

In a first aspect, the invention provides a method of modulating an immune response in a subject by administering to the subject an effective amount of a calcitonin receptor activator.

In another aspect, the invention provides a method of modulating an immune response in a subject by contacting an immune cell, spleen, lymph node, secondary lymphoid organ, tertiary lymphoid organ, barrier tissue, skin, gut, airway, or a wound with an effective amount of a calcitonin receptor activator.

In another aspect, the invention provides a method of modulating an immune cell activity by contacting an immune cell, spleen, lymph node, secondary lymphoid organ, tertiary lymphoid organ, barrier tissue, skin, gut, airway, or wound with an effective amount of a calcitonin receptor activator.

In another aspect, the invention provides a method of treating a subject with an inflammatory or autoimmune disease or condition by administering to the subject an effective amount of a calcitonin receptor activator.

In another aspect, the invention provides a method of treating a subject with an inflammatory or autoimmune disease or condition by contacting an immune cell, spleen, lymph node, secondary lymphoid organ, tertiary lymphoid organ, barrier tissue, skin, gut, airway, or wound with an effective amount of a calcitonin receptor activator.

In another aspect, the invention provides a method of treating a subject identified as having an inflammatory or autoimmune disease or condition by administering to the subject an effective amount of a calcitonin receptor activator.

In another aspect, the invention provides a method of treating a subject identified as having an inflammatory or autoimmune disease or condition by contacting an immune cell, spleen, lymph node, secondary lymphoid organ, tertiary lymphoid organ, barrier tissue, skin, gut, airway, or wound with an effective amount of a calcitonin receptor activator.

In another aspect, the invention provides a method of decreasing levels of one or more pro-inflammatory cytokine in a subject in need thereof by administering to the subject an effective amount of a calcitonin receptor activator. In some embodiments, the subject is a subject with a calcitonin receptor-associated inflammatory or autoimmune disease or condition. In some embodiments, the one or more pro-inflammatory cytokine includes interleukin-6 (IL-6) and/or interferon gamma (IFNγ). In some embodiments, the method further includes determining the level of one or more pro-inflammatory cytokine after administration of the calcitonin receptor activator.

In some embodiments of any of the foregoing aspects, the inflammatory or autoimmune disease or condition is a calcitonin receptor-associated inflammatory or autoimmune disease or condition.

In another aspect, the invention provides a method of treating a subject with an inflammatory or autoimmune disease or condition by: a) identifying a subject with calcitonin receptor-associated inflammatory or autoimmune disease or condition; and b) administering to the subject an effective amount of a calcitonin receptor activator.

In another aspect, the invention provides a method of treating a subject with an inflammatory or autoimmune disease or condition by: a) identifying a subject with calcitonin receptor-associated associated inflammatory or autoimmune disease or condition; and b) contacting an immune cell, spleen, lymph node, secondary lymphoid organ, tertiary lymphoid organ, barrier tissue, skin, gut, airway, or wound with an effective amount of a calcitonin receptor activator.

In another aspect, the invention provides a method of treating a subject with a calcitonin receptor-associated associated inflammatory or autoimmune disease or condition by administering to the subject an effective amount of a calcitonin receptor activator.

In another aspect, the invention provides a method of treating a subject identified as having a calcitonin receptor-associated associated inflammatory or autoimmune disease or condition by administering to the subject an effective amount of a calcitonin receptor activator.

In another aspect, the invention provides a method of treating a subject with a calcitonin receptor-associated inflammatory or autoimmune disease or condition by contacting an immune cell, spleen, lymph node, secondary lymphoid organ, tertiary lymphoid organ, barrier tissue, skin, gut, airway, or wound with an effective amount of a calcitonin receptor activator.

In another aspect, the invention provides a method of treating a subject with ulcerative colitis by administering to the subject an effective amount of a calcitonin receptor activator. In some embodiments, the ulcerative colitis is calcitonin receptor-associated ulcerative colitis (e.g., ulcerative colitis associated with expression of a calcitonin receptor (e.g., calcitonin receptor (CALCR) and/or receptor activating modifying protein 1 (RAMP1)) in immune cells).

In some aspects of any of the foregoing embodiments, the method includes contacting an immune cell with an effective amount of a calcitonin receptor activator. In some aspects of any of the foregoing embodiments, the method includes contacting the spleen with an effective amount of a calcitonin receptor activator. In some aspects of any of the foregoing embodiments, the method includes contacting a lymph node with an effective amount of a calcitonin receptor activator. In some aspects of any of the foregoing embodiments, the method includes contacting a secondary lymphoid organ with an effective amount of a calcitonin receptor activator. In some aspects of any of the foregoing embodiments, the method includes contacting a tertiary lymphoid organ with an effective amount of a calcitonin receptor activator. In some aspects of any of the foregoing embodiments, the method includes contacting a barrier tissue with an effective amount of a calcitonin receptor activator. In some aspects of any of the foregoing embodiments, the method includes contacting the skin with an effective amount of a calcitonin receptor activator. In some aspects of any of the foregoing embodiments, the method includes contacting the gut with an effective amount of a calcitonin receptor activator. In some aspects of any of the foregoing embodiments, the method includes contacting an airway with an effective amount of a calcitonin receptor activator. In some aspects of any of the foregoing embodiments, the method includes contacting a wound with an effective amount of a calcitonin receptor activator.

In some embodiments of any of the foregoing aspects, the calcitonin receptor-associated inflammatory or autoimmune disease or condition is associated with expression of a calcitonin receptor (e.g., calcitonin receptor (CALCR) and/or receptor activating modifying protein 1 (RAMP1)) in immune cells. In some embodiments of any of the foregoing aspects, the calcitonin receptor-associated inflammatory or autoimmune disease or condition is associated with decreased expression of a calcitonin receptor (e.g., calcitonin receptor (CALCR) and/or receptor activating modifying protein 1 (RAMP1)) in immune cells.

In some embodiments of any of the foregoing aspects, the method includes contacting an immune cell with an effective amount of a calcitonin receptor activator that increases expression or activity of a calcitonin receptor.

In some embodiments of any of the foregoing aspects, the method includes modulating an immune cell activity.

In some embodiments of any of the foregoing aspects, the immune cell activity is migration, proliferation, recruitment, lymph node homing, lymph node egress, differentiation, activation, polarization, cytokine production, degranulation, maturation, antibody-dependent cell-mediated cytotoxicity (ADCC), antibody-dependent cellular phagocytosis (ADCP), antigen presentation, or calcitonin receptor expression (e.g., expression of CALCR and/or RAMP1).

In some embodiments, lymph node homing and/or calcitonin receptor expression (e.g., expression of CALCR and/or RAMP1) is increased. In some embodiments, the migration, proliferation, recruitment, lymph node egress, differentiation, activation, polarization, cytokine production, degranulation, maturation, ADCC, ADCP, and/or antigen presentation is decreased. In some embodiments, the migration or recruitment toward a site of inflammation is decreased.

In another aspect, the invention provides a method of modulating macrophage cytokine production, by contacting a macrophage with an effective amount of a calcitonin receptor activator.

In another aspect, the invention provides a method of decreasing macrophage production of one or more pro-inflammatory cytokine by contacting a macrophage with an effective amount of a calcitonin receptor activator. In some embodiments, the macrophage is a macrophage expressing a calcitonin receptor (e.g., CALCR and/or RAMP1). In some embodiments, the one or more pro-inflammatory cytokine includes IL-6 and/or IFNγ.

In another aspect, the invention provides a method of modulating macrophage cytokine production in a subject by administering to the subject an effective amount of a calcitonin receptor activator. In some embodiments of any of the foregoing aspects, the macrophage cytokine production of pro-inflammatory cytokines is decreased.

In another aspect, the invention provides a method of decreasing pro-inflammatory cytokine levels in a subject by administering to the subject an effective amount of a calcitonin receptor activator. In some embodiments of any of the foregoing methods, the pro-inflammatory cytokine is IL-6 or interferon gamma (IFNγ).

In another aspect, the invention provides a method of modulating macrophage polarization in a subject by administering to the subject an effective amount of a calcitonin receptor activator. In some embodiments, macrophage polarization toward an M1 phenotype is decreased. In some embodiments, macrophage polarization toward an M2 phenotype is increased.

In another aspect, the invention provides a method of predicting the response of an inflammatory or autoimmune disease or condition in a subject to treatment with a calcitonin receptor activator by contacting an immune cell isolated from the subject with a calcitonin receptor activator and evaluating the response of the immune cell. In some embodiments, the evaluating includes assessing immune cell migration, immune cell proliferation, immune cell recruitment, immune cell differentiation, immune cell activation, immune cell polarization, cytokine production, ADCC, ADCP, or immune cell calcitonin receptor expression (e.g., expression of CALCR and/or RAMP1).

In another aspect, the invention provides a method of predicting the response of an inflammatory or autoimmune disease or condition in a subject to treatment with a calcitonin receptor activator, the method including the steps of: a) isolating an immune cell from the subject; b) measuring the expression of a calcitonin receptor (e.g., expression of CALCR and/or RAMP1) in the immune cell; and c) comparing calcitonin receptor expression in the immune cell to a reference, wherein decreased expression of a calcitonin receptor in the immune cell as compared to the reference indicates that the subject will respond to treatment with a calcitonin receptor activator.

In another aspect, the invention provides a method of determining if an immune cell expresses a functional calcitonin receptor by contacting the immune cell with a calcitonin receptor agonist and evaluating cytokine production. In some embodiments, decreased production of pro-inflammatory cytokines (e.g., IFNγ or IL6) indicates that the immune cell expresses a functional calcitonin receptor.

In some embodiments, the method further includes contacting the immune cell with a calcitonin receptor activator.

In another aspect, the invention provides a method of characterizing an inflammatory or autoimmune disease or condition in a subject by: a) isolating an immune cell from the subject; b) measuring the expression of a calcitonin receptor (e.g., expression of CALCR and/or RAMP1) in the immune cell; and c) comparing calcitonin receptor expression in the immune cell to a reference, wherein decreased expression of a calcitonin receptor in the immune cell as compared to the reference indicates that the subject has a calcitonin receptor-associated inflammatory or autoimmune disease or condition.

In another aspect, the invention provides a method of identifying a subject as having a calcitonin receptor-associated inflammatory or autoimmune disease or condition by: a) isolating an immune cell from the subject; b) measuring the expression of a calcitonin receptor (e.g., expression of CALCR and/or RAMP1) in the immune cell; and c) comparing calcitonin receptor expression in the immune cell to a reference, wherein decreased expression of a calcitonin receptor in immune cell as compared to the reference indicates that the subject has a calcitonin receptor-associated inflammatory or autoimmune disease or condition.

In some embodiments, of any of the foregoing aspects, the immune cell is a macrophage.

In some embodiments of any of the foregoing aspects, the method further includes providing a calcitonin receptor activator suitable for administration to the subject. In some embodiments of any of the foregoing aspects, the method further includes administering to the subject an effective amount of a calcitonin receptor activator.

In some embodiments of any of the foregoing aspects, the calcitonin receptor activator is a calcitonin receptor-specific activator (e.g., a CALCR-specific activator, a RAMP1-specific activator, or an AMY1 receptor (CALCR and RAMP1)-specific activator).

In some embodiments of any of the foregoing aspects, the calcitonin receptor activator or calcitonin receptor-specific activator is a calcitonin receptor function activator.

In some embodiments of any of the foregoing aspects, the calcitonin receptor activator or calcitonin receptor-specific activator is a calcitonin receptor activating antibody or an antigen binding fragment thereof. In some embodiments of any of the foregoing aspects, the calcitonin receptor activating antibody is a calcitonin receptor-specific activating antibody (e.g., a CALCR-specific activating antibody, RAMP1-specific activating antibody, or an AMY1 receptor-specific activating antibody). In some embodiments of any of the foregoing aspects, the calcitonin receptor activator or calcitonin receptor-specific activator is a soluble calcitonin receptor binding partner or a fragment thereof (e.g., calcitonin, CGRP neuropeptide, or amylin or a calcitonin-, CGRP neuropeptide-, or amylin-derived sequence that is capable of signaling). In some embodiments, the soluble calcitonin receptor binding partner is fused to an Fc domain of an antibody, fused to albumin or another protein scaffold, PEGylated, or formulated for local injection or depot injection.

In some embodiments of any of the foregoing aspects, the calcitonin receptor activator or calcitonin receptor-specific activator increases calcitonin receptor expression or activity (e.g., expression or activity of CALCR and/or RAMP1).

In some embodiments of any of the foregoing aspects, the calcitonin receptor activator or calcitonin receptor-specific activator increases calcitonin receptor binding to a binding partner (e.g., calcitonin, CGRP, or amylin).

In some embodiments of any of the foregoing aspects, the inflammatory or autoimmune disease or condition is multiple sclerosis (MS), psoriasis, Crohn's disease, inflammatory bowel disease (IBD), ulcerative colitis, dermatitis, asthma, fibrosis, or wound healing. In some embodiments of any of the foregoing aspects, the inflammatory or autoimmune disease or condition is ulcerative colitis. In some embodiments of any of the foregoing aspects, the inflammatory or autoimmune disease or condition is a calcitonin receptor-associated inflammatory or autoimmune disease or condition. In some embodiments, the calcitonin receptor-associated inflammatory or autoimmune disease or condition is associated with expression of a calcitonin receptor (e.g., CALCR and/or RAMP1) in immune cells.

In some embodiments of any of the foregoing aspects, the calcitonin receptor activator or calcitonin receptor-specific activator is administered locally. In some embodiments of any of the foregoing aspects, the calcitonin receptor activator or calcitonin receptor-specific activator is administered to or near a lymph node, the spleen, a secondary lymphoid organ, a tertiary lymphoid organ, barrier tissue, skin, the gut, an airway, or a wound. In some embodiments of any of the foregoing aspects, the calcitonin receptor activator or calcitonin receptor-specific activator is administered to or near a lymph node. In some embodiments of any of the foregoing aspects, the calcitonin receptor activator or calcitonin receptor-specific activator is administered to or near the spleen. In some embodiments of any of the foregoing aspects, the calcitonin receptor activator or calcitonin receptor-specific activator is administered to or near a secondary lymphoid organ. In some embodiments of any of the foregoing aspects, the calcitonin receptor activator or calcitonin receptor-specific activator is administered to or near a tertiary lymphoid organ. In some embodiments of any of the foregoing aspects, the calcitonin receptor activator or calcitonin receptor-specific activator is administered to or near a barrier tissue. In some embodiments of any of the foregoing aspects, the calcitonin receptor activator or calcitonin receptor-specific activator is administered to or near the skin. In some embodiments of any of the foregoing aspects, the calcitonin receptor activator or calcitonin receptor-specific activator is administered to or near the gut. In some embodiments of any of the foregoing aspects, the calcitonin receptor activator or calcitonin receptor-specific activator is administered to or near an airway. In some embodiments of any of the foregoing aspects, the calcitonin receptor activator or calcitonin receptor-specific activator is administered to or near a wound.

In some embodiments of any of the foregoing aspects, the method further includes administering a second therapeutic agent.

In some embodiments of any of the foregoing aspects, the calcitonin receptor activator or calcitonin receptor-specific activator improves organ function, decreases immune cell migration, decreases immune cell proliferation, decreases immune cell recruitment, decreases immune cell activation, decreases immune cell polarization, decreases immune cell cytokine production, decreases immune cell degranulation, increases immune cell lymph node homing, decreases immune cell lymph node egress, decreases immune cell maturation, decreases immune cell ADCC, decreases immune cell ADCP, decreases immune cell antigen presentation, increases immune cell calcitonin receptor expression (e.g., expression of CALCR and/or RAMP1), decreases inflammation, controls infection, decreases viral load, decreases auto-antibody levels, and/or decreases the rate or number of relapses or flare-ups.

In some embodiments of any of the foregoing aspects, the method further includes measuring one or more of organ function, inflammation, auto-antibody levels, the rate or number of relapses or flare-ups, viral load, control of infection, development of high endothelial venules (HEVs) or tertiary lymphoid organs (TLOs), immune cell migration, immune cell proliferation, immune cell recruitment, lymph node homing, lymph node egress, immune cell differentiation, immune cell activation, immune cell polarization, immune cell cytokine production, immune cell degranulation, immune cell maturation, ADCC, ADCP, organ function, viral load, auto-antibody levels, inflammation, or immune cell calcitonin receptor expression (e.g., expression of CALCR and/or RAMP1) before administration of the calcitonin receptor activator or calcitonin receptor-specific activator.

In some embodiments of any of the foregoing aspects, the method further includes measuring one or more of organ function, inflammation, auto-antibody levels, the rate or number of relapses or flare-ups, viral load, control of infection, development of HEVs or TLOs, immune cell migration, immune cell proliferation, immune cell recruitment, lymph node homing, lymph node egress, immune cell differentiation, immune cell activation, immune cell polarization, immune cell cytokine production, immune cell degranulation, immune cell maturation, ADCC, ADCP, organ function, viral load, auto-antibody levels, inflammation, or immune cell calcitonin receptor (e.g., expression of CALCR and/or RAMP1) expression after administration of the calcitonin receptor activator or calcitonin receptor-specific activator.

In some embodiments of any of the foregoing aspects, immune cell activation, immune cell proliferation, or immune cell polarization are measured based on expression of one or more immune cell markers.

In some embodiments of any of the foregoing aspects, the one or more immune cell markers is a marker listed in Table 1.

In some embodiments of any of the foregoing aspects, the calcitonin receptor activator or calcitonin receptor-specific activator is administered in an amount sufficient to improve organ function, increase immune cell lymph node homing, increase immune cell calcitonin receptor expression (e.g., expression of CALCR and/or RAMP1), decrease immune cell migration, decrease immune cell proliferation, decrease immune cell recruitment, decrease immune cell lymph node egress, decrease immune cell differentiation, decrease immune cell activation, decrease immune cell polarization, decrease immune cell cytokine production, decrease immune cell degranulation, decrease immune cell maturation, decrease immune cell ADCC, decrease immune cell ADCP, decrease immune cell antigen proliferation, decrease inflammation, decrease auto-antibody levels, control infection, decrease viral load, and/or decrease rate or number of relapses or flare-ups.

In some embodiments of any of the foregoing aspects, the method further includes monitoring the progression of the inflammatory or autoimmune disease or condition after administration of the calcitonin receptor activator or calcitonin receptor-specific activator (e.g., monitoring one or more of organ function, inflammation, auto-antibody levels, the rate or number of relapses or flare-ups, viral load, control of infection, development of HEVs or TLOs, immune cell migration, immune cell proliferation, immune cell recruitment, lymph node homing, lymph node egress, immune cell differentiation, immune cell activation, immune cell polarization, immune cell cytokine production, immune cell degranulation, immune cell maturation, ADCC, ADCP, or immune cell calcitonin receptor (e.g., expression of CALCR and/or RAMP1) expression).

In some embodiments of any of the foregoing aspects, the calcitonin receptor is CALCR and/or RAMP1 (e.g., CALCR and RAMP1, e.g., AMY1 receptor).

In some embodiments of any of the foregoing aspects, the subject is not diagnosed as having a metabolic disease (e.g., obesity, Type 1 diabetes, or Type 2 diabetes), osteoporosis, or osteopenia.

In some embodiments of any of the foregoing aspects, the cytokine is a pro-inflammatory cytokine. In some embodiments, the pro-inflammatory cytokine is IL-6 or IFNγ.

In some embodiments of any of the foregoing aspects, the immune cell is selected from the group consisting of a regulatory T cell (Treg), T effector cell, a T helper cell, a Th1 cell, a Th2 cell, a Th17 cell, a B cell, a natural killer (NK) cell, an innate lymphoid cell 1 (ILC1), and ILC2, and ILC3, a monocyte, a macrophage, a dendritic cell, an M1 macrophage, an M2 macrophage, and an antigen presenting cell.

In some embodiments of any of the foregoing aspects, the immune cell is a macrophage (e.g., an M2 macrophage or an M1 macrophage).

In some embodiments of any of the foregoing aspects, the immune cell expresses a calcitonin receptor (e.g., CALCR and/or RAMP1, e.g., AMY1 receptor).

In another aspect, the invention provides a therapy for treating an anti-inflammatory or autoimmune disease or condition containing a calcitonin receptor activator and a second agent selected from the group consisting of a disease-modifying anti-rheumatic drug (DMARD), a biologic response modifier (a type of DMARD), a corticosteroid, a nonsteroidal anti-inflammatory medication (NSAID), prednisone, prednisolone, methylprednisolone, methotrexate, hydroxychloroquine, sulfasalazine, leflunomide, cyclophosphamide, azathioprine, tofacitinib, adalimumab, abatacept, anakinra, kineret, certolizumab, etanercept, golimumab, infliximab, rituximab tocilizumab, an antiviral compound, a nucleoside-analog reverse transcriptase inhibitor (NRTI), a non-nucleoside reverse transcriptase inhibitor (NNRTI), an antibacterial compound, an antifungal compound, an antiparasitic compound, 6-mercaptopurine, 6-thioguanine, alemtuzumab, aminosalicylates, antibiotics, anti-histamines, anti-TNFα, azathioprine, belimumab, beta interferon, calcineurin inhibitors, certolizumab, corticosteroids, cromolyn, cyclosporin A, cyclosporine, dimethyl fumarate, fingolimod, fumaric acid esters, glatiramer acetate, golimumab, hydroxyurea, IFNγ, IL-11, leukotriene receptor antagonist, long-acting beta2 agonist, methotrexate, mitoxantrone, mycophenolate mofetil, natalizumab, ocrelizumab, pimecrolimus, probiotics, retinoids, rituximab, salicylic acid, short-acting beta2 agonist, sulfasalazine, tacrolimus, teriflunomide, theophylline, ustekinumab, vedolizumab, a neurotransmission modulator, or a neuronal growth factor modulator.

In some embodiments of any of the foregoing aspects, the calcitonin receptor activator is a calcitonin receptor-specific activating antibody or an antigen binding fragment thereof (e.g., a CALCR-specific activating antibody or an antigen binding fragment thereof, a RAMP1-specific activating antibody or an antigen binding fragment thereof, or an AMY1 receptor-specific activating antibody or an antigen binding fragment thereof).

In some embodiments of any of the foregoing aspects, the calcitonin receptor activator is a soluble calcitonin receptor binding partner or a fragment thereof (e.g., calcitonin, CGRP neuropeptide, or amylin or a calcitonin, CGRP neuropeptide, or amylin-derived sequence). In some embodiments of any of the foregoing aspects, the soluble calcitonin receptor binding partner is fused (e.g., linked or conjugated) to an Fc domain, albumin, or other protein scaffold, PEGylated, or formulated for local injection or depot injection. In some embodiments of any of the foregoing aspects, the soluble calcitonin receptor binding partner or a fragment thereof is Pramlintide or Salmon calcitonin (DrugBank DB00017). In some embodiments of any of the foregoing aspects, the calcitonin receptor activator is KBP-042 or KBP-089.

In some embodiments of any of the foregoing aspects, the calcitonin receptor activator is an mRNA encoding a soluble calcitonin receptor binding partner or a fragment thereof (e.g., calcitonin, CGRP neuropeptide, or amylin or a calcitonin, CGRP neuropeptide, or amylin-derived sequence).

In some embodiments of any of the foregoing aspects, the calcitonin receptor activator is a calcitonin receptor function activator.

In another aspect, the invention provides a pharmaceutical composition containing a calcitonin receptor activator.

In some embodiments of any of the foregoing aspects, the calcitonin receptor activator is a calcitonin receptor-specific activating antibody or an antigen binding fragment thereof (e.g., a CALCR-specific activating antibody or an antigen binding fragment thereof, a RAMP1-specific activating antibody or an antigen binding fragment thereof, or an AMY1 receptor-specific activating antibody or an antigen binding fragment thereof).

In some embodiments, the calcitonin receptor-specific activating antibody or antigen binding fragment thereof exhibits one or more of the following activities: (a) agonizes the calcitonin receptor (e.g., agonizes the AMY1 receptor); (b) agonizes CALCR; (c) agonizes RAMP1; (d) binds to one or more of amino acids 43-171 of the N-terminal extracellular domain of CALCR, or (e) binds to one or more of amino acids 27-117 of the extracellular domain of RAMP1.

In some embodiments of any of the foregoing aspects, the calcitonin receptor activator is a soluble calcitonin receptor binding partner or a fragment thereof (e.g., calcitonin, CGRP neuropeptide, or amylin or a calcitonin, CGRP neuropeptide, or amylin-derived sequence). In some embodiments of any of the foregoing aspects, the soluble calcitonin receptor binding partner is a soluble, signaling capable calcitonin, CGRP neuropeptide, or amylin peptide or a fragment thereof. In some embodiments of any of the foregoing aspects, the soluble, signaling capable calcitonin, CGRP neuropeptide, or amylin or a fragment thereof is an Fc-fusion peptide (e.g., is fused or linked to the Fc domain of an antibody), or is fused to albumin or another protein scaffold. In some embodiments of any of the foregoing aspects, the soluble, calcitonin, CGRP neuropeptide, or amylin peptide or a fragment thereof is PEGylated or formulated for local or depot injection. In some embodiments of any of the foregoing aspects, the soluble calcitonin receptor binding partner binds to the calcitonin receptor and exhibits one or more of the following activities: (a) agonizes the calcitonin receptor (e.g., agonizes the AMY1 receptor), (b) agonizes CALCR, (c) agonizes RAMP1, (d) binds to one or more of amino acids 43-171 of the N-terminal extracellular domain of CALCR, or (e) binds to one or more of amino acids 27-117 of the extracellular domain of RAMP1. In some embodiments of any of the foregoing aspects, the calcitonin receptor activator is an mRNA encoding a soluble calcitonin receptor binding partner or a fragment thereof (e.g., calcitonin, CGRP neuropeptide, or amylin or a calcitonin, CGRP neuropeptide, or amylin-derived sequence).

In some embodiments of any of the foregoing aspects, the pharmaceutical composition further includes a second therapeutic agent.

In some embodiments of any of the foregoing aspects, the composition further includes a pharmaceutically acceptable excipient.

In some embodiments of any of the foregoing aspects, the second therapeutic agent is a disease-modifying anti-rheumatic drug (DMARD), a biologic response modifier (a type of DMARD), a corticosteroid, a nonsteroidal anti-inflammatory medication (NSAID), prednisone, prednisolone, methylprednisolone, methotrexate, hydroxychloroquine, sulfasalazine, leflunomide, cyclophosphamide, azathioprine, tofacitinib, adalimumab, abatacept, anakinra, kineret, certolizumab, etanercept, golimumab, infliximab, rituximab tocilizumab, an antiviral compound, a nucleoside-analog reverse transcriptase inhibitor (NRTI), a non-nucleoside reverse transcriptase inhibitor (NNRTI), an antibacterial compound, an antifungal compound, an antiparasitic compound, 6-mercaptopurine, 6-thioguanine, alemtuzumab, aminosalicylates, antibiotics, anti-histamines, anti-TNFα, azathioprine, belimumab, beta interferon, calcineurin inhibitors, certolizumab, corticosteroids, cromolyn, cyclosporin A, cyclosporine, dimethyl fumarate, fingolimod, fumaric acid esters, glatiramer acetate, golimumab, hydroxyurea, IFNγ, IL-11, leukotriene receptor antagonist, long-acting beta2 agonist, methotrexate, mitoxantrone, mycophenolate mofetil, natalizumab, ocrelizumab, pimecrolimus, probiotics, retinoids, rituximab, salicylic acid, short-acting beta2 agonist, sulfasalazine, tacrolimus, teriflunomide, theophylline, ustekinumab, vedolizumab, a calcitonin receptor function activator, a neurotransmission modulator, or a neuronal growth factor modulator.

In some embodiments of any of the foregoing aspects, the neurotransmission modulator is neurotoxin listed in Table 8, or a modulator (e.g., agonist or antagonist) of a neurotransmitter receptor listed in Table 4 or a neurotransmitter listed in Table 4. In some embodiments, the modulator of a neurotransmitter receptor listed in Table 4 or a neurotransmitter listed in Table 4 is an agonist or antagonist listed in Tables 6A-6K or a modulator listed in Table 7.

In some embodiments of any of the foregoing aspects, the neuronal growth factor modulator is an agonist or an antagonist of a neuronal growth factor listed in Table 9. In some embodiments, the agonist or antagonist of a neuronal growth factor listed in Table 9 is an antibody listed in Table 10 or an agonist or antagonist listed in Table 11. In some embodiments, the antagonist of a neuronal growth factor listed in Table 9 is selected from the group consisting of etanercept, thalidomide, lenalidomide, pomalidomide, pentoxifylline, bupropion, DOI, disitertide, and trabedersen.

In some embodiments of any of the foregoing aspects, the inflammatory or autoimmune disease or condition is MS, psoriasis, Crohn's disease, IBD, ulcerative colitis, dermatitis, asthma, fibrosis, or wound healing. In some embodiments of any of the foregoing aspects, the inflammatory or autoimmune disease or condition is ulcerative colitis. In some embodiments of any of the foregoing aspects, the inflammatory or autoimmune disease or condition is a calcitonin receptor-associated inflammatory or autoimmune disease or condition. In some embodiments, the calcitonin receptor-associated inflammatory or autoimmune disease or condition is associated with expression of a calcitonin receptor (e.g., CALCR and/or RAMP1) in immune cells.

In some embodiments of any of the foregoing aspects, the calcitonin receptor function activator is a calcitonin receptor-specific activating antibody or an antigen binding fragment thereof (e.g., an agonist antibody, e.g., a CALCR-specific activating antibody or an antigen binding fragment thereof, a RAMP1-specific activating antibody or an antigen binding fragment thereof, or an AMY1 receptor-specific activating antibody or an antigen binding fragment thereof). In some embodiments of any of the foregoing aspects, the calcitonin receptor function activator is a soluble calcitonin receptor binding partner or a fragment thereof (e.g., calcitonin, CGRP neuropeptide, or amylin or a calcitonin, CGRP neuropeptide, or amylin-derived sequence). In some embodiments, the soluble calcitonin receptor binding partner or fragment thereof is fused (e.g., linked or conjugated) to an Fc domain, fused to albumin or another protein scaffold, PEGylated, or formulated for local injection or depot injection. In some embodiments of any of the foregoing aspects, the calcitonin receptor function activator is an mRNA encoding a soluble calcitonin receptor binding partner or a fragment thereof (e.g., calcitonin, CGRP neuropeptide, or amylin or a calcitonin, CGRP neuropeptide, or amylin-derived sequence). In some embodiments of any of the foregoing aspects, the calcitonin receptor function activator is pramlintide, salmon calcitonin (DrugBank DB00017), KBP-042, or KBP-089.

In some embodiments of any of the foregoing aspects, the calcitonin receptor activator or calcitonin receptor-specific activator is selected from the group consisting of an antibody, a polypeptide, a DNA molecule, an RNA molecule, and a viral vector. In some embodiments, the antibody is a calcitonin receptor activating antibody or an antigen binding fragment thereof. In some embodiments, the calcitonin receptor activating antibody is a calcitonin receptor-specific activating antibody or an antigen binding fragment thereof (e.g., a CALCR-specific activating antibody or an antigen binding fragment thereof, a RAMP1-specific activating antibody or an antigen binding fragment thereof, or an AMY1 receptor-specific activating antibody or an antigen binding fragment thereof). In some embodiments, the polypeptide is a soluble calcitonin receptor binding partner or a fragment thereof (e.g., calcitonin, CGRP neuropeptide, or amylin or a calcitonin, CGRP neuropeptide, or amylin-derived sequence). In some embodiments, the DNA, RNA, or viral vector encodes or expresses a soluble calcitonin receptor binding partner or a fragment thereof (e.g., calcitonin, CGRP neuropeptide, or amylin, or a calcitonin, CGRP neuropeptide, or amylin-derived sequence). In some embodiments, the soluble calcitonin receptor binding partner of fragment thereof is fused to an Fc domain, fused to albumin or another protein scaffold, PEGylated, or formulated for local injection or depot injection.

In some embodiments of any of the foregoing aspects, the calcitonin receptor activator is an AMY1 receptor activator (e.g., pramlintide).

In some embodiments of any of the foregoing aspects, the composition further includes a pharmaceutically acceptable excipient.

In some embodiments of any of the foregoing aspects, the calcitonin receptor activator or calcitonin receptor-specific activator does not cross the blood brain barrier. In some embodiments, the calcitonin receptor activator or the calcitonin receptor-specific activator has been modified to prevent blood brain barrier crossing by conjugation to a targeting moiety, formulation in a particulate delivery system, addition of a molecular adduct, or through modulation of its size, polarity, flexibility, or lipophilicity.

In some embodiments of any of the foregoing aspects, the calcitonin receptor activator or calcitonin receptor-specific activator does not have a direct effect on the central nervous system or gut.

In some embodiments of any of the foregoing aspects, the immune cell is a macrophage (e.g., an M1 or M2 macrophage). In some embodiments of any of the foregoing aspects, the method decreases macrophage migration, macrophage proliferation, macrophage recruitment, macrophage lymph node egress, macrophage differentiation, macrophage activation, macrophage polarization, macrophage cytokine production, macrophage maturation, macrophage antigen presentation, macrophage calcitonin receptor expression, macrophage ADCC, macrophage ADCP, or organ function. In some embodiments, the method increases macrophage lymph node homing and/or improves organ function. In some embodiments, the cytokine is a pro-inflammatory cytokine. In some embodiments, the cytokine is IL-6 and/or IFNγ. In some embodiments, the method decreases inflammation, auto-antibody levels, viral load, or the rate or number of relapses or flare-ups.

Definitions

As used herein, "administration" refers to providing or giving a subject a therapeutic agent (e.g., a calcitonin receptor activator), by any effective route. Exemplary routes of administration are described herein below.

As used herein, the term "agonist" refers to an agent (e.g., a small molecule or antibody) that increases receptor activity. An agonist may activate a receptor by directly binding to the receptor, by acting as a cofactor, by modulating receptor conformation (e.g., maintaining a receptor in an open or active state). An agonist may increase receptor activity by 10%, 20%, 30%, 40%, 50%, 60%, 70%, 80%, 90%, 95%, 98% or more. An agonist may induce maximal receptor activation or partial activation depending on the concentration of the agonist and its mechanism of action.

As used herein, the term "analog" refers to a protein of similar nucleotide or amino acid composition or sequence to any of the proteins or peptides of the invention, allowing for variations that do not have an adverse effect on the ability of the protein or peptide to carry out its normal function (e.g., bind to a receptor or promote synapse formation). Analogs may be the same length, shorter, or longer than their corresponding protein or polypeptide. Analogs may have about 60% (e.g., about 60%, about 62%, about 64%, about 66%, about 68%, about 70%, about 72%, about 74%, about 76%, about 78%, about 80%, about 82%, about 84%, about 86%, about 88%, about 90%, about 92%, about 94%, about 96%, about 98%, or about 99%) identity to the amino acid sequence of the naturally occurring protein or peptide. An analog can be a naturally occurring protein or polypeptide sequence that is modified by deletion, addition, mutation, or substitution of one or more amino acid residues.

As used herein, the term "antagonist" refers to an agent (e.g., a small molecule or antibody) that reduces or inhibits receptor activity. An antagonist may reduce receptor activity by directly binding to the receptor, by blocking the receptor binding site, by modulating receptor conformation (e.g., maintaining a receptor in a closed or inactive state). An antagonist may reduce receptor activity by 10%, 20%, 30%, 40%, 50%, 60%, 70%, 80%, 90%, 95%, 98% or more. An antagonist may also completely block or inhibit receptor activity. Antagonist activity may be concentration-dependent or -independent.

As used herein, the term "antibody" refers to a molecule that specifically binds to, or is immunologically reactive with, a particular antigen and includes at least the variable domain of a heavy chain, and normally includes at least the variable domains of a heavy chain and of a light chain of an immunoglobulin. Antibodies and antigen-binding fragments, variants, or derivatives thereof include, but are not limited to, polyclonal, monoclonal, multispecific, human, humanized, primatized, or chimeric antibodies, heteroconjugate antibodies (e.g., bi- tri- and quad-specific antibodies, diabodies, triabodies, and tetrabodies), single-domain antibodies (sdAb), epitope-binding fragments, e.g., Fab, Fab' and F(ab')$_2$, Fd, Fvs, single-chain Fvs (scFv), rIgG, single-chain antibodies, disulfide-linked Fvs (sdFv), fragments including either a $V_L$ or $V_H$ domain, fragments produced by an Fab expression library, and anti-idiotypic (anti-Id) antibodies. Antibody molecules of the invention can be of any type (e.g., IgG, IgE, IgM, IgD, IgA, and IgY), class (e.g., IgG1, IgG2, IgG3, IgG4, IgA1 and IgA2) or subclass of immunoglobulin molecule. Moreover, unless otherwise indicated, the term "monoclonal antibody" (mAb) is meant to include both intact molecules as well as antibody fragments (such as, for example, Fab and F (ab')$_2$ fragments) that are capable of specifically binding to a target protein. Fab and F (ab')$_2$ fragments lack the Fc fragment of an intact antibody.

The term "antigen-binding fragment," as used herein, refers to one or more fragments of an immunoglobulin that retain the ability to specifically bind to a target antigen. The antigen-binding function of an immunoglobulin can be performed by fragments of a full-length antibody. The antibody fragments can be a Fab, F(ab')$_2$, scFv, SMIP, diabody, a triabody, an affibody, a nanobody, an aptamer, or a domain antibody. Examples of binding fragments encompassed by the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment containing two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb (Ward et al., Nature 341:544-546, 1989) including $V_H$ and $V_L$ domains; (vi) a dAb fragment that consists of a $V_H$ domain; (vii) a dAb that consists of a $V_H$ or a $V_L$ domain; (viii) an isolated complementarity determining region (CDR); and (ix) a combination of two or more isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv)). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "binding partner" refers to a polypeptide or fragment thereof that binds to a protein of interest (e.g., a calcitonin receptor, e.g., CALCR or RAMP1). Binding partners include receptors and other molecules that selectively bind to the ligand of interest. Exemplary calcitonin receptor binding partners include calcitonin encoded by the CALCA gene (Entrez Gene ID: 796), CGRP neuropeptide encoded by the CALCA gene (amino acids 83-119 of the pro-peptide) (Entrez Gene ID: 796), and Amylin encoded by the IAPP gene (Entrez Gene ID: 3375).

As used herein, the term "cell type" refers to a group of cells sharing a phenotype that is statistically separable based on gene expression data. For instance, cells of a common cell type may share similar structural and/or functional characteristics, such as similar gene activation patterns and antigen presentation profiles. Cells of a common cell type may include those that are isolated from a common tissue (e.g., epithelial tissue, neural tissue, connective tissue, barrier tissue, mucosal tissue, gut, or muscle tissue) and/or those that are isolated from a common organ, tissue system, blood vessel, or other structure and/or region in an organism.

As used herein, a "combination therapy" or "administered in combination" means that two (or more) different agents or treatments are administered to a subject as part of a defined treatment regimen for a particular disease or condition. The treatment regimen defines the doses and periodicity of administration of each agent such that the effects of the separate agents on the subject overlap. In some embodiments, the delivery of the two or more agents is simultaneous or concurrent and the agents may be co-formulated. In other embodiments, the two or more agents are not co-formulated and are administered in a sequential manner as part of a prescribed regimen. In some embodiments, administration of two or more agents or treatments in combination is such that the reduction in a symptom, or other parameter related to the disorder is greater than what would be observed with one agent or treatment delivered alone or in the absence of the other. The effect of the two treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, inhalation routes, and direct absorption through mucous membrane tissues. The therapeutic agents can be administered by the same route or by different routes. For example, a first therapeutic agent of the combination may be administered by intravenous injection while a second therapeutic agent of the combination may be administered orally.

As used herein, the terms "effective amount," "therapeutically effective amount," and a "sufficient amount" of a composition, antibody, vector construct, viral vector or cell described herein refer to a quantity sufficient to, when administered to a subject, including a mammal (e.g., a human), effect beneficial or desired results, including effects at the cellular level, tissue level, or clinical results, and, as such, an "effective amount" or synonym thereto depends upon the context in which it is being applied. For example, in the context of treating inflammatory or autoimmune disease or condition it is an amount of the composition, antibody, vector construct, viral vector or cell sufficient to achieve a treatment response as compared to the response obtained without administration of the composition, antibody, vector construct, viral vector or cell. The amount of a given composition described herein that will correspond to such an amount will vary depending upon various factors, such as the given agent, the pharmaceutical formulation, the route of administration, the type of disease or disorder, the identity of the subject (e.g., age, sex, weight) or host being treated, and the like, but can nevertheless be routinely determined by one skilled in the art. Also, as used herein, a "therapeutically effective amount" of a composition, antibody, vector construct, viral vector or cell of the present disclosure is an amount that results in a beneficial or desired result in a subject as compared to a control. As defined herein, a therapeutically effective amount of a composition, antibody, vector construct, viral vector or cell of the present disclosure may be readily determined by one of ordinary skill by routine methods known in the art. Dosage regimen may be adjusted to provide the optimum therapeutic response.

As used herein, the terms "increasing" and "decreasing" refer to modulating resulting in, respectively, greater or lesser amounts, of function, expression, or activity of a metric relative to a reference. For example, subsequent to administration of a calcitonin receptor activator in a method described herein, the amount of a marker of a metric (e.g., immune cell activation, proliferation, phagocytosis, antibody-dependent cell-mediated cytotoxicity (ADCC), antibody-dependent cell-mediated phagocytosis (ADCP), antigen presentation, lymph node homing, lymph node egress, differentiation, degranulation, polarization, cytokine production, recruitment, or migration) as described herein may be increased or decreased in a subject by at least 5%, 10%, 15%, 20%, 25%, 30%, 35%, 40%, 45%, 50%, 55%, 60%, 65%, 70%, 75%, 80%, 85%, 90%, 95% or 98% or more relative to the amount of the marker prior to administration. Generally, the metric is measured subsequent to administration at a time that the administration has had the recited effect, e.g., at least one week, one month, 3 months, or 6 months, after a treatment regimen has begun.

As used herein, the term "innervated" refers to a tissue (e.g., a lymph node) that contains nerves. "Innervation" refers to the process of nerves entering a tissue.

As used herein, "locally" or "local administration" means administration at a particular site of the body intended for a local effect and not a systemic effect. Examples of local administration are epicutaneous, inhalational, intra-articular, intrathecal, intravaginal, intravitreal, intrauterine, intra-lesional administration, lymph node administration, intratumoral administration and administration to a mucous membrane of the subject, wherein the administration is intended to have a local and not a systemic effect.

As used herein, the term "percent (%) sequence identity" refers to the percentage of amino acid (or nucleic acid) residues of a candidate sequence that are identical to the amino acid (or nucleic acid) residues of a reference sequence after aligning the sequences and introducing gaps, if necessary, to achieve the maximum percent sequence identity (e.g., gaps can be introduced in one or both of the candidate and reference sequences for optimal alignment and non-homologous sequences can be disregarded for comparison purposes). Alignment for purposes of determining percent sequence identity can be achieved in various ways that are within the skill in the art, for instance, using publicly available computer software, such as BLAST, ALIGN, or Megalign (DNASTAR) software. Those skilled in the art can determine appropriate parameters for measuring alignment, including any algorithms needed to achieve maximal alignment over the full length of the sequences being compared. For example, a reference sequence aligned for comparison with a candidate sequence may show that the candidate sequence exhibits from 50% to 100% sequence identity across the full length of the candidate sequence or a selected portion of contiguous amino acid (or nucleic acid) residues of the candidate sequence. The length of the candidate sequence aligned for comparison purposes may be, for example, at least 30%, (e.g., 30%, 40, 50%, 60%, 70%, 80%, 90%, or 100%) of the length of the reference sequence. When a position in the candidate sequence is occupied by the same amino acid residue as the corresponding position in the reference sequence, then the molecules are identical at that position.

As used herein, a "pharmaceutical composition" or "pharmaceutical preparation" is a composition or preparation having pharmacological activity or other direct effect in the mitigation, treatment, or prevention of disease, and/or a finished dosage form or formulation thereof and which is indicated for human use.

As used herein, the term "pharmaceutically acceptable" refers to those compounds, materials, compositions and/or dosage forms, which are suitable for contact with the tissues of a subject, such as a mammal (e.g., a human) without excessive toxicity, irritation, allergic response and other problem complications commensurate with a reasonable benefit/risk ratio.

As used herein, the term "proliferation" refers to an increase in cell numbers through growth and division of cells.

As used herein, the term "reference" refers to a level, expression level, copy number, sample or standard that is used for comparison purposes. For example, a reference sample can be obtained from a healthy individual (e.g., an individual who does not have an autoimmune or inflammatory disease or condition). A reference level can be the level of expression of one or more reference samples. For example, an average expression (e.g., a mean expression or median expression) among a plurality of individuals (e.g., healthy individuals, or individuals who do not have an autoimmune or inflammatory disease or condition). In other instances, a reference level can be a predetermined threshold level, e.g., based on functional expression as otherwise determined, e.g., by empirical assays.

As used herein, the term "sample" refers to a specimen (e.g., blood, blood component (e.g., serum or plasma), urine, saliva, amniotic fluid, cerebrospinal fluid, tissue (e.g., barrier tissue, skin, gut tissue, airway tissue, wound tissue, placental, or dermal), pancreatic fluid, chorionic villus sample, and cells) isolated from a subject.

As used herein, the terms "subject" and "patient" refer to an animal (e.g., a mammal, such as a human). A subject to be treated according to the methods described herein may be one who has been diagnosed with a particular condition, or one at risk of developing such conditions. Diagnosis may be performed by any method or technique known in the art. One skilled in the art will understand that a subject to be treated according to the present disclosure may have been subjected to standard tests or may have been identified, without examination, as one at risk due to the presence of one or more risk factors associated with the disease or condition.

"Treatment" and "treating," as used herein, refer to the medical management of a subject with the intent to improve, ameliorate, stabilize (i.e., not worsen), prevent or cure a disease, pathological condition, or disorder. This term includes active treatment (treatment directed to improve the disease, pathological condition, or disorder), causal treatment (treatment directed to the cause of the associated disease, pathological condition, or disorder), palliative treatment (treatment designed for the relief of symptoms), preventative treatment (treatment directed to minimizing or partially or completely inhibiting the development of the associated disease, pathological condition, or disorder); and supportive treatment (treatment employed to supplement another therapy). Treatment also includes diminishment of the extent of the disease or condition; preventing spread of the disease or condition; delay or slowing the progress of the disease or condition; amelioration or palliation of the disease or condition; and remission (whether partial or total), whether detectable or undetectable. "Ameliorating" or "palliating" a disease or condition means that the extent and/or undesirable clinical manifestations of the disease, disorder, or condition are lessened and/or time course of the progression is slowed or lengthened, as compared to the extent or time course in the absence of treatment. "Treatment" can also mean prolonging survival as compared to expected survival if not receiving treatment. Those in need of treatment include those already with the condition or disorder, as well as those prone to have the condition or disorder or those in which the condition or disorder is to be prevented.

As used herein, the term "under-expressed" refers to a nucleic acid or polypeptide that is expressed or caused to be expressed or produced in a cell at a lower level than is normally expressed in the corresponding wild-type cell. For example, a calcitonin receptor (e.g., CALCR or RAMP1) is "under-expressed" in an immune cell (e.g., a macrophage)

when a calcitonin receptor is present at a lower level in the immune cell compared to the level in a healthy cell of the same tissue or cell type from the same species or individual. A calcitonin receptor is under-expressed when calcitonin receptor expression is decreased by 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) compared to a reference (e.g., a healthy cell of the same type).

As used herein, the term "activation" refers to the response of an immune cell to a perceived insult. When immune cells become activated, they proliferate, secrete cytokines, differentiate, present antigens, become more polarized, and can become more phagocytic and cytotoxic. Factors that stimulate immune cell activation include pro-inflammatory cytokines, pathogens, and non-self antigen presentation (e.g., antigens from pathogens presented by dendritic cells, macrophages, or B cells).

As used herein, the terms "antibody-dependent cell mediated cytotoxicity" and "antibody-dependent cellular toxicity" (ADCC) refer to the killing of an antibody-coated target cell by a cytotoxic effector cell through a non-phagocytic process, characterized by the release of the content of cytotoxic granules or by the expression of cell death-inducing molecules. ADCC is triggered through interaction of target-bound antibodies (belonging to IgG or IgA or IgE classes) with certain Fc receptors (FcRs), glycoproteins present on the effector cell surface that bind the Fc region of immunoglobulins (Ig). Effector cells that mediate ADCC include natural killer (NK) cells, Innate Lymphoid Cells (ILCs), monocytes, macrophages, neutrophils, eosinophils and dendritic cells.

As used herein, the terms "antibody-dependent cell mediated phagocytosis" and "antibody-dependent cellular phagocytosis" (ADCP) refer to the phagocytosis (e.g., engulfment) of an antibody-coated target cell by immune cells (e.g., phagocytes). ADCP is triggered through interaction of target-bound antibodies (belonging to IgG or IgA or IgE classes) with certain Fc receptors (FcRs, e.g., FcγRIIa, FcγRIIIa, and FcγRI), glycoproteins present on the effector cell surface that bind the Fc region of immunoglobulins (Ig). Effector cells that mediate ADCP include monocytes, macrophages, neutrophils, and dendritic cells.

As used herein, the term "antigen presentation" refers to a process in which fragments of antigens are displayed on the cell surface of immune cells. Antigens are presented to T cells and B cells to stimulate an immune response. Antigen presenting cells include dendritic cells, B cells, and macrophages. Mast cells and neutrophils can also be induced to present antigens.

As used herein, the term "anti-inflammatory cytokine" refers to a cytokine produced or secreted by an immune cell that reduces inflammation. Immune cells that produce and secrete anti-inflammatory cytokines include T cells (e.g., Tregs) macrophages, B cells, and mast cells. Anti-inflammatory cytokines include IL4, IL-10, IL-11, IL-13, interferon alpha (IFNα) and transforming growth factor-beta (TGFβ).

As used herein, the term "chemokine" refers to a type of small cytokine that can induce directed chemotaxis in nearby cells. Classes of chemokines include CC chemokines, CXC chemokines, C chemokines, and CX3C chemokines. Chemokines can regulate immune cell migration and homing, including the migration and homing of monocytes, macrophages, T cells, mast cells, eosinophils, and neutrophils. Chemokines responsible for immune cell migration include CCL19, CCL21, CCL14, CCL20, CCL25, CCL27, CXCL12, CXCL13, CCR9, CCR10, and CXCR5. Chemokines that can direct the migration of inflammatory leukocytes to sites of inflammation or injury include CCL2, CCL3, CCL5, CXCL1, CXCL2, and CXCL8.

As used herein, the term "cytokine" refers to a small protein involved in cell signaling. Cytokines can be produced and secreted by immune cells, such as T cells, B cells, macrophages, and mast cells, and include chemokines, interferons, interleukins, lymphokines, and tumor necrosis factors.

As used herein, the term "cytokine production" refers to the expression, synthesis, and secretion (e.g., release) of cytokines by an immune cell.

As used herein, the term "cytotoxicity" refers to the ability of immune cells to kill other cells. Immune cells with cytotoxic functions release toxic proteins (e.g., perforin and granzymes) capable of killing nearby cells. Natural killer cells, ILCs, and cytotoxic T cells (e.g., CD8+ T cells) are the primary cytotoxic effector cells of the immune system, although dendritic cells, neutrophils, eosinophils, mast cells, basophils, macrophages, and monocytes have been shown to have cytotoxic activity.

As used herein, the term "differentiation" refers to the developmental process of lineage commitment. A "lineage" refers to a pathway of cellular development, in which precursor or "progenitor" cells undergo progressive physiological changes to become a specified cell type having a characteristic function (e.g., nerve cell, immune cell, or endothelial cell). Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). By "committed" or "differentiated" is meant a cell that expresses one or more markers or other characteristic of a cell of a particular lineage.

As used herein, the term "degranulation" refers to a cellular process in which molecules, including antimicrobial and cytotoxic molecules, are released from intracellular secretory vesicles called granules. Degranulation is part of the immune response to pathogens and invading microorganisms by immune cells such as granulocytes (e.g., neutrophils, basophils, and eosinophils), mast cells, and lymphocytes (e.g., natural killer cells, ILCs, and cytotoxic T cells). The molecules released during degranulation vary by cell type and can include molecules designed to kill the invading pathogens and microorganisms or to promote an immune response, such as inflammation.

As used herein, the term "immune dysregulation" refers to a condition in which the immune system is disrupted or responding to an insult. Immune dysregulation includes aberrant activation (e.g., autoimmune disease), activation in response to an injury or disease (e.g., disease-associated inflammation), and activation in response to a pathogen or infection (e.g., parasitic infection). Immune dysregulation also includes under-activation of the immune system (e.g., immunosuppression). Immune dysregulation can be treated using the methods and compositions described herein to direct immune cells to carry out beneficial functions and reduce harmful activities (e.g., reducing activation and pro-inflammatory cytokine secretion in subjects with autoimmune disease).

As used herein, the term "calcitonin receptor-associated inflammatory or autoimmune diseases or conditions" refers to inflammatory or autoimmune diseases or conditions that are associated with immune cells in which a calcitonin receptor (e.g., CALCR and/or RAMP1, e.g., AMY1 receptor) is expressed (e.g., immune cells having decreased expression of a calcitonin receptor (e.g., CALCR and/or RAMP1, e.g., AMY1 receptor) compared to a reference (e.g., an immune cell from a subject that does not have inflammatory or autoimmune diseases or conditions)). The immune cells can be systemic immune cells or immune cells that have infiltrated the affected tissue or tissues (e.g., infiltrating immune cells or tissue resident immune cells). Calcitonin receptor-associated inflammatory or autoimmune diseases or conditions can be identified by assessing an immune cell or a biopsy of an immune-cell infiltrated tissue sample for immune cell calcitonin receptor expression (e.g., gene or protein expression) and comparing it to calcitonin receptor expression in a reference cell.

As used herein, the term "modulating an immune response" refers to any alteration in a cell of the immune system or any alteration in the activity of a cell involved in the immune response. Such regulation or modulation includes an increase or decrease in the number of various cell types, an increase or decrease in the activity of these cells, or any other changes that can occur within the immune system. Cells involved in the immune response include, but are not limited to, T lymphocytes (T cells), B lymphocytes (B cells), natural killer (NK) cells, innate lymphoid cells (ILCs), macrophages, eosinophils, mast cells, dendritic cells and neutrophils. In some cases, "modulating" the immune response means the immune response is stimulated or enhanced, and in other cases "modulating" the immune response means suppression of the immune system.

As used herein, the term "lymph node egress" refers to immune cell exit from the lymph nodes, which occurs during immune cell recirculation. Immune cells that undergo recirculation include lymphocytes (e.g., T cells, B cells, and natural killer cells), which enter the lymph node from blood to survey for antigen and then exit into lymph and return to the blood stream to perform antigen surveillance.

As used herein, the term "lymph node homing" refers to directed migration of immune cells to a lymph node. Immune cells that return to lymph nodes include T cells, B cells, macrophages, and dendritic cells.

As used herein, the term "migration" refers to the movement of immune cells throughout the body. Immune cells can migrate in response to external chemical and mechanical signals. Many immune cells circulate in blood including peripheral blood mononuclear cells (e.g., lymphocytes such as T cells, B cells, natural killer cells, and innate lymphoid cells), monocytes, macrophages, dendritic cells, and polymorphonuclear cells (e.g., neutrophils and eosinophils). Immune cells can migrate to sites of infection, injury, or inflammation, back to the lymph nodes, or to tumors or cancer cells.

As used herein, the term "phagocytosis" refers to the process in which a cell engulfs or ingests material, such as other cells or parts of cells (e.g., bacteria), particles, or dead or dying cells. A cell that capable of performing this function is called a phagocyte. Immune phagocytes include neutrophils, monocytes, macrophages, mast cells, B cells, eosinophils, and dendritic cells.

As used herein, the term "polarization" refers to the ability of an immune cell to shift between different functional states. A cell that is moving toward one of two functional extremes is said to be in the process of becoming more polarized. The term polarization is often used to refer to macrophages, which can shift between states known as M1 and M2. M1, or classically activated, macrophages secrete pro-inflammatory cytokines (e.g., IL-12, TNF, IL-6, IL-8, IL-1B, MCP-1, and CCL2), are highly phagocytic, and respond to pathogens and other environmental insults. M1 macrophages can also be detected by expression of Nos2. M2, or alternatively activated, macrophages secrete a different set of cytokines (e.g., IL-10) and are less phagocytic. M2 macrophages can detected by expression of Arg1, IDO, PF4, CCL24, IL10, and IL4Rα. Cells become polarized in response to external cues such as cytokines, pathogens, injury, and other signals in the tissue microenvironment.

As used herein, the term "pro-inflammatory cytokine" refers to a cytokine secreted from immune cells that promotes inflammation. Immune cells that produce and secrete pro-inflammatory cytokines include T cells (e.g., Th cells) macrophages, B cells, and mast cells. Pro-inflammatory cytokines include interleukin-1 (IL-1, e.g., IL-1β), IL-5, IL-6, IL-8, IL-10, IL-12, IL-13, IL-18, tumor necrosis factor (TNF, e.g., TNFα), interferon gamma (IFNγ), and granulocyte macrophage colony stimulating factor (GMCSF).

As used herein, the term "pro-survival cytokine" refers to a cytokine that promotes the survival of immune cells (e.g., T cells). Pro-survival cytokines include IL-2, IL-4, IL-6, IL-7, and IL-15.

As used herein, the term "recruitment" refers to the re-distribution of immune cells to a particular location (e.g., the site of infection, injury, or inflammation). Immune cells that can undergo this re-distributed and be recruited to sites of injury or disease include monocytes, macrophages, T cells, B cells, dendritic cells, and natural killer cells.

The term "calcitonin receptor activating antibody" or "calcitonin receptor agonizing antibody" refers to antibodies that are capable of binding to the calcitonin receptor (CALCR) or AMY1 receptor (RAMP1 and CALCR), and inducing, activating, or increasing calcitonin receptor and/or AMY1 receptor function and/or activating one or more signal transduction pathways mediated by the calcitonin receptor and/or AMY1 receptor. The term "calcitonin receptor-specific activating antibody" or "calcitonin receptor-specific agonizing antibody" refers to antibodies that bind specifically to the calcitonin receptor and/or AMY1 receptor and induce, activate, or increase calcitonin receptor and/or AMY1 receptor function and/or activate one or more signal transduction pathways mediated by the calcitonin receptor and/or AMY1 receptor. Calcitonin receptor activating antibodies and calcitonin receptor-specific activating antibodies induce or increase calcitonin receptor and/or AMY1 receptor function and/or activate one or more calcitonin receptor-mediated signal transduction pathways by at least 10% (e.g., 10%, 20%, 30%, 40%, 50%, 60%, 70%, 80%, 90%, 95%, 98% or more).

As used herein, the term "calcitonin receptor activator" refers to an agent that induces or increases calcitonin receptor and/or AMY1 receptor function or signaling. Calcitonin receptor activators include calcitonin receptor activating antibodies, soluble, signaling-capable calcitonin receptor binding partners (e.g., calcitonin, CGRP neuropeptide, or amylin) or fragments or Fc fusion proteins thereof, that increase or induce calcitonin receptor and/or AMY1 receptor expression, calcitonin receptor and/or AMY1 receptor binding, calcitonin receptor and/or AMY1 receptor function, or signal transduction downstream of the calcitonin receptor and/or AMY1 receptor. Calcitonin receptor activators increase calcitonin receptor and/or AMY1 receptor function or signaling by 10% or more (e.g., 10%, 20%, 30%, 40%, 50%, 60%, 70%, 80%, 90%, 95%, 98% or more).

As used herein, the term "calcitonin receptor-specific activator" refers to a calcitonin receptor activator that selectively induces or increases calcitonin receptor function or signaling without substantially affecting the function or signaling of any other protein. Calcitonin receptor-specific activators include calcitonin receptor-specific activating antibodies or small molecule activators that bind specifically to a calcitonin receptor without interacting with any other G protein coupled receptors (GPCR). Calcitonin receptor-specific activators reduce calcitonin receptor function or signaling by 10% or more (e.g., 10%, 20%, 30%, 40%, 50%, 60%, 70%, 80%, 90%, 95%, 98% or more).

As used herein, the term "calcitonin receptor function activator" refers to a type of calcitonin receptor activator that increases or induces calcitonin receptor and/or AMY1 receptor function by increasing the expression of calcitonin receptor and/or AMY1 receptor or agonizing the calcitonin receptor and/or AMY1 receptor. Exemplary calcitonin receptor function activators include calcitonin receptor activating antibodies and antigen binding fragments thereof, soluble, signaling-capable calcitonin receptor binding partners (e.g., calcitonin, CGRP neuropeptide, or amylin) or fragments or Fc fusion proteins thereof that bind to an extracellular domain of the calcitonin receptor and/or AMY1 receptor and agonize the calcitonin receptor and/or AMY1 receptor. Calcitonin receptor function activators increase calcitonin receptor and/or AMY1 receptor function by 10% or more (e.g., 10%, 20%, 30%, 40%, 50%, 60%, 70%, 80%, 90%, 95%, 98% or more).

As used herein, an agent that "does not cross the blood brain barrier" is an agent that does not significantly cross the barrier between the peripheral circulation and the brain and spinal cord. This can also be referred to as a "blood brain barrier impermeable" agent. Agents will have a limited ability to cross the blood brain barrier if they are not lipid soluble or have a molecular weight of over 600 Daltons. Agents that typically cross the blood brain barrier can be modified to become blood brain barrier impermeable based on chemical modifications that increase the size or alter the hydrophobicity of the agent, packaging modifications that reduce diffusion (e.g., packaging an agent within a microparticle or nanoparticle), and conjugation to biologics that direct the agent away from the blood brain barrier (e.g., conjugation to a pancreas-specific antibody). An agent that does not cross the blood brain barrier is an agent for which 30% or less (e.g., 30%, 25%, 20%, 15%, 10%, 5%, 2% or less) of the administered agent crosses the blood brain barrier.

As used herein, an agent that "does not have a direct effect on the central nervous system (CNS) or gut" is an agent that does not directly alter neurotransmission, neuronal numbers, or neuronal morphology in the CNS or gut when administered according to the methods described herein. This may be assessed by administering the agents to animal models and performing electrophysiological recordings or immunohistochemical analysis. An agent will be considered not to have a direct effect on the CNS or gut if administration according to the methods described herein has an effect on neurotransmission, neuronal numbers, or neuronal morphology in the CNS or gut that is 50% or less (e.g., 50%, 45%, 40%, 35%, 30%, 25%, 20%, 15%, 10%, 5%, or less) of the effect observed if the same agent is administered directly to the CNS or gut.

As used herein, the term "metabolic disease" refers to a disease, disorder, or syndrome that is related to a subject's metabolism, such as breaking down carbohydrates, proteins, and fats in food to release energy, and converting chemicals into other substances and transporting them inside cells for energy utilization and/or storage. Some symptoms of a metabolic disease include high serum triglycerides, high low-density cholesterol (LDL), low high-density cholesterol (HDL), and/or high fasting insulin levels, elevated fasting plasma glucose, abdominal (central) obesity, and elevated blood pressure. Metabolic diseases increase the risk of developing other diseases, such as cardiovascular disease. Exemplary metabolic diseases include obesity, Type-1 diabetes, and Type-2 diabetes.

As used herein, the term "osteoporosis" refers to the condition characterized by reduced bone mass and disruption of bone architecture, resulting in increased bone fragility and increased fracture risk, and decreased calcification or density of bone. Osteoporosis is a thinning of the bones with reduction in bone mass due to depletion of calcium and bone protein. In osteoporotic patients, bone strength is abnormal, with a resulting increase in the risk of fracture. The fracture can be in the form of cracking (as in a hip fracture) or collapsing (as in a compression fracture of the spine). The spine, hips, and wrists are common areas of osteoporosis-induced bone fractures, although fractures also can occur in other skeletal areas. Unchecked osteoporosis can lead to changes in posture, physical abnormality and decreased mobility. Osteoporosis can be identified by bone mineral density measurements.

As used herein, the term "osteopenia" refers to decreased calcification or density of bone.

As used herein, the term "neuronal growth factor modulator" refers to an agent that regulates neuronal growth, development, or survival. Neuronal growth factors include proteins that promote neurogenesis, neuronal growth, and neuronal differentiation (e.g., neurotrophic factors NGF, NT3, BDNF, CNTF, and GDNF), proteins that promote neurite outgrowth (e.g., axon or dendrite outgrowth or stabilization), or proteins that promote synapse formation (e.g., synaptogenesis, synapse assembly, synaptic adhesion, synaptic maturation, synaptic refinement, or synaptic stabilization). These processes lead to innervation of tissue, including neural tissue, muscle, lymph nodes and tumors, and the formation of synaptic connections between two or more neurons and between neurons and non-neural cells (e.g., immune cells). A neuronal growth factor modulator may block one or more of these processes (e.g., through the use of antibodies that block neuronal growth factors or their receptors) or promote one or more of these processes (e.g., through the use of these proteins or analogs or peptide fragments thereof). Exemplary neuronal growth factors are listed in Table 9. Neuronal growth factor modulators decrease or increase neurite outgrowth, innervation, synapse formation, or any of the aforementioned processes by 10% or more (e.g., 10%, 20%, 30%, 40%, 50%, 60%, 70%, 80%, 90%, 95%, 98% or more).

As used herein, the term "neurotransmission modulator" refers to an agent that either induces or increases neurotransmission or decreases or blocks neurotransmission. Neurotransmission modulators can increase or decrease neurotransmission by 10%, 20%, 30%, 40%, 50%, 60%, 70%, 80%, 90%, 95%, 98% or more. Exemplary neurotransmitters and neurotransmitter receptors are listed in Tables 4 and 5. Neurotransmission modulators may increase neurotransmission by increasing neurotransmitter synthesis or release, preventing neurotransmitter reuptake or degradation, increasing neurotransmitter receptor activity, increasing neurotransmitter receptor synthesis or membrane insertion, decreasing neurotransmitter degradation, and regulating neurotransmitter receptor conformation. Neurotransmission modulators that increase neurotransmission include neurotransmitters and analogs thereof and neurotransmitter receptor agonists. Neurotransmission modulators may decrease neurotransmission by decreasing neurotransmitter synthesis or release, increasing neurotransmitter reuptake or degradation, decreasing neurotransmitter receptor activity, decreasing neurotransmitter receptor synthesis or membrane insertion, increasing neurotransmitter degradation, regulating neurotransmitter receptor conformation, and disrupting the pre- or postsynaptic machinery. Neurotransmission modulators that decrease or block neurotransmission include antibodies that bind to or block the function of neurotransmitters, neurotransmitter receptor antagonists, and toxins that disrupt synaptic release.

DETAILED DESCRIPTION

Described herein are compositions and methods for the treatment of an inflammatory or autoimmune disease or condition in a subject (e.g., a mammalian subject, such as a human) by administering calcitonin receptor activators. Calcitonin receptor activators include activators specific to a calcitonin receptor (e.g., calcitonin receptor-specific activating antibodies) and non-specific activators that could potentially affect other proteins due to their having shared binding partners or signaling pathways with a calcitonin receptor. These methods and compositions provide new mechanistic approaches for treating inflammatory or autoimmune diseases or conditions.

Calcitonin Receptor and AMY1 Receptor

Calcitonin receptor (CALCR, Entrez Gene ID 799) is a G protein-coupled receptor (GPCR) that associates with Receptor Activity Modifying Protein 1 (RAMP1, Entrez Gene ID 10267) to sense calcitonin, amylin, and CGRP via G-protein signaling, subsequently activating adenylate cyclase. RAMP1 is a single-pass transmembrane protein that helps shuttle CALCR to the plasma membrane where it serves as a co-receptor protein forming the AMY1 receptor. GPCRs are integral membrane proteins that possess seven membrane-spanning domains or transmembrane helices. The GPCRs are activated by external signal in the form of a ligand or other signal mediator, which creates a conformational change in the receptor, causing the activation of a G protein. This triggers the activation of signal transduction pathways, and eventually leads to cellular responses.

The present invention relates to the discovery that, contrary to the conventional wisdom that calcitonin receptors are exclusively neuronal proteins, CALCR and RAMP1 are highly expressed in M2 macrophages from human patients. Providing calcitonin receptor agonist to macrophages polarized to an M2 phenotype and stimulated with LPS to initiate polarization to the M1 state reduces the production and/or secretion of IL-6, a pro-inflammatory cytokine normally secreted by M1 macrophages. Additionally, calcitonin receptor agonism decreased interferon gamma (IFNγ) production in M1 macrophages.

These findings indicate that activation of the calcitonin receptor pathway may help to reduce the production of pro-inflammatory cytokines and protect the host from excessive, aberrant immune responses. Through this mechanism, activation of a calcitonin receptor can reduce inflammation, induce tolerance, and be used as a therapeutic strategy for treating inflammatory and autoimmune diseases or conditions.

Calcitonin Receptor Activators

Calcitonin receptor activators described herein can increase or activate calcitonin receptor function or signaling in order to treat inflammatory or autoimmune diseases or conditions. Calcitonin receptor activators can be grouped into categories based on their mechanism of action and their effect on calcitonin receptor: 1) calcitonin receptor-specific activators (e.g., activators that activate only calcitonin receptor function or signaling, such as calcitonin receptor-specific activating antibodies) and 2) calcitonin receptor function activators (e.g., activators that agonize calcitonin receptor or promote or increase calcitonin receptor interaction with a binding partner, e.g., soluble calcitonin receptor binding partners).

Calcitonin Receptor-Specific Activators

In some embodiments, the calcitonin receptor activator is a calcitonin receptor-specific activator. Calcitonin receptor-specific activators selectively increase or activate calcitonin receptor function, expression, or signaling without directly affecting other proteins (e.g., other GPCRs). Calcitonin receptor-specific activators include calcitonin receptor-specific activating antibodies or antigen binding fragments thereof (e.g., agonist antibodies, e.g., CALCR-specific activating antibodies or antigen binding fragments thereof, RAMP1-specific activating antibodies or antigen binding fragments thereof, and AMY1 receptor-specific activating antibodies or antigen binding fragments thereof). Calcitonin receptor-specific activators can increase calcitonin receptor function, expression, or signaling by 5% or more (e.g., 5%, 10%, 15%, 20%, 25%, 30%, 40%, 50%, 60%, 70%, 80%, 90%, 95%, 99%, or more).

In some embodiments, the calcitonin receptor antibody is a calcitonin receptor-specific activating antibody or an antigen binding fragment thereof that binds to a calcitonin receptor (e.g., CALCR, RAMP1, or the AMY1 receptor (CALCR and RAMP1)) and increases or activates calcitonin receptor function. Calcitonin receptor-specific activating antibodies include antibodies that bind to the calcitonin receptor and exhibit one or more of the following activities: (a) agonizes the calcitonin receptor (e.g., agonizes the AMY1 receptor); (b) agonizes CALCR; (c) agonizes RAMP1; (d) binds to one or more of amino acids 43-171 of the N-terminal extracellular domain of CALCR; or (e) binds to one or more of amino acids 27-117 of the extracellular domain of RAMP1. Antibodies having one or more of these functional properties are routinely screened and selected once the desired functional property is identified herein (e.g., by screening of phage display or other antibody libraries).

Calcitonin Receptor Function Activators

In some embodiments, the calcitonin receptor activator is a calcitonin receptor function activator. Calcitonin receptor function activators increase or activate calcitonin receptor function by increasing calcitonin receptor expression or activation or promoting interaction with a calcitonin receptor binding partner. Calcitonin receptor function activators include calcitonin receptor-specific activators that increase or activate calcitonin receptor function or expression (e.g., calcitonin receptor-specific activating antibodies or antigen binding fragments thereof) and soluble calcitonin receptor binding partners or fragments thereof (e.g., calcitonin, CGRP neuropeptide, or amylin peptides, and calcitonin, CGRP neuropeptide, or amylin Fc-fusion proteins). Calcitonin receptor activators also include mRNAs that encode any of the aforementioned soluble calcitonin receptor binding partners.

In some embodiments, the calcitonin receptor function activator is a soluble calcitonin receptor binding partner. In some embodiments, the calcitonin receptor binding partner is a soluble, signaling-capable calcitonin, CGRP neuropeptide, or amylin peptide (e.g., calcitonin, CGRP neuropeptide, or amylin, a calcitonin, CGRP neuropeptide, or amylin-derived sequence, or a fragment thereof that is capable of binding to and activating a calcitonin receptor (e.g., CALCR and/or RAMP1) or increasing calcitonin receptor signaling).

In some embodiments, the soluble, full-length calcitonin receptor binding partner has the sequence of WT human calcitonin (CGNLSTCMLGTYTQDFNKFHTFPQTAIGVGAP (SEQ ID NO.: 1)), or has at least 85% sequence identity (e.g., 85%, 90%, 95%, 96%, 97%, 98%, 99%, or more, sequence identity) to the amino acid sequence of WT calcitonin. In some embodiments, the soluble calcitonin receptor binding partner has the sequence of wild-type CGRP neuropeptide (ACDTATCVTHRLAGLLSRSGGVVKNNFVPTNVGSKAF (SEQ ID NO.: 2)), or has at least 85% sequence identity (e.g., 85%, 90%, 95%, 96%, 97%, 98%, 99%, or more, sequence identity) to the amino acid sequence of WT human CGRP neuropeptide. In some embodiments, the soluble calcitonin receptor binding partner has the sequence of wild-type amylin (MGILKLQVFLIVLSVALNHLKATPIESHQVEKRKCNTATCATQRLANFLVHSSNNFGAILSSTNVGSNTYGKR NAVEVLKREPLNYLPL (SEQ ID NO.: 3)), or has at least 85% sequence identity (e.g., 85%, 90%, 95%, 96%, 97%, 98%, 99%, or more, sequence identity) to the amino acid sequence of WT human amylin. In some embodiments, the soluble calcitonin receptor binding partner is a fragment of the full-length calcitonin receptor binding partner (e.g., a fragment of calcitonin, CGRP neuropeptide, or amylin) that retains the ability to bind to calcitonin receptor. A fragment of a calcitonin receptor binding partner may be made up of the minimal amino acid sequence necessary to bind to calcitonin receptor. In some embodiments, the calcitonin receptor binding partner (e.g., calcitonin, CGRP neuropeptide, or amylin, a calcitonin, CGRP neuropeptide, or amylin-derived sequence, or a fragment thereof) is fused (e.g., linked or conjugated) to an Fc domain, albumin, or other protein scaffold. In some embodiments, the calcitonin receptor binding partner is PEGylated or formulated local injection or depot injection.

To activate calcitonin receptor function, the soluble calcitonin receptor binding partner or a fragment thereof must retain the ability to bind to a calcitonin receptor (e.g., CALCR and/or RAMP1). The soluble calcitonin receptor binding partner or a fragment thereof can bind to an endogenous calcitonin receptor (e.g., a calcitonin receptor expressed by immune cells). The soluble calcitonin receptor binding partner or a fragment thereof binds to a calcitonin receptor and exhibits one or more of the following activities: (a) agonizes the calcitonin receptor (e.g., agonizes the AMY1 receptor); (b) agonizes CALCR; (c) agonizes RAMP1; (d) binds to one or more of amino acids 43-171 of the N-terminal extracellular domain of CALCR; or (e) binds to one or more of amino acids 27-117 of the extracellular domain of RAMP1. For improved stability or increased half-life, the soluble calcitonin receptor binding partner or a fragment thereof can be linked to the Fc region of an antibody (e.g., synthesized as an Fc-fusion protein) or fused to albumin or another protein scaffold. Soluble calcitonin receptor binding partners or fragments thereof can be evaluated using standard experimental methods to determine whether they possess one or more of these functional properties. In some embodiments, the soluble calcitonin receptor binding partner (e.g., calcitonin, CGRP neuropeptide, amylin, or a fragment or Fc fusion thereof) is PEGylated or formulated for local injection or depot injection.

In some embodiments, the calcitonin receptor function activator is an mRNA that encodes any of the aforementioned soluble calcitonin receptor binding partners (e.g., calcitonin, CGRP neuropeptide, amylin, or a fragment or Fc fusion thereof).

In some embodiments, the calcitonin receptor function activator is a peptide analog of amylin, such as pramlintide. In some embodiments, the calcitonin function activator is salmon calcitonin (DrugBank DB00017). In some embodiments, the calcitonin function activator is KBP-042 or KBP-089.

Agent Modalities

A calcitonin receptor activator can be selected from a number of different modalities. A calcitonin receptor activator can be a nucleic acid molecule (e.g., DNA molecule or RNA molecule, e.g., mRNA), small molecule, or a polypeptide (e.g., a soluble calcitonin receptor binding partner or a fragment thereof, or an antibody molecule, e.g., an antibody or antigen binding fragment thereof). A calcitonin receptor activator can also be a viral vector expressing a calcitonin receptor activator (e.g., a soluble calcitonin receptor binding partner) or a cell infected with a viral vector. Any of these modalities can be a calcitonin receptor activator directed to target (e.g., to increase or activate) calcitonin receptor function, calcitonin receptor expression, calcitonin receptor binding, or calcitonin receptor signaling.

The nucleic acid molecule, small molecule, peptide, polypeptide, or antibody molecule can be modified. For example, the modification can be a chemical modification, e.g., conjugation to a marker, e.g., fluorescent marker or a radioactive marker. In other examples, the modification can include conjugation to a molecule that enhances the stability or half-life of the calcitonin receptor activator (e.g., an Fc domain of an antibody or serum albumin, e.g., human serum albumin). The modification can also include conjugation to an antibody to target the agent to a particular cell or tissue. Additionally, the modification can be a chemical modification, packaging modification (e.g., packaging within a nanoparticle or microparticle), or targeting modification to prevent the agent from crossing the blood brain barrier.

Small Molecules

Numerous small molecule calcitonin receptor activators useful in the methods of the invention are described herein and additional small molecule calcitonin receptor activators useful as therapies for inflammatory or autoimmune disease or condition can also be identified through screening based on their ability to reduce or inhibit calcitonin receptor function or signaling. Small molecules include, but are not limited to, small peptides, peptidomimetics (e.g., peptoids), amino acids, amino acid analogs, synthetic polynucleotides, polynucleotide analogs, nucleotides, nucleotide analogs, organic and inorganic compounds (including heterorganic and organometallic compounds) generally having a molecular weight less than about 5,000 grams per mole, e.g., organic or inorganic compounds having a molecular weight less than about 2,000 grams per mole, e.g., organic or inorganic compounds having a molecular weight less than about 1,000 grams per mole, e.g., organic or inorganic compounds having a molecular weight less than about 500 grams per mole, and salts, esters, and other pharmaceutically acceptable forms of such compounds.

Calcitonin receptor activators can be used to treat a disorder or condition described herein. A pharmaceutical composition including the calcitonin receptor activator can be formulated for treatment of an inflammatory or autoimmune disease or condition described herein. In some embodiments, a pharmaceutical composition that includes the calcitonin receptor activator is formulated for local administration, e.g., to the affected site in a subject.

Polypeptides

In some embodiments, a calcitonin receptor activator described herein is a calcitonin receptor activator polypeptide (e.g., a neuropeptide) or an analog thereof. For example, a calcitonin receptor activator described herein is soluble calcitonin receptor binding partner (e.g., calcitonin, CGRP neuropeptide, or amylin) or an analog or fragment thereof.

The calcitonin receptor activator can be a soluble calcitonin receptor binding partner or a fragment thereof. In some embodiments, the soluble calcitonin receptor binding partner or a fragment thereof is calcitonin, CGRP neuropeptide, or amylin, or peptide having a calcitonin, CGRP neuropeptide, or amylin-derived sequence. In some embodiments, the soluble calcitonin, CGRP neuropeptide, or amylin has the sequence of calcitonin, CGRP neuropeptide, or amylin, or has at least 85% sequence identity (e.g., 85%, 90%, 95%, 96%, 97%, 98%, 99%, or more, sequence identity) to the amino acid sequence of wild-type human calcitonin, CGRP neuropeptide, or amylin. In some embodiments, the soluble calcitonin receptor binding partner is a fragment of the full-length calcitonin receptor binding partner that retains the ability to bind to calcitonin receptor. A fragment of a calcitonin receptor binding partner may be made up of the minimal amino acid sequence necessary to bind to calcitonin receptor. In some embodiments, the soluble calcitonin, CGRP neuropeptide, or amylin neuropeptide is an Fc-fusion peptide, or fused to albumin or other protein scaffold.

Percent identity in the context of two or more polypeptide sequences or nucleic acids, refers to two or more sequences that are the same. Two sequences are "substantially identical" if two sequences have a specified percentage of amino acid residues or nucleotides that are the same (e.g., at least 60% identity, e.g., at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% identity, e.g., over a specified region, or, when not specified, over the entire sequence), when compared and aligned for maximum correspondence over a comparison window, or designated region as measured using a sequence comparison algorithms or by manual alignment and visual inspection. In some cases, the identity (or substantial identity) exists over a region that is at least about 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. Methods of alignment of sequences for comparison are well known in the art. Optimal alignment of sequences for comparison can be conducted, e.g., by the local homology algorithm of Smith and Waterman, Adv. Appl. Math. 2:482c, 1970, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, 2003).

Two examples of algorithms that are suitable for determining percent sequence identity and sequence similarity are the BLAST and BLAST 2.0 algorithms, which are described in Altschul et al., Nuc. Acids Res. 25:3389, 1977; and Altschul et al., J. Mol. Biol. 215:403, 1990, respectively. Software for performing BLAST analyses is publicly available through the National Center for Biotechnology Information.

The percent identity between two amino acid sequences can also be determined using the algorithm of E. Meyers and W. Miller, Comput. Appl. Biosci. 4:11, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch, J. Mol. Biol. 48:444, 1970) algorithm which has been incorporated into the GAP program in the GCG software package (available at www.gcg.com), using either a Blossom 62 matrix or a PAM250 matrix, and a gap weight of 16, 14, 12, 10, 8, 6, or 4 and a length weight of 1, 2, 3, 4, 5, or 6.

Methods of making a therapeutic polypeptide are routine in the art. See, in general, Smales & James (Eds.), Therapeutic Proteins: Methods and Protocols (Methods in Molecular Biology), Humana Press 2005; and Crommelin, Sindelar & Meibohm (Eds.), Pharmaceutical Biotechnology: Fundamentals and Applications, Springer 2013.

Some methods for producing a calcitonin receptor activator polypeptide involve expression in mammalian cells, although recombinant proteins can also be produced using insect cells, yeast, bacteria, or other cells under the control of appropriate promoters. Mammalian expression vectors may include nontranscribed elements such as an origin of replication, a suitable promoter and enhancer, and other 5' or 3' flanking nontranscribed sequences, and 5' or 3' nontranslated sequences such as necessary ribosome binding sites, a polyadenylation site, splice donor and acceptor sites, and termination sequences. DNA sequences derived from the SV40 viral genome, for example, SV40 origin, early promoter, enhancer, splice, and polyadenylation sites may be used to provide the other genetic elements required for expression of a heterologous DNA sequence. Appropriate cloning and expression vectors for use with bacterial, fungal, yeast, and mammalian cellular hosts are described in Green & Sambrook, Molecular Cloning: A Laboratory Manual (Fourth Edition), Cold Spring Harbor Laboratory Press 2012.

Various mammalian cell culture systems can be employed to express and manufacture recombinant protein. Examples of mammalian expression systems include CHO cells, COS cells, HeLA and BHK cell lines. Processes of host cell culture for production of protein therapeutics are described in Zhou and Kantardjieff (Eds.), Mammalian Cell Cultures for Biologics Manufacturing (Advances in Biochemical Engineering/Biotechnology), Springer 2014.

Purification of protein therapeutics is known and is described, e.g., in Franks, Protein Biotechnology: Isolation, Characterization, and Stabilization, Humana Press 2013; and in Cutler, Protein Purification Protocols (Methods in Molecular Biology), Humana Press 2010.

Formulation of protein therapeutics is known and is described, e.g., in Meyer (Ed.), Therapeutic Protein Drug Products: Practical Approaches to formulation in the Laboratory, Manufacturing, and the Clinic, Woodhead Publishing Series 2012.

Antibodies

The calcitonin receptor activator can be an antibody or antigen binding fragment thereof. For example, a calcitonin receptor activator described herein is an antibody that increases or activates the activity and/or function of a calcitonin receptor (e.g., CALCR or RAMP1) through binding to a calcitonin receptor to agonize calcitonin receptor.

The making and use of therapeutic antibodies against a target antigen (e.g., a calcitonin receptor) is known in the art. See, for example, the references cited herein above, as well as Zhiqiang An (Editor), Therapeutic Monoclonal Antibodies: From Bench to Clinic. 1st Edition. Wiley 2009, and also Greenfield (Ed.), Antibodies: A Laboratory Manual. (Second edition) Cold Spring Harbor Laboratory Press 2013, for methods of making recombinant antibodies, including antibody engineering, use of degenerate oligonucleotides, 5'-RACE, phage display, and mutagenesis; antibody testing and characterization; antibody pharmacokinetics and pharmacodynamics; antibody purification and storage; and screening and labeling techniques.

Nucleic Acids

Synthetic mRNA

In some embodiments, the calcitonin receptor activator is an mRNA molecule, e.g., a synthetic mRNA molecule encoding a calcitonin receptor activator (e.g., a soluble calcitonin receptor binding partner or a fragment thereof, e.g., soluble calcitonin, CGRP neuropeptide, or amylin). The mRNA molecule may increase the level (e.g., protein and/or mRNA level) and/or activity or function of a calcitonin receptor activator (e.g., a soluble calcitonin receptor binding partner or fragments thereof, e.g., soluble calcitonin, CGRP neuropeptide, or amylin), e.g., a positive regulator of function. For example, the mRNA molecule encodes a polypeptide having at least 50% (e.g., at least 50%, 60%, 70%, 80%, 90%, 95%, 97%, 99%, or greater) identity to the amino acid sequence a calcitonin receptor binding partner (e.g., calcitonin, CGRP neuropeptide, or amylin). In other examples, the mRNA molecule has at least 50% (e.g., at least 50%, 60%, 70%, 80%, 90%, 95%, 97%, 99%, or greater) identity to the nucleic acid sequence of a calcitonin receptor binding partner (e.g., calcitonin, CGRP neuropeptide, or amylin). The mRNA molecule can encode an amino acid sequence differing by no more than 30 (e.g., no more than 30, 20, 10, 5, 4, 3, 2, or 1) amino acids to the amino acid sequence of a calcitonin receptor binding partner (e.g., calcitonin, CGRP neuropeptide, or amylin). The mRNA molecule can have a sequence encoding a fragment of a calcitonin receptor binding partner (e.g., calcitonin, CGRP neuropeptide, or amylin). For example, the fragment includes 10-20, 20-40, 40-60, 60-80, 80-100, 100-120, 120-140, 140-160, 160-180, 180-200, 200-250, 250-300, 300-400, 400-500, 500-600, or more amino acids in length. In embodiments, the fragment is a functional fragment, e.g., having at least 20%, e.g., at least 20%, 30%, 40%, 50%, 60%, 70%, 80%, 90%, or greater, of an activity of a full length calcitonin receptor binding partner (e.g., calcitonin, CGRP neuropeptide, or amylin). In embodiments, the mRNA molecule increases the level and/or activity or function of or encodes a calcitonin receptor binding partner (e.g., calcitonin, CGRP neuropeptide, or amylin).

The synthetic mRNA molecule can be modified, e.g., chemically. The mRNA molecule can be chemically synthesized or transcribed in vitro. The mRNA molecule can be disposed on a plasmid, e.g., a viral vector, bacterial vector, or eukaryotic expression vector. In some examples, the mRNA molecule can be delivered to cells by transfection, electroporation, or transduction (e.g., adenoviral or lentiviral transduction).

In some embodiments, the modified RNA encoding a calcitonin receptor binding partner (e.g., calcitonin, CGRP neuropeptide, or amylin), or another gene of interest described herein has modified nucleosides or nucleotides. Such modifications are known and are described, e.g., in WO 2012/019168. Additional modifications are described, e.g., in WO2015038892; WO2015038892; WO2015089511; WO2015196130; WO2015196118 and WO2015196128A2.

In some embodiments, the modified RNA encoding a polypeptide of interest described herein has one or more terminal modifications, e.g., a 5'Cap structure and/or a poly-A tail (e.g., of between 100-200 nucleotides in length). The 5' cap structure may be selected from the group consisting of CapO, CapI, ARCA, inosine, NI-methyl-guanosine, 2'fluoro-guanosine, 7-deaza-guanosine, 8-oxo-guanosine, 2-amino-guanosine, LNA-guanosine, and 2-azido-guanosine. In some cases, the modified RNAs also contain a 5' UTR including at least one Kozak sequence, and a 3' UTR. Such modifications are known and are described, e.g., in WO2012135805 and WO2013052523. Additional terminal modifications are described, e.g., in WO2014164253 and WO2016011306. WO2012045075 and WO2014093924.

Chimeric enzymes for synthesizing capped RNA molecules (e.g., modified mRNA) which may include at least one chemical modification are described in WO2014028429.

In some embodiments, a modified mRNA may be cyclized, or concatemerized, to generate a translation competent molecule to assist interactions between poly-A binding proteins and 5'-end binding proteins. The mechanism of cyclization or concatemerization may occur through at least 3 different routes: 1) chemical, 2) enzymatic, and 3) ribozyme catalyzed. The newly formed 5'-/3'-linkage may be intramolecular or intermolecular. Such modifications are described, e.g., in WO2013151736.

Methods of making and purifying modified RNAs are known and disclosed in the art. For example, modified RNAs are made using only in vitro transcription (IVT) enzymatic synthesis. Methods of making IVT polynucleotides are known in the art and are described in WO2013151666, WO2013151668, WO2013151663, WO2013151669, WO2013151670, WO2013151664, WO2013151665, WO2013151671, WO2013151672, WO2013151667 and WO2013151736.S Methods of purification include purifying an RNA transcript including a polyA tail by contacting the sample with a surface linked to a plurality of thymidines or derivatives thereof and/or a plurality of uracils or derivatives thereof (polyT/U) under conditions such that the RNA transcript binds to the surface and eluting the purified RNA transcript from the surface (WO2014152031); using ion (e.g., anion) exchange chromatography that allows for separation of longer RNAs up to 10,000 nucleotides in length via a scalable method (WO2014144767); and subjecting a modified mRNA sample to DNAse treatment (WO2014152030).

Formulations of modified RNAs are known and are described, e.g., in WO2013090648. For example, the formulation may be, but is not limited to, nanoparticles, poly (lactic-co-glycolic acid) (PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof.

Modified RNAs encoding polypeptides in the fields of human disease, antibodies, viruses, and a variety of in vivo settings are known and are disclosed in for example, Table 6 of International Publication Nos. WO2013151666, WO2013151668, WO2013151663, WO2013151669, WO2013151670, WO2013151664, WO2013151665, and WO2013151736; Tables 6 and 7 of International Publication No. WO2013151672; Tables 6, 178 and 179 of International Publication No. WO2013151671; Tables 6, 185 and 186 of International Publication No. WO2013151667. Any of the foregoing may be synthesized as an IVT polynucleotide, chimeric polynucleotide or a circular polynucleotide, and each may include one or more modified nucleotides or terminal modifications.

Viral Vectors

The calcitonin receptor activator can be delivered by a viral vector (e.g., a viral vector expressing a calcitonin receptor activator). Viral vectors can be used to express a transgene encoding a soluble calcitonin receptor binding partner or a fragment thereof (e.g., calcitonin, CGRP neuropeptide, or amylin). A viral vector may be administered to a cell or to a subject (e.g., a human subject or animal model) to increase expression of a soluble calcitonin receptor binding partner or a fragment thereof (e.g., calcitonin, CGRP neuropeptide, or amylin). Viral vectors can also be used to express a neurotoxin from Table 8. A viral vector expressing a neurotoxin from Table 8 can be administered to a cell or to a subject (e.g., a human subject or animal model) to decrease or block neurotransmission. Viral vectors can be directly administered (e.g., injected) to a lymph node, lymphoid organ, gut, spleen, skin, airway, wound, or site of inflammation to treat inflammatory or autoimmune disease or condition.

Viral genomes provide a rich source of vectors that can be used for the efficient delivery of exogenous genes into a mammalian cell. Viral genomes are particularly useful vectors for gene delivery because the polynucleotides contained within such genomes are typically incorporated into the nuclear genome of a mammalian cell by generalized or specialized transduction. These processes occur as part of the natural viral replication cycle, and do not require added proteins or reagents in order to induce gene integration. Examples of viral vectors include a retrovirus (e.g., Retroviridae family viral vector), adenovirus (e.g., Ad5, Ad26, Ad34, Ad35, and Ad48), parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses, such as picornavirus and alphavirus, and double stranded DNA viruses including adenovirus, herpesvirus (e.g., Herpes Simplex virus types 1 and 2, Epstein-Barr virus, cytomegalovirus, replication deficient herpes virus), and poxvirus (e.g., vaccinia, modified vaccinia Ankara (MVA), fowlpox and canarypox). Other viruses include Norwalk virus, togavirus, flavivirus, reoviruses, papovavirus, hepadnavirus, human papilloma virus, human foamy virus, and hepatitis virus, for example. Examples of retroviruses include: avian leukosis-sarcoma, avian C-type viruses, mammalian C-type, B-type viruses, D-type viruses, oncoretroviruses, HTLV-BLV group, lentivirus, alpharetrovirus, gammaretrovirus, spumavirus (Coffin, J. M., Retroviridae: The viruses and their replication, Virology (Third Edition) Lippincott-Raven, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in U.S. Pat. No. 5,801,030, the teachings of which are incorporated herein by reference.

Cell-Based Therapies

A calcitonin receptor activator described herein can be administered to a cell in vitro (e.g., an immune cell), which can subsequently be administered to a subject (e.g., a human subject or animal model). The calcitonin receptor activator can be administered to the cell to effect an immune response (e.g., migration, proliferation, recruitment, lymph node homing, lymph node egress, differentiation, activation, polarization, cytokine production, degranulation, maturation, antibody-dependent cell-mediated cytotoxicity (ADCC), antibody-dependent cellular phagocytosis (ADCP), antigen presentation, or calcitonin receptor expression) as described herein. Once the immune response is elicited, the cell can be administered to a subject (e.g., injected) to treat an inflammatory or autoimmune or disease or condition, or infection. The immune cell can be locally administered (e.g., administered to a lymph node or secondary or tertiary lymphoid organ, the spleen, barrier tissue, the skin, gut, an airway, a wound, a mucosal surface, or a site of inflammation or infection).

A calcitonin receptor activator can also be administered to a cell in vitro (e.g., an immune cell, e.g., a macrophage) to alter gene expression in the cell. The calcitonin receptor activator can increase the expression of calcitonin receptor in an immune cell (e.g., a macrophage). The calcitonin receptor activator can be a polypeptide or nucleic acid (e.g., mRNA) described above. The calcitonin receptor activator can be an exogenous gene encoded by a plasmid that is introduced into the cell using standard methods (e.g., calcium phosphate precipitation, electroporation, microinjection, infection, lipofection, impalefection, laserfection, or magnetofection). The calcitonin receptor activator can be a viral vector (e.g., a viral vector expressing a calcitonin receptor activator) that is introduced to the cell using standard transduction methods. The plasmid or vector can also contain a reporter construct (e.g., a fluorescent reporter) that can be used to confirm expression of the transgene by the immune cell. After the immune cell has been contacted with a calcitonin receptor activator to increase gene expression, the cell can be administered to a subject (e.g., injected) to treat an inflammatory or autoimmune or disease or condition, or infection. The immune cell can be locally administered (e.g., administered to a lymph node or secondary or tertiary lymphoid organ, the spleen, barrier tissue, the skin, gut, an airway, a wound, a mucosal surface, or a site of inflammation or infection).

The cell can be administered to a subject immediately after being contacted with a calcitonin receptor activator (e.g., within 5, 10, 15, 30, 45, or 60 minutes of being contacted with a calcitonin receptor activator), or 6 hours, 12 hours, 24 hours, 2 days, 3, days, 4 days, 5, days, 6 days, 7 days or more after being contacted with a calcitonin receptor activator. The method can include an additional step of evaluating the immune cell for an immune cell activity (e.g., migration, proliferation, recruitment, lymph node homing, lymph node egress, differentiation, activation, polarization, cytokine production, degranulation, maturation, ADCC, ADCP, or antigen presentation) or modulation of gene expression after contact with a calcitonin receptor activator and before administration to a subject.

Blood Brain Barrier Permeability

In some embodiments, the calcitonin receptor activators for use in the present invention are agents that are not capable of crossing, or that do not cross, the blood brain barrier (BBB) of a mammal, e.g., an experimental rodent (e.g., mouse or rat), dog, pig, non-human primate, or a human. The BBB is a highly selective semipermeable membrane barrier that separates the circulating blood from the brain extracellular fluid (e.g., cerebrospinal fluid) in the central nervous system (CNS). The BBB is made up of high-density endothelial cells, which are connected by tight junctions. These cells prevent most molecular compounds in the bloodstream (e.g., large molecules and hydrophilic molecules) from entering the brain. Water, some gases (e.g., oxygen and carbon dioxide), and lipid-soluble molecules (e.g., hydrophobic molecules, such as steroid hormones) can cross the BBB by passive diffusion. Molecules that are needed for neural function, such as glucose and amino acids, are actively transported across the BBB.

A number of approaches can be used to render an agent BBB impermeable. These methods include modifications to increase an agent's size, polarity, or flexibility or reduce its lipophilicity, targeting approaches to direct an agent to another part of the body and away from the brain, and packaging approaches to deliver an agent in a form that does not freely diffuse across the BBB. These approaches can be used to render a BBB permeable calcitonin receptor activator impermeable, and they can also be used to improve the properties (e.g., cell-specific targeting) of a calcitonin receptor activator that does not cross the BBB. The methods that can be used to render an agent BBB impermeable are discussed in greater detail herein below.

Formulation of BBB-Permeable Agents for Enhanced Cell Targeting

One approach that can be used to render a calcitonin receptor activator BBB impermeable is to conjugate the agent to a targeting moiety that directs it somewhere other than the brain. The targeting moiety can be an antibody for a receptor expressed by the target cell (e.g., N-Acetylgalactosamine for liver transport; DGCR2, GBF1, GPR44 or SerpinB10 for pancreas transport; Secretoglobin, family 1A, member 1 for lung transport). The targeting moiety can also be a ligand of any receptor or other molecular identifier expressed on the target cell in the periphery. These targeting moieties can direct the calcitonin receptor activator of interest to its corresponding target cell, and can also prevent BBB crossing by directing the agent away from the BBB and increasing the size of the calcitonin receptor activator via conjugation of the targeting moiety.

Calcitonin receptor activators can also be rendered BBB impermeable through formulation in a particulate delivery system (e.g., a nanoparticle, liposome, or microparticle), such that the agent is not freely diffusible in blood and cannot cross the BBB. The particulate formulation used can be chosen based on the desired localization of the calcitonin receptor activator (e.g., a lymph node, lymphoid organ, or site of inflammation), as particles of different sizes accumulate in different locations. For example, nanoparticles with a diameter of 45 nm or less enter the lymph node, while 100 nm nanoparticles exhibit poor lymph node trafficking. Some examples of the link between particle size and localization in vivo are described in Reddy et al., J Controlled Release 112:26 2006, and Reddy et al., Nature Biotechnology 25:1159 2007.

Calcitonin receptor activators can be tested after the addition of a targeting moiety or after formulation in a particulate delivery system to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A calcitonin receptor activator that exhibits BBB impermeability can be used in the methods described herein.

Modification of Existing Compounds to Render them BBB Impermeable

There are multiple parameters that have been empirically derived in the field of medicinal chemistry to predict whether a compound will cross the BBB. The most common numeric value for describing permeability across the BBB is the log BB, defined as the logarithmic ratio of the concentration of a compound in the brain and in the blood. Empirical rules of thumb have been developed to predict BBB permeability, including rules regarding molecular size, polar surface area, sum of oxygen and nitrogen atoms, lipophilicity (e.g., partition coefficient between apolar solvent and water), "lipoaffinity", molecular flexibility, and number of rotable bonds (summarized in Muehlbacher et al., J Comput Aided Mol Des. 25: 1095 2011; and Geldenhuys et al., Ther Deliv. 6: 961 2015). Some preferred limits on various parameters for BBB permeability are listed in Table 1 of Ghose et al., ACS Chem Neurosci. 3: 50 2012, which is incorporated herein by reference. Based on the parameters shown in the table, one of skill in the art could modify an existing calcitonin receptor activator to render it BBB impermeable.

One method of modifying a calcitonin receptor activator to prevent BBB crossing is to add a molecular adduct that does not affect the target binding specificity, kinetics, or thermodynamics of the agent. Molecular adducts that can be used to render an agent BBB impermeable include polyethylene glycol (PEG), a carbohydrate monomer or polymer, a dendrimer, a polypeptide, a charged ion, a hydrophilic group, deuterium, and fluorine. Calcitonin receptor activators can be tested after the addition of one or more molecular adducts or after any other properties are altered to determine whether or not they cross the BBB. Models for assessing BBB permeability include in vitro models (e.g., monolayer models, co-culture models, dynamic models, multi-fluidic models, isolated brain microvessels), in vivo models, and computational models as described in He et al., Stroke 45:2514 2014; Bickel, NeuroRx 2:15 2005; and Wang et al., Int J Pharm 288:349 2005. A calcitonin receptor activator that exhibits BBB impermeability can be used in the methods described herein.

Screening for or Development of BBB Impermeable Agents

Another option for developing BBB impermeable agents is to find or develop new agents that do not cross the BBB. One method for finding new BBB impermeable agents is to screen for compounds that are BBB impermeable. Compound screening can be performed using in vitro models (e.g., monolayer models, co-culture models, dynamic models, multi-fluidic models, isolated brain microvessels), in vivo models, and computational models, as described in He et al., Stroke 45:2514 2014; Bickel, NeuroRx 2:15 2005; Wang et al., Int J Pharm 288:349 2005, and Czupalla et al., Methods Mol Biol 1135:415 2014. For example, the ability of a molecule to cross the blood brain barrier can be determined in vitro using a transwell BBB assay in which microvascular endothelial cells and pericytes are co-cultured separated by a thin macroporous membrane, see e.g., Naik et al., J Pharm Sci 101:1337 2012 and Hanada et al., Int J Mol Sci 15:1812 2014; or in vivo by tracking the brain uptake of the target molecule by histology or radio-detection. Compounds would be deemed appropriate for use as calcitonin receptor activators in the methods described herein if they do not display BBB permeability in the aforementioned models.

Modulation of Immune Cells

The methods described herein can be used to modulate an immune response in a subject or cell by administering to a subject or cell a calcitonin receptor activator in a dose (e.g., an effective amount) and for a time sufficient to modulate the immune response. These methods can be used to treat a subject in need of modulating an immune response, e.g., a subject with an inflammatory condition, an autoimmune disease or condition, or a chronic infection. One way to modulate an immune response is to modulate an immune cell activity. This modulation can occur in vivo (e.g., in a human subject or animal model) or in vitro (e.g., in acutely isolated or cultured cells, such as human cells from a patient, repository, or cell line, or rodent cells). The types of cells that can be modulated include T cells (e.g., peripheral T cells, cytotoxic T cells/CD8+ T cells, T helper cells/CD4+ T cells, memory T cells, regulatory T cells/Tregs, natural killer T cells/NKTs, mucosal associated invariant T cells, and gamma delta T cells), B cells (e.g., memory B cells, plasmablasts, plasma cells, follicular B cells/B-2 cells, marginal zone B cells, B-1 cells, regulatory B cells/Bregs), dendritic cells (e.g., myeloid DCs/conventional DCs, plasmacytoid DCs, or follicular DCs), granulocytes (e.g., eosinophils, mast cells, neutrophils, and basophils), monocytes, macrophages (e.g., peripheral macrophages or tissue resident macrophages), myeloid-derived suppressor cells, natural killer (NK) cells, innate lymphoid cells (e.g., ILC1s, ILC2s, and ILC3s), thymocytes, and megakaryocytes.

The immune cell activities that can be modulated by administering to a subject or contacting a cell with an effective amount of a calcitonin receptor activator described herein include activation (e.g., macrophage, T cell, NK cell, ILC, B cell, dendritic cell, neutrophil, eosinophil, or basophil activation), phagocytosis (e.g., macrophage, neutrophil, monocyte, mast cell, B cell, eosinophil, or dendritic cell phagocytosis), antibody-dependent cellular phagocytosis (e.g., ADCP by monocytes, macrophages, neutrophils, or dendritic cells), antibody-dependent cellular cytotoxicity (e.g., ADCC by NK cells, ILCs, monocytes, macrophages, neutrophils, eosinophils, dendritic cells, or T cells), polarization (e.g., macrophage polarization toward an M1 or M2 phenotype or T cell polarization), proliferation (e.g., proliferation of B cells, T cells, monocytes, macrophages, dendritic cells, NK cells, ILCs, mast cells, neutrophils, eosinophils, or basophils), lymph node homing (e.g., lymph node homing of T cells, B cells, dendritic cells, or macrophages), lymph node egress (e.g., lymph node egress of T cells, B cells, dendritic cells, or macrophages), recruitment (e.g., recruitment of B cells, T cells, monocytes, macrophages, dendritic cells, NK cells, ILCs, mast cells, neutrophils, eosinophils, or basophils), migration (e.g., migration of B cells, T cells, monocytes, macrophages, dendritic cells, NK cells, ILCs, mast cells, neutrophils, eosinophils, or basophils), differentiation (e.g., regulatory T cell differentiation), immune cell cytokine production, antigen presentation (e.g., dendritic cell, macrophage, and B cell antigen presentation), maturation (e.g., dendritic cell maturation), and degranulation (e.g., mast cell, NK cell, ILCs, cytotoxic T cell, neutrophil, eosinophil, or basophil degranulation). Innervation of lymph nodes or lymphoid organs, development of HEVs), and development of TLOs can also be modulated using the methods described herein. Modulation can increase or decrease these activities, depending on the calcitonin receptor activator used to contact the cell or treat a subject.

In some embodiments, an effective amount of a calcitonin receptor activator is an amount sufficient to modulate (e.g., increase or decrease) one or more (e.g., 2 or more, 3 or more, 4 or more) of the following immune cell activities in the subject or cell: T cell polarization; T cell activation; dendritic cell activation; neutrophil activation; eosinophil activation; basophil activation; T cell proliferation; B cell proliferation; T cell proliferation; monocyte proliferation; macrophage proliferation; dendritic cell proliferation; NK cell proliferation; ILC proliferation, mast cell proliferation; neutrophil proliferation; eosinophil proliferation; basophil proliferation; cytotoxic T cell activation; circulating monocytes; peripheral blood hematopoietic stem cells; macrophage polarization; macrophage phagocytosis; macrophage ADCP, neutrophil phagocytosis; monocyte phagocytosis; mast cell phagocytosis; B cell phagocytosis; eosinophil phagocytosis; dendritic cell phagocytosis; macrophage activation; antigen presentation (e.g., dendritic cell, macrophage, and B cell antigen presentation); antigen presenting cell migration (e.g., dendritic cell, macrophage, and B cell migration); lymph node immune cell homing and cell egress (e.g., lymph node homing and egress of T cells, B cells, dendritic cells, or macrophages); NK cell activation; NK cell ADCC, mast cell degranulation; NK cell degranulation; ILC activation, ILC ADCC, ILC degranulation, cytotoxic T cell degranulation; neutrophil degranulation; eosinophil degranulation; basophil degranulation; neutrophil recruitment; eosinophil recruitment; NKT cell activation; B cell activation; regulatory T cell differentiation; dendritic cell maturation; development of HEVs; development of TLOs; or lymph node or secondary lymphoid organ innervation. In certain embodiments, the immune response (e.g., an immune cell activity listed herein) is increased or decreased in the subject or cell at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the immune response is increased or decreased in the subject or cell between 5-20%, between 5-50%, between 10-50%, between 20-80%, between 20-70%, between 50-200%, between 100%-500%.

After a calcitonin receptor activator is administered to treat a patient or contact a cell, a readout can be used to assess the effect on immune cell activity. Immune cell activity can be assessed by measuring a cytokine or marker associated with a particular immune cell type (e.g., a macrophage), as listed in Table 1 (e.g., performing an assay listed in Table 1 for the cytokine or marker). In certain embodiments, the parameter is increased or decreased in the subject at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the parameter is increased or decreased in the subject between 5-20%, between 5-50%, between 10-50%, between 20-80%, between 20-70%, between 50-200%, between 100%-500%. A calcitonin receptor activator can be administered at a dose (e.g., an effective amount) and for a time sufficient to modulate an immune cell activity described herein below.

After a calcitonin receptor activator is administered to treat a patient or contact a cell, a readout can be used to assess the effect on immune cell migration. Immune cell migration can be assessed by measuring the number of immune cells in a location of interest (e.g., a lymph node or secondary lymphoid organ, or site of inflammation). Immune cell migration can also be assessed by measuring a chemokine, receptor, or marker associated with immune cell migration, as listed in Tables 2 and 3. In certain embodiments, the parameter is increased or decreased in the subject at least 1%, 2%, 5%, 10%, 15%, 20%, 25%, 30%, 35%, 40%, 50%, 60%, 70%, 80%, 100%, 150%, 200%, 300%, 400%, 500% or more, compared to before the administration. In certain embodiments, the parameter is increased or decreased in the subject between 5-20%, between 5-50%, between 10-50%, between 20-80%, between 20-70%, between 50-200%, between 100%-500%. A calcitonin receptor activator can be administered at a dose (e.g., an effective amount) and for a time sufficient to modulate an immune cell migration as described herein below.

A calcitonin receptor activator described herein can affect immune cell migration. Immune cell migration between peripheral tissues, the blood, and the lymphatic system as well as lymphoid organs is essential for the orchestration of productive innate and adaptive immune responses. Immune cell migration is largely regulated by trafficking molecules including integrins, immunoglobulin cell-adhesion molecules (IgSF CAMs), cadherins, selectins, and a family of small cytokines called chemokines (Table 2). Cell adhesion molecules and chemokines regulate immune cell migration by both inducing extravasation from the circulation into peripheral tissues and acting as guidance cues within peripheral tissues themselves. For extravasation to occur, chemokines must act in concert with multiple trafficking molecules including C-type lectins (L-, P-, and E-selectin), multiple integrins, and cell adhesion molecules (ICAM-1, VCAM-1 and MAdCAM-1) to enable a multi-step cascade of immune cell capturing, rolling, arrest, and transmigration via the blood endothelial barrier (Table 3). Some trafficking molecules are constitutively expressed and manage the migration of immune cells during homeostasis, while others are specifically upregulated by inflammatory processes such as infection and autoimmunity.

The expression of trafficking molecules important for extravasation is mainly regulated on specialized blood vessels called HEVs, which are the entry portals from the circulation into the periphery and are usually present in secondary lymphoid organs (SLOs) and chronically inflamed tissue. Chronically inflamed tissues often develop lymphoid-like structures called TLOs that contain structures resembling SLOs including HEVs, lymphoid stromal cells, and confined compartments of T and B lymphocytes. As they can act as major gateways for immune cell migration into peripheral tissues, TLOs have been shown to be important in the pathogenesis of autoimmune disorders.

Once within peripheral tissues, four modes of immune cell migration have been observed: 1) chemokinesis: migration driven by soluble chemokines, without concentration gradients to provide directional bias, 2) haptokinesis: migration along surfaces presenting immobilized ligands such as chemokines or integrins, without concentration gradients to provide directional bias, 3) chemotaxis: directional migration driven by concentration gradients of soluble chemokines, and 4) haptotaxis: directional migration along surfaces presenting gradients of immobilized ligands such as chemokines or integrins. The response of immune cells to trafficking molecules present on the endothelium depends on the composition, expression, and/or functional activity of their cognate receptors, which in turn depends on activation state and immune cell subtype.

Innate immune cells generally migrate toward inflammation-induced trafficking molecules in the periphery. In contrast, naïve T and B cells constantly re-circulate between the blood and secondary lymphoid organs to screen for their cognate antigen presented by activated dendritic cells (DCs) or fibroblastic reticular cells (FRCs), respectively. If activated by recognition of their cognate antigen and appropriate co-stimulation within SLOs, both cell types undergo a series of complex maturation steps, including differentiation and proliferation, ultimately leading to effector and memory immune cell phenotypes. To reach their peripheral target sites, certain effector and memory T and B cell subsets egress from SLOs to the blood circulation via efferent lymphatics. In order to do so, they migrate toward a Sphingosine-1-phosphate (S1P) gradient sensed using their Sphingosine-1-phosphate receptor 1 ($S1P_1$ or S1PR1). For successful egress into efferent lymphatics, immune cells need to overcome SLO retention signals through the CCR7/CCL21 axis or through CD69-mediated downregulation of $S1P_1$.

Finally, certain immune cell subsets, for example mature dendritic cells (DCs) and memory T cells, migrate from peripheral tissues into SLOs via afferent lymphatics. To exit from peripheral tissues and enter afferent lymphatics, immune cells again largely depend on the CCR7/CCL21 and $S1P_1$/S1P axis. Specifically, immune cells need to overcome retention signals delivered via the CCR7/CCL21 axis, and migrate toward an S1P gradient established by the lymphatic endothelial cells using $S1P_1$. The selective action of trafficking molecules on distinct immune cell subsets as well as the distinct spatial and temporal expression patterns of both the ligands and receptors are crucial for the fine-tuning of immune responses during homeostasis and disease.

Aberrant immune cell migration is observed in multiple immune-related pathologies. Immune cell adhesion deficiencies, caused by molecular defects in integrin expression, fucosylation of selectin ligands, or inside-out activation of integrins on leukocytes and platelets, lead to impaired immune cell migration into peripheral tissues. This results in leukocytosis and in increased susceptibility to recurrent bacterial and fungal infections, which can be difficult to treat and potentially life-threatening. Alternatively, exaggerated migration of specific immune cell subsets into specific peripheral tissues is associated with a multitude of pathologies. For example, excessive neutrophil accumulation in peripheral tissues contributes to the development of ischemia-reperfusion injury, such as that observed during acute myocardial infarction, stroke, shock and acute respiratory distress syndrome. Excessive Th1 inflammation characterized by tissue infiltration of interferon-gamma secreting effector T cells and activated macrophages is associated with atherosclerosis, allograft rejection, hepatitis, and multiple autoimmune diseases including multiple sclerosis, rheumatoid arthritis, psoriasis, Crohn's disease, type 1 diabetes and lupus erythematodes. Excessive Th2 inflammation characterized by tissue infiltration of IL-4, IL-5, and IL-13 secreting Th2 cells, eosinophils and mast cells is associated with asthma, food allergies and atopic dermatitis.

In some embodiments, a calcitonin receptor activator described herein increases macrophage lymph node homing, increases macrophage calcitonin receptor expression (e.g., expression of CALCR and/or RAMP1), and/or improves organ function. In some embodiments, a calcitonin receptor activator described herein decreases one or more of macrophage migration, macrophage proliferation, macrophage recruitment, macrophage lymph node egress, macrophage differentiation, macrophage activation, macrophage polarization, macrophage cytokine production, macrophage maturation, macrophage antigen presentation, macrophage ADCC, or macrophage ADCP. In some embodiments, the cytokine is a pro-inflammatory cytokine (e.g., IL6 and/or IFNγ). In some embodiments, a calcitonin receptor activator described herein decreases inflammation, auto-antibody levels, viral load, or the rate or number of relapses or flare-ups. In some embodiments, the macrophage is an M1 macrophage. In some embodiments, the macrophage is an M2 macrophage.

Immune Effects

A variety of in vitro and in vivo assays can be used to determine how a calcitonin receptor activator affects an immune cell activity. The effect of a calcitonin receptor activator on T cell polarization in a subject can be assessed by evaluation of cell surface markers on T cells obtained from the subject. A blood sample, lymph node biopsy (e.g., a primary, secondary, or tertiary lymph node biopsy), splenic biopsy, or tissue (e.g., a barrier tissue, skin, gut tissue, airway tissue, or wound tissue) sample can be collected from a subject and T cells from the sample evaluated for one or more (e.g., 2, 3, or 4 or more) Th1-specific markers: T-bet, IL-12R, STAT4, or chemokine receptors CCR5, CXCR6, and CXCR3; or Th2-specific markers: CCR3, CXCR4, or IL-4Rα. T cell polarization can also be assessed using the same methods in an in vivo animal model. This assay can also be performed by adding a calcitonin receptor activator to T cells in vitro (e.g., T cells obtained from a subject, animal model, repository, or commercial source) and measuring the aforementioned markers to evaluate T cell polarization. These markers can be assessed using flow cytometry, immunohistochemistry, in situ hybridization, and other assays that allow for measurement of cellular markers. Comparing results from before and after administration of a calcitonin receptor activator can be used to determine its effect.

The effect of a calcitonin receptor activator on T cell activation in a subject can be assessed by evaluation of cellular markers on T cells obtained from the subject. A blood sample, lymph node biopsy (e.g., a primary, secondary, or tertiary lymph node biopsy), splenic biopsy, or tissue (e.g., a barrier tissue, skin, gut tissue, airway tissue, or wound tissue) sample can be collected from a subject and T cells from the sample evaluated for one or more (e.g., 2, 3, 4 or more) activation markers: CD25, CD71, CD26, CD27, CD28, CD30, CD154, CD40L, CD134, CD69, CD62L or CD44. T cell activation can also be assessed using the same methods in an in vivo animal model. This assay can also be performed by adding a calcitonin receptor activator to T cells in vitro (e.g., T cells obtained from a subject, animal model, repository, or commercial source) and measuring the aforementioned markers to evaluate T cell activation. Similar approaches can be used to assess the effect of a calcitonin receptor activator on activation of other immune cells, such as eosinophils (markers: CD35, CD11b, CD66, CD69 and CD81), dendritic cells (makers: IL-8, MHC class II, CD40, CD80, CD83, and CD86), basophils (CD63, CD13, CD4, and CD203c), ILCs (markers: CD69), and neutrophils (CD11b, CD35, CD66b and CD63). These markers can be assessed using flow cytometry, immunohistochemistry, in situ hybridization, and other assays that allow for measurement of cellular markers. Comparing results from before and after administration of a calcitonin receptor activator can be used to determine its effect.

The effect of a calcitonin receptor activator on immune cell activation can also be assessed through measurement of secreted cytokines and chemokines. An activated immune cell (e.g., T cell, B cell, macrophage, monocyte, dendritic cell, eosinophil, basophil, mast cell, NK cell, ILC, or neutrophil) can produce pro-inflammatory cytokines and chemokines (e.g., IL-1β, IL-5, IL-6, IL-8, IL-10, IL-12, IL-13, IL-18, TNFα, and IFN-γ). Activation can be assessed by measuring cytokine levels in a blood sample, lymph node biopsy, or tissue sample from a human subject or animal model, with higher levels of pro-inflammatory cytokines following treatment with a calcitonin receptor activator indicating increased activation, and lower levels indicating decreased activation. Activation can also be assessed in vitro by measuring cytokines secreted into the media by cultured cells. Cytokines can be measured using ELISA, western blot analysis, and other approaches for quantifying secreted proteins. Comparing results from before and after administration of a calcitonin receptor activator can be used to determine its effect.

The effect of a calcitonin receptor activator on T cell proliferation in a subject can be assessed by evaluation of markers of proliferation in T cells obtained from the subject. A blood sample, lymph node biopsy, or tissue sample can be collected from a subject and T cells from the sample evaluated for Ki67 marker expression. T cell proliferation can also be assessed using the same methods in an in vivo animal model. This assay can also be performed by adding a calcitonin receptor activator to T cells in vitro (e.g., T cells obtained from a subject, animal model, repository, or commercial source) and measuring Ki67 to evaluate T cell proliferation. Assessing whether a calcitonin receptor activator induces T cell proliferation can also be performed by in vivo (e.g., in a human subject or animal model) by collecting blood samples before and after calcitonin receptor activator administration and comparing T cell numbers, and in vitro by quantifying T cell numbers before and after contacting T cells with a calcitonin receptor activator. These approaches can also be used to measure the effect of a calcitonin receptor activator on proliferation of any immune cell (e.g., Tregs, B cells, T cells, macrophages, monocytes, dendritic cells, NK cells, ILCs, mast cells, eosinophils, basophils, and neutrophils). Ki67 can be assessed using flow cytometry, immunohistochemistry, in situ hybridization, and other assays that allow for measurement of nuclear markers. Comparing results from before and after administration of a calcitonin receptor activator can be used to determine its effect.

The effect of a calcitonin receptor activator on cytotoxic T cell activation in a subject can be assessed by evaluation of T cell granule markers in T cells obtained from the subject. A blood sample, lymph node biopsy, or tissue sample can be collected from a subject and T cells from the sample evaluated for granzyme or perforin expression. Cytotoxic T cell activation can also be assessed using the same methods in an in vivo animal model. This assay can also be performed by adding a calcitonin receptor activator to cytotoxic T cells in vitro (e.g., cytotoxic T cells obtained from a subject, animal model, repository, or commercial source) and measuring the aforementioned markers to evaluate T cell proliferation. These markers can be detected in the media from cytotoxic T cell cultures. Techniques including ELISA, western blot analysis can be used to detect granzyme and perforin in conditioned media, flow cytometry, immunohistochemistry, in situ hybridization, and other assays can detect intracellular granzyme and perforin and their synthesis. Comparing results from before and after administration of a calcitonin receptor activator can be used to determine its effect.

The effect of a calcitonin receptor activator on circulating monocytes in a subject can be assessed by evaluation of cell surface markers on primary blood mononuclear cells obtained from the subject. A blood sample, lymph node biopsy, or tissue sample can be collected from a subject and monocytes from the sample evaluated for CD14 and/or CD16 expression. Circulating monocytes can also be assessed using the same methods in an in vivo animal model. This assay can be performed by taking a blood sample before treatment with a calcitonin receptor activator and comparing it to a blood sample taken after treatment. CD14 and CD16 can be detected using flow cytometry, immunohistochemistry, western blot analysis, or any other technique that can measure cell surface protein levels. Comparing results from before and after administration of a calcitonin receptor activator can be used to determine its effect. This assay can be used to detect the number of monocytes in the bloodstream or to determine whether monocytes have adopted a CD14+/CD16+ phenotype, which indicates a pro-inflammatory function.

The effect of a calcitonin receptor activator on peripheral blood hematopoietic stem cells in a subject can be assessed by evaluation of cell surface markers on primary blood mononuclear cells obtained from the subject. A blood sample, lymph node biopsy, or tissue sample can be collected from a subject and stem cells from the sample evaluated for one or more (2, 3 or 4 or more) specific markers: CD34, c-kit, Sca-1, or Thy1.1. Peripheral blood hematopoietic stem cells can also be assessed using the same methods in an in vivo animal model. This assay can be performed by taking a blood sample before treatment with a calcitonin receptor activator and comparing it to a blood sample taken after treatment. The aforementioned markers can be detected using flow cytometry, immunohistochemistry, western blot analysis, or any other technique that can measure cell surface protein levels. Comparing results from before and after administration of a calcitonin receptor activator can be used to determine its effect. This assay can be used to detect the number of stem cells mobilized into the bloodstream or to determine whether treatment induces differentiation into a particular hematopoietic lineage (e.g., decreased CD34 and increased GPA indicates differentiation into red blood cells, decreased CD34 and increased CD14 indicates differentiation into monocytes, decreased CD34 and increased CD11 b or CD68 indicates differentiation into macrophages, decreased CD34 and increased CD42b indicates differentiation into platelets, decreased CD34 and increased CD3 indicates differentiation into T cells, decreased CD34 and increased CD19 indicates differentiation into B cells, decreased CD34 and increased CD25 or CD69 indicates differentiation into activated T cells, decreased CD34 and increased CD1c, CD83, CD141, CD209, or MHC II indicates differentiation into dendritic cells, decreased CD34 and increased CD56 indicates differentiation into NK cells, decreased CD34 and increased CD15 indicates differentiation into neutrophils, decreased CD34 and increased 2D7 antigen, CD123, or CD203c indicates differentiation into basophils, and decreased CD34 and increased CD193, EMR1, or Siglec-8 indicates differentiation into eosinophils.

The effect of a calcitonin receptor activator on macrophage polarization in a subject can be assessed by evaluation of cellular markers in macrophages cells obtained from the subject. A blood sample, lymph node biopsy, or tissue sample can be collected from a subject and macrophages from the sample evaluated for one of more (2, 3 or 4 or more) specific markers. Markers for M1 polarization include IL-12, TNF, IL-1β, IL-6, IL-23, MARCO, MHC-II, CD86, iNOS, CXCL9, and CXCL10. Markers for M2 polarized macrophages include IL-10, IL1-RA, TGFβ, MR, CD163, DC-SIGN, Dectin-1, HO-1, arginase (Arg-1), CCL17, CCL22 and CCL24. Macrophage polarization can also be assessed using the same methods in an in vivo animal model. This assay can also be performed on cultured macrophages obtained from a subject, an animal model, repository, or commercial source to determine how contacting a macrophage with a calcitonin receptor activator affects polarization. The aforementioned markers can be evaluated by comparing measurements obtained before and after administration of a calcitonin receptor activator to a subject, animal model, or cultured cell. Surface markers or intracellular proteins (e.g., MHC-11, CD86, iNOS, CD163, Dectin-1, HO-1, Arg-1, etc.) can be measured using flow cytometry, immunohistochemistry, in situ hybridization, or western blot analysis, and secreted proteins (e.g., IL-12, TNF, IL-1β, IL-10, TGFβ, IL1-RA, chemokines CXC8, CXC9, CCL17, CCL22, and CCL24, etc.) can be measured using the same methods or by ELISA or western blot analysis of culture media or blood samples. Comparing results from before and after administration of a calcitonin receptor activator can be used to determine its effect.

The effect of a calcitonin receptor activator on macrophage phagocytosis in a subject can be assessed by culturing macrophages obtained from the subject with fluorescent beads. A blood sample, lymph node biopsy, or tissue sample can be collected from a subject and macrophages from the sample evaluated for engulfment of fluorescent beads. This assay can also be performed on cultured macrophages obtained from an animal model, repository, or commercial source to determine how contacting a macrophage with a calcitonin receptor activator affects phagocytosis. The same phagocytosis assay can be used to evaluate the effect of a calcitonin receptor activator on phagocytosis in other immune cells (e.g., neutrophils, monocytes, mast cells, B cells, eosinophils, or dendritic cells). Comparing results from before and after administration of a calcitonin receptor activator can be used to determine its effect on phagocytosis.

In some embodiments, phagocytosis is ADCP. ADCP can be assessed using similar methods to those described above by incubating immune cells (e.g., macrophages, neutrophils, monocytes, mast cells, B cells, eosinophils, or dendritic cells) isolated from a blood sample, lymph node biopsy, or tissue sample with fluorescent beads coated with IgG antibodies. In some embodiments, immune cells are incubated with a target cell line that has been pre-coated with antibodies to a surface antigen expressed by the target cell line. ADCP can be evaluated by measuring fluorescence inside the immune cell or quantifying the number of beads or cells engulfed. This assay can also be performed on cultured immune cells obtained from an animal model, repository, or commercial source to determine how contacting an immune cell with a calcitonin receptor activator affects ADCP. The ability of an immune cell to perform ADCP can also be evaluated by assessing expression of certain Fc receptors (e.g., FcγRIIa, FcγRIIIa, and FcγRI). Fc receptor expression can be assessed using flow cytometry, immunohistochemistry, in situ hybridization, or other assays that allow for measurement of cell surface markers. Comparing phagocytosis or Fc receptor expression before and after administration of a calcitonin receptor activator can be used to determine its effect on ACDP. In some embodiments, the calcitonin receptor activator increases ADCP of infectious agents. In some embodiments, the calcitonin receptor activator decreases macrophage ADCP of auto-antibody coated cells (e.g., in autoimmune diseases such as Crohn's disease).

The effect of a calcitonin receptor activator on macrophage activation in a subject can be assessed by evaluation of cell surface markers on macrophages cells obtained from the subject. A blood sample, lymph node biopsy, or tissue sample can be collected from a subject and macrophages from the sample evaluated for one or more (e.g., 1, 2, 3 or 4 or more) specific markers: F4/80, HLA molecules (e.g., MHC-II), CD80, CD68, CD11b, or CD86. Macrophage activation can also be assessed using the same methods in an in vivo animal model. This assay can also be performed by adding a calcitonin receptor activator to macrophages in vitro (e.g., macrophages obtained from a subject, animal model, repository, or commercial source) and measuring the aforementioned markers to evaluate macrophage activation. These markers can be assessed using flow cytometry, immunohistochemistry, in situ hybridization, and other assays that allow for measurement of cell surface markers. As mentioned above, macrophage activation can also be evaluated based on cytokine production (e.g., pro-inflammatory cytokine production) as measured by ELISA and western blot analysis. Comparing results from before and after administration of a calcitonin receptor activator can be used to determine its effect.

The effect of a calcitonin receptor activator on antigen presentation in a subject can be assessed by evaluation of cell surface markers on antigen presenting cells (e.g., dendritic cells, macrophages, and B cells) obtained from the subject. A blood sample, lymph node biopsy, or tissue sample can be collected from a subject and antigen presenting cells (e.g., dendritic cells, macrophages, and B cells) from the sample evaluated for one or more (e.g., 2, 3 or 4 or more) specific markers: CD11c, CD11b, HLA molecules (e.g., MHC-II), CD40, B7, IL-2, CD80 or CD86. Antigen presentation can also be assessed using the same methods in an in vivo animal model. This assay can also be performed by adding a calcitonin receptor activator to antigen presenting cells (e.g., dendritic cells) in vitro (e.g., antigen presenting cells obtained from a subject, animal model, repository, or commercial source) and measuring the aforementioned markers to evaluate antigen presentation. These markers can be assessed using flow cytometry, immunohistochemistry, in situ hybridization, and other assays that allow for measurement of cell surface markers. Comparing results from before and after administration of a calcitonin receptor activator can be used to determine its effect.

The effect of a calcitonin receptor activator on antigen presenting cell migration in a subject can be assessed by evaluation of cell surface markers on antigen presenting cells (e.g., dendritic cells, B cells, and macrophages) obtained from the subject. A blood sample, lymph node biopsy, or tissue sample can be collected from a subject and antigen presenting cells (e.g., dendritic cells, B cells, and macrophages) from the sample evaluated for CCR7 expression. Antigen presenting cell migration can also be assessed using the same methods in an in vivo animal model. This assay can also be performed by adding a calcitonin receptor activator to antigen presenting cells (e.g., dendritic cells, B cells, and macrophages) in vitro (e.g., antigen presenting cells obtained from a subject, animal model, repository, or commercial source) and measuring CCR7 to evaluate antigen presenting cell migration. CCR7 can be assessed using flow cytometry, immunohistochemistry, in situ hybridization, and other assays that allow for measurement of cell surface markers. Comparing results from before and after administration of a calcitonin receptor activator can be used to determine its effect.

The effect of a calcitonin receptor activator on lymph node immune cell homing and cell egress in a subject can be assessed by evaluation of cell surface markers on T or B cells obtained from the subject. A blood sample, lymph node biopsy, or tissue sample can be collected from a subject and T or B cells from the sample evaluated for one or more specific markers: CCR7 or S1PR1. Lymph node immune cell homing and cell egress can also be assessed using the same methods in an in vivo animal model. This assay can also be performed by adding a calcitonin receptor activator to T or B cells in vitro (e.g., T or B cells obtained from a subject, animal model, repository, or commercial source) and measuring the aforementioned markers to evaluate T or B cell lymph node homing. These markers can also be used to assess lymph node homing and cell egress of dendritic cells and macrophages. CCR7 and S1PR1 can be assessed using flow cytometry, immunohistochemistry, in situ hybridization, and other assays that allow for measurement of cell surface markers. If using an animal model, lymph nodes or sites of inflammation can be imaged in vivo (e.g., using a mouse that expresses fluorescently labeled T or B cells) or after biopsy to determine whether T or B cell numbers change as a result of administration of a calcitonin receptor activator. Comparing results from before and after administration of a calcitonin receptor activator can be used to determine its effect.

In some embodiments, a calcitonin receptor activator increases homing or decreases egress of naïve T cells into or out of secondary lymphoid organs prior to antigen challenge (e.g., prior to administration of a vaccine) to generate a better antigen-specific response. In some embodiments, a calcitonin receptor activator decreases homing or increases egress of inflammatory immune cells (e.g., neutrophils) into or out of peripheral tissues during acute infection or injury to prevent conditions such as ischemia-reperfusion disorders. In some embodiments, a calcitonin receptor activator decreases homing or increases egress of effector immune subsets into or out of peripheral tissues to avoid inflammation-induced tissue damage in autoimmune diseases.

The effect of a calcitonin receptor activator on NK cell activation in a subject can be assessed by evaluation of cell surface markers on NK cells obtained from the subject. A blood sample, lymph node biopsy, or tissue sample can be collected from a subject and NK cells from the sample evaluated for one or more (e.g., 2, 3 or 4 or more) specific markers: CD117, NKp46, CD94, CD56, CD16, KIR, CD69, HLA-DR, CD38, KLRG1, and TIA-1. NK cell activation can also be assessed using the same methods in an in vivo animal model. This assay can also be performed by adding a calcitonin receptor activator to NK cells in vitro (e.g., NK cells obtained from a subject, animal model, repository, or commercial source) and measuring the aforementioned markers to evaluate NK cell activation. The effect of a calcitonin receptor activator can be determined by comparing results from before and after calcitonin receptor activator administration.

In some embodiments, activated NK cells have increased lytic function or are cytotoxic (e.g., capable of performing ADCC). The effect of a calcitonin receptor activator on ADCC can be assessed by incubating immune cells capable of ADCC (e.g., NK cells, monocytes, macrophages, neutrophils, eosinophils, dendritic cells, or T cells) with a target cell line that has been pre-coated with antibodies to a surface antigen expressed by the target cell line. ADCC can be assessed by measuring the number of surviving target cells with a fluorescent viability stain or by measuring the secretion of cytolytic granules (e.g., perforin, granzymes, or other cytolytic proteins released from immune cells). Immune cells can be collected from a blood sample, lymph node biopsy, or tissue sample from a human subject or animal model treated with a calcitonin receptor activator. This assay can also be performed by adding a calcitonin receptor activator to immune cells in vitro (e.g., immune cells obtained from a subject, animal model, repository, or commercial source). The effect of a calcitonin receptor activator on ADCC can be determined by comparing results from before and after calcitonin receptor activator administration. In some embodiments, the calcitonin receptor activator decreases NK cell ADCC of auto-antibody coated cells (e.g., to treat autoimmune disease). In some embodiments, the calcitonin receptor activator increases NK cell ADCC of antibody-opsonized infectious agents.

The effect of a calcitonin receptor activator on ILC activation in a subject can be assessed by evaluation of cell surface markers on ILCs obtained from the subject. A blood sample, lymph node biopsy, or tissue sample can be collected from a subject and ILCs from the sample evaluated for one or more (e.g., 2, 3 or 4 or more) specific markers: NKp46, CD69, T-bet, ROR$\alpha$, GATA3, and ROR$\gamma$t. ILC activation can also be assessed using the same methods in an in vivo animal model. This assay can also be performed by adding a calcitonin receptor activator to ILCs in vitro (e.g., ILCs obtained from a subject, animal model, repository, or commercial source) and measuring the aforementioned markers to evaluate ILC activation. The effect of a calcitonin receptor activator can be determined by comparing results from before and after calcitonin receptor activator administration.

In some embodiments, activated ILCs have increased lytic function or are cytotoxic (e.g., capable of performing ADCC). The effect of a calcitonin receptor activator on ADCC can be assessed by incubating immune cells capable of ADCC (e.g., ILCs, monocytes, macrophages, neutrophils, eosinophils, dendritic cells, or T cells) with a target cell line that has been pre-coated with antibodies to a surface antigen expressed by the target cell line. ADCC can be assessed by measuring the number of surviving target cells with a fluorescent viability stain or by measuring the secretion of cytolytic granules (e.g., perforin, granzymes, or other cytolytic proteins released from immune cells). Immune cells can be collected from a blood sample, lymph node biopsy, or tissue sample from a human subject or animal model treated with a calcitonin receptor activator. This assay can also be performed by adding a calcitonin receptor activator to immune cells in vitro (e.g., immune cells obtained from a subject, animal model, repository, or commercial source). The effect of a calcitonin receptor activator on ADCC can be determined by comparing results from before and after calcitonin receptor activator administration. In some embodiments, the calcitonin receptor activator decreases ILC ADCC of auto-antibody coated cells (e.g., to treat autoimmune disease). In some embodiments, the calcitonin receptor activator increases ILC ADCC of antibody-opsonized infectious agents.

The effect of a calcitonin receptor activator on mast cell degranulation in a subject can be assessed by evaluation of markers in mast cells obtained from the subject. A blood sample, lymph node biopsy, or tissue sample can be collected from a subject and mast cells from the sample evaluated for one or more (e.g., 1, 2, 3 or 4 or more) specific markers: IgE, histamine, IL-4, TNF$\alpha$, CD300a, tryptase, or MMP9. Mast cell degranulation can also be assessed using the same methods in an in vivo animal model. This assay can also be performed by adding a calcitonin receptor activator to mast cells in vitro (e.g., mast cells obtained from a subject, animal model, repository, or commercial source) and measuring the aforementioned markers to evaluate mast cell degranulation. Some of these markers (e.g., histamine, TNF$\alpha$, and IL-4) can be detected by measuring levels in the mast cell culture medium after mast cells are contacted with a calcitonin receptor activator. The effect of a calcitonin receptor activator can be determined by comparing results from before and after calcitonin receptor activator administration. This approach can also be used to evaluate the effect of a calcitonin receptor activator on degranulation by other cells, such as neutrophils (markers: CD11b, CD13, CD18, CD45, CD15, CD66b IL-1$\beta$, IL-8, and IL-6), eosinophils (markers: major basic protein (MBP), eosinophil cationic protein (ECP), eosinophil peroxidase (EPX), eosinophil-derived neurotoxin (EDN)), basophils (markers: histamine, heparin, chondroitin, elastase, lysophospholipase, and LTD-4), NK cells (markers: LAMP-1, perforin, and granzymes), and cytotoxic T cells (markers: LAMP-1, perforin, and granzymes). Markers can be detected using flow cytometry, immunohistochemistry, ELISA, western blot analysis, or in situ hybridization.

The effect of a calcitonin receptor activator on neutrophil recruitment in a subject can be assessed by evaluation of cell surface markers on neutrophils obtained from the subject. A blood sample, lymph node biopsy, or tissue sample can be collected from a subject and neutrophils from the sample evaluated for one or more (e.g., 1, 2, 3 or 4 or more) specific markers: CD11b, CD14, CD114, CD177, CD354, or CD66. To determine whether neutrophils are being recruited to a specific site (e.g., a site of inflammation). Neutrophil recruitment can also be assessed using the same methods in an in vivo animal model. This assay can also be performed by adding a calcitonin receptor activator to neutrophils in vitro (e.g., neutrophils obtained from a subject, animal model, repository, or commercial source) and measuring the aforementioned markers to evaluate neutrophil recruitment. These markers can be assessed using flow cytometry, immunohistochemistry, in situ hybridization, and other assays that allow for measurement of cell surface markers. The effect of a calcitonin receptor activator can be determined by comparing results from before and after calcitonin receptor activator administration.

The effect of a calcitonin receptor activator on eosinophil recruitment in a subject can be assessed by evaluation of cell surface markers on eosinophil obtained from the subject. A blood sample, lymph node biopsy, or tissue sample can be collected from a subject and eosinophils from the sample evaluated for one or more (e.g., 1, 2, 3 or 4 or more) specific markers: CD15, IL-3R, CD38, CD106, CD294 or CD85G. To determine whether eosinophils are being recruited to a specific site (e.g., a site of inflammation). Eosinophil recruitment can also be assessed using the same methods in an in vivo animal model. This assay can also be performed by adding a calcitonin receptor activator to eosinophils in vitro (e.g., eosinophils obtained from a subject, animal model, repository, or commercial source) and measuring the aforementioned markers to evaluate eosinophil recruitment. These markers can be assessed using flow cytometry, immunohistochemistry, in situ hybridization, and other assays that allow for measurement of cell surface markers. The effect of a calcitonin receptor activator can be determined by comparing results from before and after calcitonin receptor activator administration.

The effect of a calcitonin receptor activator on NKT cell activation in a subject can be assessed by evaluation of cell surface markers on NKT cells obtained from the subject. A blood sample, lymph node biopsy, or tissue sample can be collected from a subject and NKT cells from the sample evaluated for one or more specific markers: CD272 or CD352. Activated NKT cells produce IFN-γ, IL-4, GM-CSF, IL-2, IL-13, IL-17, IL-21 and TNFα. NKT cell activation can also be assessed using the same methods in an in vivo animal model. This assay can also be performed by adding a calcitonin receptor activator to NKT cells in vitro (e.g., NKT cells obtained from a subject, animal model, repository, or commercial source) and measuring the aforementioned markers to evaluate NKT cell activation. Cell surface markers CD272 and CD352 can be assessed using flow cytometry, immunohistochemistry, in situ hybridization, and other assays that allow for measurement of cell surface markers. The secreted proteins can be detected in blood samples or cell culture media using ELISA, western blot analysis, or other methods for detecting proteins in solution. The effect of a calcitonin receptor activator can be determined by comparing results from before and after calcitonin receptor activator administration.

The effects of a calcitonin receptor activator on B cell activation in a subject can be assessed by evaluation of cell surface markers on B cells obtained from the subject. A blood sample, lymph node biopsy, or tissue sample can be collected from a subject and B cells from the sample evaluated for one or more (e.g., 2, 3 or 4 or more) specific markers: CD19, CD20, CD40, CD80, CD86, CD69, IgM, IgD, IgG, IgE, or IgA. B cell activation can also be assessed using the same methods in an in vivo animal model. This assay can also be performed by adding a calcitonin receptor activator to B cells in vitro (e.g., B cells obtained from a subject, animal model, repository, or commercial source) and measuring the aforementioned markers to evaluate B cell activation. These markers can be assessed using flow cytometry, immunohistochemistry, in situ hybridization, and other assays that allow for measurement of cell surface markers. The effect of a calcitonin receptor activator can be determined by comparing results from before and after calcitonin receptor activator administration.

The effect of a calcitonin receptor activator on regulatory T cell differentiation in a subject can be assessed by evaluation of markers in regulatory T cells obtained from the subject. A blood sample, lymph node biopsy, or tissue sample can be collected from a subject and regulatory T cells from the sample evaluated for one or more (e.g., 1, 2, 3, 4 or more) specific markers: CD4, CD25, or FoxP3. Regulatory T cell differentiation can also be assessed using the same methods in an in vivo animal model. This assay can also be performed by adding a calcitonin receptor activator to regulatory T cells in vitro (e.g., regulatory T cells obtained from a subject, animal model, repository, or commercial source) and measuring the aforementioned markers to evaluate regulatory T cell differentiation. These markers can be assessed using flow cytometry, immunohistochemistry, in situ hybridization, and other assays that allow for measurement of cellular markers. The effect of a calcitonin receptor activator can be determined by comparing results from before and after calcitonin receptor activator administration.

The effect of a calcitonin receptor activator on innervation of a lymph node or secondary lymphoid organ can be assessed by evaluation of neuronal markers in a lymph node or secondary lymphoid organ biopsy sample obtained from a human subject or animal model. A biopsy can be collected from the subject and evaluated for one or more (e.g., 1, 2, 3, 4, or 4 or more) neuronal markers selected from: Neurofilament, synapsin, synaptotagmin, or neuron specific enolase. Lymph node innervation can also be assessed using electrophysiological approaches (e.g., recording neuronal activity in a lymph node or secondary lymphoid organ in a human subject or animal model). The effect of a calcitonin receptor activator can be determined by comparing results from before and after calcitonin receptor activator administration.

The calcitonin receptor activator can also reduce the number of nerve fibers in the affected tissue or reduce the activity of peripheral nerve fibers in the affected tissue. For example, the method includes administering to the subject (e.g., a human subject or animal model) a calcitonin receptor activator in an amount and for a time sufficient to reduce the number of nerve fibers in the affected tissue or reduce the activity of peripheral nerve fibers in the affected tissue. The affected tissue can be a lymph node, a lymphoid organ, or the bone marrow niche. The number of nerve fibers in the affected tissue or the activity of peripheral nerve fibers in the affected tissue can be decreased in the subject at least 1%, 2%, 5%, 10%, 15%, 20%, 25%, 30%, 35%, 40%, 50%, 60%, 70%, 80%, 90%, 95% or more, compared to before the administration. The number of nerve fibers in the affected tissue or the activity of peripheral nerve fibers in the affected tissue can be decreased in the subject between 5-20%, between 5-50%, between 10-50%, between 20-80%, between 20-70%.

The calcitonin receptor activator can also increase the number of nerve fibers in the affected tissue or increase the activity of peripheral nerve fibers in the affected tissue. For example, the method includes administering to the subject (e.g., a human subject or animal model) a calcitonin receptor activator in an amount and for a time sufficient to increase the number of nerve fibers in the affected tissue or increase the activity of peripheral nerve fibers in the affected tissue. The affected tissue can be a lymph node, a lymphoid organ, or the bone marrow niche. The number of nerve fibers in the affected tissue or the activity of peripheral nerve fibers in the affected tissue can be increased in the subject at least 1%, 2%, 5%, 10%, 15%, 20%, 25%, 30%, 35%, 40%, 50%, 60%, 70%, 80% or more, compared to before the administration. The number of nerve fibers in the affected tissue or the activity of peripheral nerve fibers in the affected tissue can be increased in the subject between 5-20%, between 5-50%, between 10-50%, between 20-80%, between 20-70%.

The nerve fibers that are modulated can be part of the peripheral nervous system, e.g., a somatic nerve, an autonomic nerve, a sensory nerve, a cranial nerve, an optic nerve, an olfactory nerve, a sympathetic nerve, a parasympathetic nerve, a chemoreceptor, a photoreceptor, a mechanoreceptor, a thermoreceptor, a nociceptor, an efferent nerve fiber, or an afferent nerve fiber.

The effect of a calcitonin receptor activator on immune cell cytokine production can be assessed by evaluation of cellular markers in an immune cell sample obtained from a human subject or animal model. A blood sample, lymph node biopsy, or tissue sample can be collected for the subject and evaluated for one or more (e.g., 1, 2, 3, 4, or 4 or more) cytokine markers selected from: pro-inflammatory cytokines (e.g., IL-1β, IL-5, IL-6, IL-8, IL-10, IL-12, IL-13, IL-17, IL-18, IL-22, TNFα, IFNγ, GMCSF), pro-survival cytokines (e.g., IL-2, IL-4, IL-6, IL-7, and IL-15) and anti-inflammatory cytokines (e.g., IL-4, IL-10, IL-11, IL-13, IFNα, and TGFβ). Some cytokines can function as both pro- and anti-inflammatory cytokines depending on context or indication (e.g., IL-4 is often categorized as an anti-inflammatory cytokine, but plays a pro-inflammatory role in mounting an allergic or anti-parasitic immune response). Cytokines can be also detected in the culture media of immune cells contacted with a calcitonin receptor activator. Cytokines can be detected using ELISA, western blot analysis, or other methods for detecting protein levels in solution. The effect of a calcitonin receptor activator can be determined by comparing results from before and after calcitonin receptor activator administration.

In some embodiments, a calcitonin receptor activator decreases or prevents the development of TLOs to decrease local inflammation in autoimmune diseases. TLOs are highly similar to SLOs and exhibit T and B cell compartmentalization, APCs such as DCs and follicular DCs, stromal cells, and a highly organized vascular system of high endothelial venules. In some embodiments, a calcitonin receptor activator decreases or prevents the development of HEVs within tertiary lymphoid organs to decrease local inflammation in autoimmune diseases. HEVs can be detected using the monoclonal antibody MECA-79.

In some embodiments, a calcitonin receptor activator modulates dendritic cell maturation (e.g., activation). Dendritic cell maturation can be increased to promote their migration from peripheral tissues into secondary lymphoid organs to improve T cell activation in the draining lymph node (e.g., to increase vaccine efficacy. Dendritic cell maturation can be decreased to decrease their migration from peripheral tissues into secondary lymphoid organs to inhibit T cell activation in the draining lymph node (e.g., to improve outcomes in organ transplantation or to reduce the severity of or treat autoimmune diseases).

Table 1 lists additional markers and relevant assays that may be used to assess the level, function and/or activity of immune cells in the methods described herein.

TABLE 1

ASSESSMENT OF IMMUNE CELL PHENOTYPES

| IMMUNE CELL | ASSOCIATED CYTOKINES | MARKER | ASSAYS |
|---|---|---|---|
| Th1 helper | IFN-γ | CD4 | ELISPOT |
|  | IL-2 | CD94 | In situ hybridization |
|  | IL-12 | CD119 | Immunohistochemistry |
|  | IL-18 | (IFNγ R1) | Limiting dilution Analysis |
|  | IL-27 | CD183 | Single-cell PCR |
|  | TNFα | (CXCR3) | In vivo capture assay |
|  | TNFβ/LTα | CD186 | ELISA |
|  |  | (CXCR6) | Flow cytometry |
|  |  | CD191 |  |
|  |  | (CCR1) |  |
|  |  | CD195 |  |
|  |  | (CCR5) |  |
|  |  | CD212 (IL-12Rβ1&2) |  |
|  |  | CD254 (RANKL) |  |
|  |  | CD278 (ICOS) |  |
|  |  | IL-18R |  |
|  |  | MRP1 |  |
|  |  | NOTCH3 |  |
|  |  | TCR |  |
|  |  | TIM3 |  |
| Th2 helper | IL-4 | CD4 | ELISPOT |
|  | IL-2 | CD30 | In situ hybridization |
|  | IL-6 | CD119 | Immunohistochemistry |
|  | IL-33 | (IFNγ R1) | Limiting dilution |
|  | IL-17E (IL-25) | CD184 | Analysis |
|  | IL-31 | (CXCR4) | Single-cell PCR |
|  | IL-3 | CD185 | In vivo capture |
|  | IL-10 | (CXCR5) | assay |
|  | IL-13 | CD193 | ELISA |
|  |  | (CCR3) | Flow cytometry |
|  |  | CD194 |  |
|  |  | (CCR4) |  |
|  |  | CD197 |  |
|  |  | (CCR7) |  |
|  |  | CD278 |  |
|  |  | (ICOS) |  |
|  |  | CD294 |  |
|  |  | (CRTh2) |  |
|  |  | CDw198 |  |
|  |  | (CCR8) |  |
|  |  | IL-17RB |  |
|  |  | IL-33Rα (ST2) |  |
|  |  | NOTCH1 |  |
|  |  | NOTCH2 |  |
|  |  | TCR |  |
|  |  | TIM1 |  |
| Th17 helper | TGFβ1 | CD4 | ELISPOT |
|  | IL-1β | CD27 | In situ hybridization |
|  | IL-6 | CD62L | Immunohistochemistry |

TABLE 1-continued

ASSESSMENT OF IMMUNE CELL PHENOTYPES

| IMMUNE CELL | ASSOCIATED CYTOKINES | MARKER | ASSAYS |
|---|---|---|---|
| | IL-21 | CD127 (IL-7R) | Limiting dilution |
| | IL-23 | CD161 | Analysis |
| | IL-17A | CD184 (CXCR4) | Single-cell PCR |
| | IL-17F | CD194 (CCR4) | In vivo capture assay |
| | IL-22 | CD196 (CCR6) | ELISA |
| | IL-26 | CD197 (CCR7) | Flow cytometry |
| | GM-CSF | CD212b1 (IL-12Rβ1) | |
| | MIP-3α | CD213a1 (IL-13Rα1) | |
| | TNFα | CD278 (ICOS) | |
| | | IL-1R1 | |
| | | IL-21R | |
| | | IL-23R | |
| Treg | TGFβ1 | CD4 | ELISPOT |
| | IL-2 | CD25 | In situ hybridization |
| | IL-10 | CD39 | Immunohistochemistry |
| | IL-35 | CD73 | Limiting dilution |
| | | CD45RO | Analysis |
| | | CD121a (IL-1R1) | Single-cell PCR |
| | | CD121b (IL-1R2) | In vivo capture assay |
| | | CD127low | ELISA |
| | | CD134 (OX40) | Flow cytometry |
| | | CD137 (4-1BB) | |
| | | CD152 (CTLA-4) | |
| | | CD357 (GITR/AITR) | |
| | | Foxp3 | |
| | | FR4 (m) | |
| | | GARP (activated) | |
| | | Helios | |
| | | LAP/TGFβ (activated) | |
| | | TIGIT | |
| Dendritic cell | GM-CSF | CD1a | ELISPOT |
| | IFNγ | CD8 | In situ hybridization |
| | IL-4 | CD11c | Immunohistochemistry |
| | GM-CSF | CD80 | Limiting dilution |
| | IFNα | CD83 | Analysis |
| | IL-1α | CD85 (ILT) family | Single-cell PCR |
| | IL-1β | CD86 | In vivo capture assay |
| | IL-6 | CD141 (h) | ELISA |
| | IL-8 | CD169 | Flow cytometry |
| | IL-10 | CD172 | |
| | IL-12 | CD184 (CXCR4) | |
| | IL-15 | CD197 (CCR7) | |
| | IL-18 | CD205 | |
| | IL-23 | CD206 | |
| | IL-27 | CD207 | |
| | IP-10 | CD209 | |
| | M-CSF | CD215 (IL-15R) | |
| | RANTES (CCL5) | CD282 (TLR2) | |
| | TGFβ | CD284 (TLR4) | |
| | TNFα | CD286 (TLR6) | |
| | | Clec Family | |
| Macrophages/Monocytes | FLT3 Ligand | CD11b | ELISPOT |
| | GM-CSF | CD14 (mono) | In situ hybridization |
| | M-CSF | CD16 | Immunohistochemistry |
| | CXCL9 | CD32 | Limiting dilution |
| | CXCL10 | CD68 | Analysis |
| | CXCL11 | CD85a (ILT5) | Single-cell PCR |
| | G-CSF | CD163 | In vivo capture |
| | GM-CSF | CD169 | assay |

TABLE 1-continued

ASSESSMENT OF IMMUNE CELL PHENOTYPES

| IMMUNE CELL | ASSOCIATED CYTOKINES | MARKER | ASSAYS |
|---|---|---|---|
| | IFNβ | CD195 (CCR5) | ELISA |
| | IL-1α | CD204 | Flow cytometry |
| | IL-1β | CD206 | |
| | IL-6 | CD282 (TLR2) | |
| | IL-8 | CD284 (TLR4) | |
| | IL-10 | CD286 (TLR6) | |
| | IL-12p40 & p70 | CD354 (Trem-1) | |
| | IL-18 | Clec Family | |
| | IL-23 | F4/80 (m) | |
| | IL-27 | HLA-DR | |
| | M-CSF | | |
| | MIP-2α (CXCL2) | | |
| | RANTES (CCL5) | | |
| | TNFα | | |
| Natural Killer Cell | IL-2 | CD16 | ELISPOT |
| | IL-12 | CD25 | In situ hybridization |
| | IL-15/IL-15R | CD49b | Immunohistochemistry |
| | IL-18 | CD56 (h) | Limiting dilution |
| | Granzyme B | CD94 | Analysis |
| | IL-17A | CD158 family (KIR) (h) | Single-cell PCR |
| | IL-22 | CD181 (CXCR1) | In vivo capture assay |
| | MIP-1α (CCL3) | CD183 (CXCR3) | ELISA |
| | MIP-1β (CCL4) | CD184 (CXCR4) | Flow cytometry |
| | Perforin | CD186 (CXCR6) | |
| | RANTES (CCL5) | CD192 (activated) | |
| | TNFα | CD195 (CCR5) | |
| | | CD197 (CCR7) | |
| | | CD212 (IL-12R) | |
| | | CD244 | |
| | | CD314 (NKG2D) | |
| | | CX3CR1 | |
| | | Eomes | |
| | | KLRG1 | |
| | | Ly49 family (m) | |
| | | NK1.1 | |
| | | NKG2A | |
| | | NKp30, NKp42 | |
| | | NKp44 (h), NKp46 | |
| | | T-bet | |
| Innate Lymphoid Cell 1 (ILC1) | IFN-γ | CD335 (NKp46) | ELISPOT |
| | TNF | CD336 (NKp44) | In situ hybridization |
| | | CD94 | Immunohistochemistry |
| | | CD56 (NCAM) | Limiting dilution |
| | | CD103 | Analysis |
| | | T-bet | Single-cell PCR |
| | | | In vivo capture assay |
| | | | ELISA |
| | | | Flow cytometry |
| Innate Lymphoid Cell 2 (ILC2) | Areg | CD127 | ELISPOT |
| | IL-5 | CRTH2 | In situ hybridization |
| | IL-13 | ST2 (IL-33R) | Immunohistochemistry |
| | | RORα | Limiting dilution |
| | | GATA3 | Analysis |
| | | | Single-cell PCR |
| | | | In vivo capture assay |
| | | | ELISA |
| | | | Flow cytometry |
| Innate Lymphoid Cell 3 (ILC3) | CCL3 | CD127 | ELISPOT |
| | LTs | CD117 (c-kit) | In situ hybridization |
| | IL-22 | CD335 (NKp46) | Immunohistochemistry |
| | IL-17 | CD336 (NKp44) | Limiting dilution |
| | IFN-γ | IL-23R | Analysis |
| | | RORγt | Single-cell PCR |
| | | | In vivo capture assay |
| | | | ELISA |
| | | | Flow cytometry |
| Activated B cell/Plasma cells | Antibodies | CD19 | Flow cytometry |
| | IgM | CD25 | |
| | IgG | CD30 | |
| | IgD | IgM | |
| | IgE | CD19 | |

TABLE 1-continued

ASSESSMENT OF IMMUNE CELL PHENOTYPES

| IMMUNE CELL | ASSOCIATED CYTOKINES | MARKER | ASSAYS |
|---|---|---|---|
| | IgA | IgG | |
| | | CD27 | |
| | | CD38 | |
| | | CD78 | |
| | | CD138 | |
| | | CD319 | |

TABLE 2

EXAMPLES OF HUMAN CHEMOKINES

| Systematic name | Human gene | Alternate human names | Expression | Human receptor(s) and their expression | Known functions |
|---|---|---|---|---|---|
| C Family | | | | | |
| XCL1 | XCL1 | Lymphotactin, SCM-1 alpha, ATAC | activated CD8+ T cells and other MHCI restricted T cells | XCR1: cross-presenting drendritic cells | migration and activation of lymphocytes, NK cells |
| XCL2 | XCL2 | SCM-1 beta | expressed in activated T cells | XCR1: cross-presenting drendritic cells | migration and activation of lymphocytes, NK cells |
| CX3C Family | | | | | |
| CX3CL1 | CX3CL1 | Fractalkine, Neurotactin, ABCD-3 | brain, heart, lung, kidney, skeletal muscle and testis. Up-regulated in endothelial cells and microglia by inflammation | CX3CR1: lymphocytes, monocytes | migration and adhesion of lymphocytes and monocytes |
| CC Family | | | | | |
| CCL1 | CCL1 | I-309 | activated T cells | CCR8: natural killer cells, monocytes and lymphocytes DARC: erytrocytes, endothelial and epithelial cells | migration of monocytes, NK cells, immature B cells and DCs |
| CCL2 | CCL2 | MCP-1, MCAF, HC11 | monocytes, macrophages and dendritic cells, activated NK cells | CCR2: monocytes CCR4: lymphocytes CCR11: unkown D6: lymphocytes, lymphatic endothelial cells, macrophages DARC: erytrocytes, endothelial and epithelial cells | migration of monocytes and basophils |
| CCL3 | CCL3 | MIP-1 alpha, LD78 alpha, GOS19, Pat464 | T cells, B cells, and monocytes after antigen or mitogen stimulation | CCR1: lymphocytes, monocytes, airway smooth muscle cells CCR4: lymphocytes CCR5: T cells, macrophages, dendritic cells, eosinophils and microglia D6: lymphocytes, lymphatic endothelial cells, macrophages | adhesion of lymphocytes |
| CCL3L1 | CCL3L1 | LD78 beta | Unknown | CCR1: lymphocytes, monocytes, airway smooth muscle cells CCR3: eosinophils, basophils, Th2 cells, CD34+ hematopoetic progenitors, keratinocytes, mast cells CCR5: T cells, macrophages, dendritic | migration of lymphocytes and monocytes |

TABLE 2-continued

EXAMPLES OF HUMAN CHEMOKINES

| Systematic name | Human gene | Alternate human names | Expression | Human receptor(s) and their expression | Known functions |
|---|---|---|---|---|---|
| | | | | cells, eosinophils and microglia<br>D6: lymphocytes, lymphatic endothelial cells, macrophages | |
| CCL3L3 | CCL3L3 | LD78 beta | Unknown | CCR1: lymphocytes, monocytes, airway smooth muscle cells<br>CCR3: eosinophils, basophils, Th2 cells, CD34+ hematopoetic progenitors, keratinocytes, mast cells<br>CCR5: T cells, macrophages, dendritic cells, eosinophils and microglia | migration of lymphocytes and monocytes |
| CCL4 | CCL4 | MIP-1 beta, AT744.1, ACT-2, G-26, HC21, H400, MAD-5, LAG-1 | macrophages, dendritic cells | CCR1: lymphocytes, monocytes, airway smooth muscle cells<br>CCR5: T cells, macrophages, dendritic cells, eosinophils and microglia<br>CCR8: natural killer cells, monocytes and lymphocytes<br>D6: lymphocytes, lymphatic endothelial cells, macrophages | migration and adhesion of lymphocytes, regulatory T cells, NK cells, monocyrtes |
| CCL4L1 | CCL4L1 | AT744.2 | macrophages, dendritic cells | CCR1: lymphocytes, monocytes, airway smooth muscle cells<br>CCR5: T cells, macrophages, dendritic cells, eosinophils and microglia | CCR1 and CCR5 expressing cells |
| CCL4L2 | CCL4L2 | | macrophages, dendritic cells | CCR1: lymphocytes, monocytes, airway smooth muscle cells<br>CCR5: T cells, macrophages, dendritic cells, eosinophils and microglia | CCR1 and CCR5 expressing cells |
| CCL5 | CCL5 | RANTES | T cells, macrophages, platelets, synovial fibroblasts, tubular epithelium, certain types of tumor cells | CCR1: lymphocytes, monocytes, airway smooth muscle cells<br>CCR3: eosinophils, basophils, Th2 cells, CD34+ hematopoetic progenitors, keratinocytes, mast cells<br>CCR4: lymphocytes<br>CCR5: T cells, macrophages, dendritic cells, eosinophils and microglia<br>D6: lymphocytes, lymphatic endothelial cells, macrophages<br>DARC: erytrocytes, endothelial and epithelial cells | migration of monocytes, memory T helper cells and eosinophils, causes the release of histamine from basophils and activates eosinophils |
| CCL7 | CCL7 | MCP-3 | macrophages, certain types of tumor cells | CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>D6: lymphocytes, lymphatic endothelial | migration of monocytes, activation of macrophages |

TABLE 2-continued

EXAMPLES OF HUMAN CHEMOKINES

| Systematic name | Human gene | Alternate human names | Expression | Human receptor(s) and their expression | Known functions |
|---|---|---|---|---|---|
| CCL8 | CCL8 | MCP-2, HC14 | fibroblasts, endothelial cells | cells, macrophages<br>DARC: erythrocytes, endothelial and epithelial cells<br>CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>CCR5: T cells, macrophages, dendritic cells, eosinophils and microglia<br>CCR11: unkown<br>D6: lymphocytes, lymphatic endothelial cells, macrophages<br>DARC: erythrocytes, endothelial and epithelial cells | migration of monocytes, lymphocytes, basophils and eosinophils |
| CCL11 | CCL11 | Eotaxin | lung epithelial cells, pleural mesothelial cells, bronchial airway epithelial cells, smooth muscle cells | CCR3: eosinophils, basophils, Th2 cells, CD34+ hematopoetic progenitors, keratinocytes, mast cells<br>CCR5: T cells, macrophages, dendritic cells, eosinophils and microglia<br>D6: lymphocytes, lymphatic endothelial cells, macrophages<br>DARC: erythrocytes, endothelial and epithelial cells | migration and activation of inflammatory leukocytes, particularly eosinophils |
| CCL12 | | | stromal cells in lung and secondary lymphoid organs | CCR2: monocytes | migration and activation of monocytes |
| CCL13 | CCL13 | MCP-4, CK beta 10, NCC-1 | synovial fibroblasts, chondrocytes | CCR1: lymphocytes, monocytes, airway smooth muscle cells<br>CCR2: monocytes<br>CCR3: eosinophils, basophils, Th2 cells, CD34+ hematopoetic progenitors, keratinocytes, mast cells<br>CCR5: T cells, macrophages, dendritic cells, eosinophils and microglia<br>CCR11: unkown<br>D6: lymphocytes, lymphatic endothelial cells, macrophages<br>DARC: erythrocytes, endothelial and epithelial cells | migration of eosinophils, monocytes and T lymphocytes |
| CCL14 | CCL14 | HCC-1, MCIF, CK beta 1, NCC-2 | spleen, bone marrow, liver, muscle and gut | CCR1: lymphocytes, monocytes, airway smooth muscle cells<br>CCR3: eosinophils, basophils, Th2 cells, CD34+ hematopoetic progenitors, keratinocytes, mast cells<br>CCR5: T cells, macrophages, dendritic cells, eosinophils and microglia | activation of monocytes |

TABLE 2-continued

EXAMPLES OF HUMAN CHEMOKINES

| Systematic name | Human gene | Alternate human names | Expression | Human receptor(s) and their expression | Known functions |
|---|---|---|---|---|---|
| | | | | D6: lymphocytes, lymphatic endothelial cells, macrophages DARC: erytrocytes, endothelial and epithelial cells | |
| CCL15 | CCL15 | MIP-1 delta, LKN-1, HCC-2, MIP-5, NCC-3 | airway smooth muscle cells, lung leukocytes, alveolar macrophages, basophils | CCR1: lymphocytes, monocytes, airway smooth muscle cells CCR3: eosinophils, basophils, Th2 cells, CD34+ hematopoetic progenitors, keratinocytes, mast cells | migration of monocytes and eosinophils, proliferation of CD34 myeloid progenitor cells |
| CCL16 | CCL16 | HCC-4, LEC, ILINCK, NCC-4, LMC, CK beta 12 | liver, thymus, and spleen | CCR1: lymphocytes, monocytes, airway smooth muscle cells CCR2: monocytes CCR5: T cells, macrophages, dendritic cells, eosinophils and microglia CCR8: natural killer cells, monocytes and lymphocytes DARC: erytrocytes, endothelial and epithelial cells H4: bone marrow, eosinophils, T-cells, dendritic cells, monocytes, mast cells, neutrophil | migration of lymphocytes and monocytes |
| CCL17 | CCL17 | TARC, ABCD-2 | constitutively expressed in thymus, dendritic cells, keratinocytes | CCR4: lymphocytes CCR8: natural killer cells, monocytes and lymphocytes D6: lymphocytes, lymphatic endothelial cells, macrophages DARC: erytrocytes, endothelial and epithelial cells | Migration and activation of T cells |
| CCL18 | CCL18 | PARC, DC-CK1, AMAC-1, CK beta 7, MIP-4 | dendritic cells, monocytes, and macrophages | CCR8: natural killer cells, monocytes and lymphocytes PITPNM3: breast cancer cells DARC: erytrocytes, endothelial and epithelial cells | migration of naive and regulatory lymphocytes, dendritic cells |
| CCL19 | CCL19 | MIP-3 beta, ELC, Exodus-3, CK beta 11 | fibroblastic reticular cells, dendritic cells | CCR7: lymphocytes (mainly naive and memory), mature dendritic cells CCR11: unkown CCRL2: neutrophils, monocytes | migration of naive and memory lymphocytes and mature dendritic cells |
| CCL20 | CCL20 | MIP-3 alpha, LARC, Exodus-1, ST38, CK beta 4 | epidermis (keratinocytes), lymphocytes | CCR6: immature dendritic cells and memory T cells | migration of lymphocytes, DCs and neutrophils |
| CCL21 | CCL21 | 6Ckine, Exodus-2, SLC, TCA-4, CK beta 9 | Stromal cells, lymphatic endothelial cells, fibroblastic reticular cells, dendritic cells | CCR7: lymphocytes (mainly naive and memory), mature dendritic cells CCR11: unkown | migration of lymphocytes homing to secondary lymphoid organs, induces integrin-mediated lymphocyte adhesion |

TABLE 2-continued

EXAMPLES OF HUMAN CHEMOKINES

| Systematic name | Human gene | Alternate human names | Expression | Human receptor(s) and their expression | Known functions |
|---|---|---|---|---|---|
| CCL22 | CCL22 | MDC | Macrophages | CCR4: lymphocytes D6: lymphocytes, lymphatic endothelial cells, macrophages | migration of NK cells, chronically activated T cells, monocytes and DCs |
| CCL23 | CCL23 | MPIF-1, CK beta 8, CK beta 8-1, MIP-3 | Monocytes | CCR1: lymphocytes, monocytes FPRL-1: monocytes, mast cells | migration of monocytes, resting T cells and neutrophils |
| CCL24 | CCL24 | Eotaxin-2, MPIF-2, CK beta 6 | lung tissue | CCR3: eosinophils, basophils, Th2 cells, CD34+ hematopoetic progenitors, keratinocytes, mast cells | migration of basophils |
| CCL25 | CCL25 | TECK, CK beta 15 | thymic dendritic cells and mucosal epithelial cells | CCR9: T lymphocytes of small intestine | migration of dendritic cells, thymocytes and activated macrophages |
| CCL26 | CCL26 | Eotaxin-3, MIP-4 alpha, IMAC, TSC-1 | heart, lung and ovary and in endothelial cells stimulated with IL4 | CCR3: eosinophils, basophils, Th2 cells, CD34+ hematopoetic progenitors, keratinocytes, mast cells CX3CR1: lymphocytes, monocytes | migration of eosinophils and basophils |
| CCL27 | CCL27 | CTACK, ILC, PESKY, ESKINE | Keratinocytes | CCR10: melanocytes, plasma cells and skin-homing T cells | migration of memory T cells |
| CCL28 | CCL28 | MEC | columnar epithelial cells in the gut, lung, breast and the salivary glands | CCR3: eosinophils, basophils, Th2 T cells, CD34+ hematopoetic progenitors, keratinocytes, mast cells CCR10: melanocytes, plasma cells and skin-homing T cells | migration of lymphocytes and eosinophils |
| CXC Family | | | | | |
| CXCL1 | CXCL1 | GRO alpha, MGSA, GRO1, NAP-3 | mammary, fibroblasts, mammary epithelial cells, endothelial cells, activated, monocytes, macrophages and neutrophils | CXCR2 (IL8RB): neutrophils DARC: erytrocytes, endothelial and epithelial cells | migration of neutrophils |
| CXCL2 | CXCL2 | GRO beta, MIP-2 alpha, GRO2 | monocytes, macrophages | CXCR2 (IL8RB): neutrophils DARC: erytrocytes, endothelial and epithelial cells | migration and activation of neutrophils, basophils, hematopoietic stem cells |
| CXCL3 | CXCL3 | GRO gamma, MIP-2 beta, GRO3 | smooth muscle cells, epithelial cells | CXCR2 (IL8RB): neutrophils DARC: erytrocytes, endothelial and epithelial cells | migration and activation of neutrophils |
| CXCL4 | PF4 | PF4 | activated platelets, megakaryocytes, leukocytes, endothelial cells | CXCR3 (CD183b): T cells, NK cells CXCR3-B: T cells, NK cells DARC: erytrocytes, endothelial and epithelial cells | migration of neutrophils and fibroblasts, inhibiting endothelial cell proliferation and chemotaxis |
| CXCL4L1 | PF4V1 | PF4V1 | smooth muscle cells, T cells, and platelets | CXCR3 (CD183b): T cells, NK cells CXCR3-B: T cells, NK cells | inhibiting endothelial cell proliferation and chemotaxis |

TABLE 2-continued

EXAMPLES OF HUMAN CHEMOKINES

| Systematic name | Human gene | Alternate human names | Expression | Human receptor(s) and their expression | Known functions |
|---|---|---|---|---|---|
| CXCL5 | CXCL5 | ENA-78 | fibroblasts, epithelial cells, eosinophils | CXCR2 (IL8RB): neutrophils<br>DARC: erytrocytes, endothelial and epithelial cells | migration and activation of neutrophils |
| CXCL6 | CXCL6 | GCP-2 | fibroblasts, epithelial cells | CXCR1 (IL8RA): neutrophils<br>CXCR2 (IL8RB): neutrophils<br>DARC: erytrocytes, endothelial and epithelial cells | migration of neutrophils |
| CXCL7 | PPBP | NAP-2, CTAPIII, beta-TG | activated platelets | CXCR1 (IL8RA): neutrophils<br>CXCR2 (IL8RB): neutrophils | migration of neutrophils |
| CXCL8 | IL8 | IL-8, NAP-1, MDNCF, GCP-1 | macrophages, epithelial cells, airway smooth muscle cells, endothelial cells | CXCR1 (IL8RA): neutrophils<br>CXCR2 (IL8RB): neutrophils<br>DARC: erytrocytes, endothelial and epithelial cells | migration of neutrophils, basophils, and T-cells, and angiogenic factor |
| CXCL9 | CXCL9 | MIG, CRG-10 | monocytes, macrophages and endothelial cells | CXCR3 (CD183b): T cells, NK cells<br>CXCR3-B: T cells, NK cells<br>DARC: erytrocytes, endothelial and epithelial cells | migration of Th1 lymphocytes, angiogenic factor |
| CXCL10 | CXCL10 | IP-10 | neutrophils, hepatocytes, endothelial cells and keratinocytes | CXCR3 (CD183b): T cells, NK cells<br>CXCR3-B: T cells, NK cells<br>DARC: erytrocytes, endothelial and epithelial cells | migration of CD4+ T cells |
| CXCL11 | CXCL11 | I-TAC, beta-R1, H174, IP-9 | peripheral blood leukocytes, pancreas and liver astrocytes and at moderate levels in thymus, spleen and lung | CXCR3 (CD183b): T cells, NK cells<br>CXCR7 (ACKR3): tumor cells and tumor-associated blood endothelium<br>DARC: erytrocytes, endothelial and epithelial cells | migration of interleukin-activated T cells but not unstimulated T cells, neutrophils or monocytes. |
| CXCL12 | CXCL12 | SDF-1, PBSF | ubiquitously expressed in many tissues and cell types | CXCR4: brain, heart, lymphocytes, HSCs, blood endothelial cells and umbilical cord endothelial cell<br>CXCR7 (ACKR3): tumor cells and tumor-associated blood endothelium | migration of lymphocytes and hepatopoietic stem cells, angiogenic factor |
| CXCL13 | CXCL13 | BCA-1, BLC | follicles of the spleen, lymph nodes, and Peyer's patches | CXCR3 (CD183b): T cells, NK cells<br>CXCR5: Burkitt's lymphoma, lymph node follicules, spleen<br>DARC: erytrocytes, endothelial and epithelial cells | migration of B cells |
| CXCL14 | CXCL14 | BRAK, BMAC | Fibroblasts | unknown | migration of monocytes, NK cells, DCs |
| CXCL16 | CXCL16 | SR-PSOX | DCs | CXCR6: T cells | migration of several subsets of T cells and NKT cells |
| CXCL17 | CXCL17 | DMC, VCC-1 | Lung and tumor tissue | unknown | migration of DCs and monocytes |

TABLE 3

EXAMPLES OF HUMAN IMMUNE CELL TRAFFICKING MOLECULES

| Trafficking molecule | Trafficking molecule expressing or presenting cells | Leukocyte ligand | Function in the extravasation cascade |
|---|---|---|---|
| P-selectin | Blood endothelial cell | PSGL-1, L-selectin, CD44 | Tethering/Rolling during extravasation cascade |
| E-selectin | Blood endothelial cell | Glycoprotein, glycolipid, PSG L-1 | Tethering/Rolling during extravasation cascade |
| PNAd | Blood endothelial cell | L-selectin | Tethering/Rolling during extravasation cascade |
| MAdCAM | Blood endothelial cell | L-selectin, integrins | Tethering/Rolling, arrest during extravasation cascade |
| VCAM-1 | Blood endothelial cell | Integrins (e.g. VLA-4) | Tethering/Rolling, arrest during extravasation cascade |
| Chemokines | Blood endothelial cell | GPCRs | Integrin activation, allowing binding of cell adhesion molecules and arrest |
| ICAM-1 | Blood endothelial cell | Integrins (e.g. LFA-1, Mac-1) | Arrest during extravasation cascade |
| ICAM-2 | Blood endothelial cell | Integrins (e.g. LFA-1, Mac-1) | Arrest during extravasation cascade |
| PECAM1 (CD31) | Blood endothelial cell | Integrins (e.g. alpha v beta 3), PECAM1 | Transmigration |
| JAM-A/-B/-C | Blood endothelial cell | Integrins (e.g. LFA-1, Mac-1, VLA-4) | Transmigration |
| ESAM | Blood endothelial cell | unknown | Transmigration |
| CD99 | Blood endothelial cell | CD99 | Transmigration |
| CD99L2 | Blood endothelial cell | possibly CD99L | Transmigration |
| VE-cadherin | Blood endothelial cell | None | Transmigration |
| PVR | Blood endothelial cell | DNAM1 | Transmigration |
| S1P | Lymphatic endothelial cell | S1P receptor 1 (S1P1) | Entry into afferent and efferent lymphatics (in peripheral or SLOs respectively) |

Inflammatory and Autoimmune Conditions

The methods described herein can be used to treat an inflammatory or autoimmune condition or disease in a subject in need thereof by administering an effective amount of a calcitonin receptor activator to the subject. The methods described herein can further include a step of identifying (e.g., diagnosing) a subject who has an inflammatory or autoimmune condition, e.g., an inflammatory or autoimmune condition described herein. The method can include administering locally to the subject a calcitonin receptor activator described herein in a dose (e.g., effective amount) and for a time sufficient to treat the autoimmune or inflammatory condition or disease.

The methods described herein can be used to inhibit an immune response in a subject in need thereof, e.g., the subject has an autoimmune condition and is in need of inhibiting an immune response against self- or auto-antibodies (e.g., the subject has multiple sclerosis (MS), psoriasis, Crohn's disease, inflammatory bowel disease (IBD), ulcerative colitis, dermatitis, asthma, fibrosis, or wound healing, or another autoimmune condition described herein). The methods described herein can also include a step of selecting a subject in need of inhibiting an immune response, e.g., selecting a subject who has or who has been identified to have an inflammatory or autoimmune condition.

The methods described herein can also be used to potentiate or increase an immune response in a subject in need thereof, e.g., an immune response to an infection. For example, the subject has a chronic infection (e.g., a persistent viral infection, bacterial infection, fungal infection, *mycoplasma* infection or parasitic infection). The viral infection may be, e.g., a persistent viral infection from hepatitis virus, a human immunodeficiency virus (HIV), a human T-lymphotrophic virus (HTLV), a herpes virus, an Epstein-Barr virus, or a human papilloma virus. Persistent viral infections may also include infections caused by a latent virus (e.g., JC virus), e.g., the subject has progressive multifocal leukoencephalopathy (PML). The methods described herein can also include a step of selecting a subject in need of potentiating an immune response, e.g., selecting a subject who has a persistent or chronic infection.

Types of Inflammatory and Autoimmune Conditions

In the methods described herein relating to inflammatory and autoimmune conditions, the condition may be selected from: Acute Disseminated Encephalomyelitis (ADEM); Acute necrotizing hemorrhagic leukoencephalitis; Addison's disease; Adjuvant-induced arthritis; Agammaglobulinemia; Alopecia areata; Amyloidosis; Ankylosing spondylitis; Anti-GBM/Anti-TBM nephritis; Antiphospholipid syndrome (APS); Autoimmune angioedema; Autoimmune aplastic anemia; Autoimmune dysautonomia; Autoimmune gastric atrophy; Autoimmune hemolytic anemia; Autoimmune hepatitis; Autoimmune hyperlipidemia; Autoimmune immunodeficiency; Autoimmune inner ear disease (AIED); Autoimmune myocarditis; Autoimmune oophoritis; Autoimmune pancreatitis; Autoimmune retinopathy; Autoimmune thrombocytopenic purpura (ATP); Autoimmune thyroid disease; Autoimmune urticarial; Axonal & neuronal neuropathies; Balo disease; Behcet's disease; Bullous pemphigoid; Cardiomyopathy; Castleman disease; Celiac disease; Chagas disease; Chronic inflammatory demyelinating polyneuropathy (CIDP); Chronic recurrent multifocal ostomyelitis (CRMO); Churg-Strauss syndrome; Cicatricial pemphigoid/benign mucosal pemphigoid; Crohn's disease; Cogans syndrome; Collagen-induced arthritis; Cold agglutinin disease; Congenital heart block; Coxsackie myocarditis; CREST disease; Essential mixed cryoglobulinemia; Demyelinating neuropathies; Dermatitis herpetiformis; Dermatomyositis; Devic's disease (neuromyelitis optica); Discoid lupus; Dressler's syndrome; Endometriosis; Eosinophilic esophagitis; Eosinophilic fasciitis; Erythema nodosum Experimental allergic encephalomyelitis; Experimental autoimmune encephalomyelitis; Evans syndrome; Fibromyalgia; Fibrosing alveolitis; Giant cell arteritis (temporal arteritis); Giant cell myocarditis; Glomerulonephritis; Goodpasture's syndrome; Granulomatosis with Polyangiitis (GPA) (formerly called Wegener's Granulomatosis); Graves' disease; Guillain-Barre syndrome; Hashimoto's encephalitis; Hashimoto's thyroiditis; Hemolytic anemia; Henoch-Schonlein purpura; Herpes gestationis; Hypogammaglobulinemia; Idiopathic thrombocytopenic purpura (ITP); IgA nephropathy; IgG4-related sclerosing disease; Immunoregulatory lipoproteins; Inclusion body myositis; Interstitial cystitis; Inflammatory bowel disease; Juvenile arthritis; Juvenile oligoarthritis; Juvenile diabetes (Type 1 diabetes); Juvenile myositis; Kawasaki syndrome; Lambert-Eaton syndrome; Leukocytoclastic vasculitis; Lichen planus; Lichen sclerosus; Ligneous conjunctivitis; Linear IgA disease (LAD); Lupus (SLE); Lyme disease, chronic; Meniere's disease; Microscopic polyangiitis; Mixed connective tissue disease (MCTD); Mooren's ulcer; Mucha-Habermann disease; Multiple sclerosis; Myasthenia gravis; Myositis; Narcolepsy; Neuromyelitis optica (Devic's); Neutropenia; Non-obese diabetes; Ocular cicatricial pemphigoid; Optic neuritis; Palindromic rheumatism; PANDAS (Pediatric Autoimmune Neuropsychiatric Disorders Associated with *Streptococcus*); Paraneoplastic cerebellar degeneration; Paroxysmal nocturnal hemoglobinuria (PNH); Parry Romberg syndrome; Parsonnage-Turner syndrome; Pars planitis (peripheral uveitis); Pemphigus; Pemphigus vulgaris; Peripheral neuropathy; Perivenous encephalomyelitis; Pernicious anemia; POEMS syndrome; Polyarteritis *nodosa;* Type I, II, & III autoimmune polyglandular syndromes; Polymyalgia rheumatic; Polymyositis; Postmyocardial infarction syndrome; Postpericardiotomy syndrome; Progesterone dermatitis; Primary biliary cirrhosis; Primary sclerosing cholangitis; Psoriasis; Plaque Psoriasis; Psoriatic arthritis; Idiopathic pulmonary fibrosis; Pyoderma gangrenosum; Pure red cell aplasia; Raynauds phenomenon; Reactive Arthritis; Reflex sympathetic dystrophy; Reiter's syndrome; Relapsing polychondritis; Restless legs syndrome; Retroperitoneal fibrosis; Rheumatic fever; Rheumatoid arthritis; Sarcoidosis; Schmidt syndrome; Scleritis; Scleroderma; Sclerosing cholangitis; Sclerosing sialadenitis; Sjogren's syndrome; Sperm & testicular autoimmunity; Stiff person syndrome; Subacute bacterial endocarditis (SBE); Susac's syndrome; Sympathetic ophthalmia; Systemic lupus erythematosus (SLE); Systemic sclerosis; Takayasu's arteritis; Temporal arteritis/Giant cell arteritis; Thrombocytopenic purpura (TTP); Tolosa-Hunt syndrome; Transverse myelitis; Type 1 diabetes; Ulcerative colitis; Undifferentiated connective tissue disease (UCTD); Uveitis; Vasculitis; Vesiculobullous dermatosis; Vitiligo; Wegener's granulomatosis (now termed Granulomatosis with Polyangiitis (GPA).

In some embodiments, the calcitonin receptor activator is administered in combination with an additional therapeutic agent to treat an inflammatory or autoimmune disease or condition. In some embodiments, the additional therapeutic agent is 6-mercaptopurine, 6-thioguanine, abatacept, adalimumab, alemtuzumab (Lemtrada), aminosalicylates (5-aminoalicylic acid, sulfasalazine, mesalamine, balsalazide, olsalazine), antibiotics, anti-histamines, anti-TNFα (infliximab, adalimumab, certolizumab pegol, natalizumab) Ustekinumab), azathioprine, belimumab, beta interferon, calcineurin inhibitors, certolizumab, corticosteroids (prednisone, methylprednisolone), cromolyn, cyclosporin A, cyclosporine, dimethyl fumarate (tecfidera), etanercept, fingolimod (Gilenya), fumaric acid esters, glatiramer acetate (Copaxone), golimumab, hydroxyurea, IFNγ, IL-11, infliximab, leflunomide, leukotriene receptor antagonist, long-acting beta2 agonist, methotrexate, mitoxantrone, mycophenolate mofetil, natalizumab (tysabri), NSAIDs, ocrelizumab, pimecrolimus, probiotics (VSL #3), retinoids, rituximab, salicylic acid, short-acting beta2 agonist, sulfasalazine, tacrolimus, teriflunomide (Aubagio), theophylline, tocilizumab, ustekinumab (anti-IL12/IL23), or vedolizumab (Anti alpha3 beta7 integrin).

Infection

Chronic Infections

As used herein, by "persistent infection" or "chronic infection" is meant an infection in which the infectious agent (e.g., virus, bacterium, parasite, mycoplasm, or fungus) is not cleared or eliminated from the infected host, even after the induction of an immune response. Persistent infections may be chronic infections, latent infections, or slow infections. While acute infections are relatively brief (lasting a few days to a few weeks) and resolved from the body by the immune system, persistent infections may last for months, years, or even a lifetime. These infections may also recur frequently over a long period of time, involving stages of silent and productive infection without cell killing or even producing excessive damage to the host cells. The causative infectious agents may also be detected in the host (e.g., inside specific cells of infected individuals) even after the immune response has resolved, using standard techniques. Mammals are diagnosed as having a persistent infection according to any standard method known in the art and described, for example, in U.S. Pat. Nos. 6,368,832, 6,579,854, and 6,808,710. Described herein, inter alia, are methods of treating a chronic infection in a subject with a calcitonin receptor activator described herein. The method may include administering locally to the subject a calcitonin receptor activator described herein in a dose (e.g., effective amount) and for a time sufficient to treat the infection. In embodiments, the infection is caused by a pathogen from one of the 3 following major categories:

i) viruses, including the members of the Retroviridae family such as the lentiviruses (e.g., Human immunodeficiency virus (HIV) and deltaretroviruses (e.g., human T cell leukemia virus I (HTLV-I), human T cell leukemia virus II (HTLV-II)); Hepadnaviridae family (e.g., hepatitis B virus (HBV)), Flaviviridae family (e.g., hepatitis C virus (HCV)), Adenoviridae family (e.g., Human Adenovirus), Herpesviridae family (e.g., Human cytomegalovirus (HCMV), Epstein-Barr virus, herpes simplex virus 1 (HSV-1), herpes simplex virus 2 (HSV-2), human herpesvirus 6 (HHV-6), varicella-zoster virus), Papillomaviridae family (e.g., Human Papillomavirus (HPV)), Parvoviridae family (e.g., Parvovirus B19), Polyomaviridae family (e.g., JC virus and BK virus), Paramyxoviridae family (e.g., Measles virus), Togaviridae family (e.g., Rubella virus) as well as other viruses such as hepatitis D virus;

ii) bacteria, such as those from the following families: *Salmonella* (e.g., *S. enterica Typhi*), *Mycobacterium* (e.g., *M. tuberculosis* and *M. leprae*), *Yersinia* (*Y. pestis*), *Neisseria* (e.g., *N. meningitides, N. gonorrhea*), *Burkholderia* (e.g., *B. pseudomallei*), *Brucella, Chlamydia, Helicobacter, Treponema, Borrelia*, and *Pseudomonas*; and iii) parasites, such as *Leishmania, Toxoplasma, Trypanosoma, Plasmodium, Schistosoma*, or *Encephalitozoon*.

Calcitonin receptor activators described herein can be administered in combination with a second therapeutic agent for treatment of chronic infection. Additional therapeutic agents include, for example, antiviral compounds (e.g., vidarabine, acyclovir, gancyclovir, valgancyclovir, nucleoside-analog reverse transcriptase inhibitor (NRTI) (e.g., AZT (Zidovudine), ddI (Didanosine), ddC (Zalcitabine), d4T (Stavudine), or 3TC (Lamivudine)), non-nucleoside reverse transcriptase inhibitor (NNRTI) (e.g., (nevirapine or delavirdine), protease inhibitor (saquinavir, ritonavir, indinavir, or nelfinavir), ribavirin, or interferon), antibacterial compounds, antifungal compounds, antiparasitic compounds, anti-inflammatory compounds, and analgesics.

Optionally, the subject is further administered a vaccine that elicits a protective immune response against the infectious agent that causes a persistent infection.

Neuromodulatory Combination Therapies

Neurotransmission Modulators

In some embodiments, the calcitonin receptor activator is administered in combination with a neurotransmission modulator (e.g., an agent that increases or decreases neurotransmission). A neurotransmission modulator can be used to modulate neural activity in a lymph node or site of inflammation that is innervated by nerves or to modulate immune cells that express neurotransmitter receptors. For example, in some embodiments, the neurotransmission modulator is a neurotransmitter or neurotransmitter receptor listed in Table 4 or 5, or an agonist or antagonist listed in Tables 6A-6K for a corresponding neurotransmitter pathway member. In some embodiments, the neurotransmission modulator is a neurotransmission modulator listed in Table 7. Neurotransmission modulators that increase neurotransmission include neurotransmitters and neurotransmitter receptors listed in Tables 4 and 5 and analogs thereof, and neurotransmitter agonists (e.g., small molecules that agonize a neurotransmitter receptor listed in Table 4). Exemplary agonists are listed in Tables 6A-6K. In some embodiments, neurotransmission is increased via administration, local delivery, or stabilization of neurotransmitters (e.g., ligands listed in Tables 4 or 5). Neurotransmission modulators that increase neurotransmission also include agents that increase neurotransmitter synthesis or release (e.g., agents that increase the activity of a biosynthetic protein encoded by a gene in Table 4 via stabilization, overexpression, or upregulation, or agents that increase the activity of a synaptic or vesicular protein via stabilization, overexpression, or upregulation), prevent neurotransmitter reuptake or degradation (e.g., agents that block or antagonize transporters that remove neurotransmitter from the synaptic cleft), increase neurotransmitter receptor activity (e.g., agents that increase the activity of a signaling protein encoded by a gene in Table 4 via stabilization, overexpression, agonism, or upregulation, or agents that upregulate, agonize, or stabilize a neurotransmitter receptor listed in Table 4), increase neurotransmitter receptor synthesis or membrane insertion, decrease neurotransmitter degradation, and regulate neurotransmitter receptor conformation (e.g., agents that bind to a receptor and keep it in an "open" or "primed" conformation). In some embodiments, the neurotransmitter receptor is a channel, the activity of which can be increased by agonizing, opening, stabilizing, or overexpressing the channel. Neurotransmission modulators can increase neurotransmission by 10%, 20%, 30%, 40%, 50%, 60%, 70%, 80%, 90%, 95%, 98% or more. Exemplary neurotransmission modulators are listed in Table 7.

Neurotransmission modulators that decrease neurotransmission include neurotransmitter antagonists (e.g., small molecules that antagonize a neurotransmitter receptor listed in Table 4). Exemplary antagonists are listed in Tables 6A-6K. Neurotransmission modulators that decrease neurotransmission also include agents that decrease neurotransmitter synthesis or release (e.g., agents that decrease the activity of a biosynthetic protein encoded by a gene in Table 4 via inhibition or downregulation, or agents that decrease the activity of a synaptic or vesicular protein via blocking, disrupting, downregulating, or antagonizing the protein), increase neurotransmitter reuptake or degradation (e.g., agents that agonize, open, or stabilize transporters that remove neurotransmitter from the synaptic cleft), decrease neurotransmitter receptor activity (e.g., agents that decrease the activity of a signaling protein encoded by a gene in Table 4 or via blocking or antagonizing the protein, or agents that block, antagonize, or downregulate a neurotransmitter receptor listed in Table 4), decrease neurotransmitter receptor synthesis or membrane insertion, increase neurotransmitter degradation, regulate neurotransmitter receptor conformation (e.g., agents that bind to a receptor and keep it in a "closed" or "inactive" conformation), and disrupt the pre- or postsynaptic machinery (e.g., agents that block or disrupt a structural protein, or agents that block, disrupt, downregulate, or antagonize a synaptic or vesicular protein). In some embodiments, the neurotransmitter receptor is a channel (e.g., a ligand or voltage gated ion channel), the activity of which can be decreased by blockade, antagonism, or inverse agonism of the channel. Neurotransmission modulators that decrease neurotransmission further include agents that sequester, block, antagonize, or degrade a neurotransmitter listed in Tables 4 or 5. Neurotransmission modulators that decrease or block neurotransmission include antibodies that bind to or block the function of neurotransmitters, neurotransmitter receptor antagonists, and toxins that disrupt synaptic release. Neurotransmission modulators can decrease neurotransmission by 10%, 20%, 30%, 40%, 50%, 60%, 70%, 80%, 90%, 95%, 98% or more. Neurotransmission modulator can be administered in any of the modalities described herein (e.g., antibody, small molecule, nucleic acid, polypeptide, or viral vector).

TABLE 4

NEUROTRANSMITTER GENES & PATHWAYS

| Gene | Pathway | Type | Accession Number | Entrez Gene ID |
|---|---|---|---|---|
| ABAT | Neurotransmitter | Biosynthesis | P80404 | 18 |
| ACHE | Neurotransmitter | Biosynthesis | P22303 | 43 |
| ADORA2A | Neurotransmitter | Receptor | P29274 | 135 |
| ADORA2B | Neurotransmitter | Receptor | P29275 | 136 |
| Adra1a | Adrenergic/ Neurotransmitter | Receptor | P35348 | 148 |
| Adra1b | Adrenergic/ Neurotransmitter | Receptor | P35368 | 147 |
| Adra1d | Adrenergic/ Neurotransmitter | Receptor | P25100 | 146 |
| Adra2a | Adrenergic/ Neurotransmitter | Receptor | P08913 | 150 |
| Adra2b | Adrenergic/ Neurotransmitter | Receptor | P18089 | 151 |
| Adra2c | Adrenergic/ Neurotransmitter | Receptor | P18825 | 152 |
| Adrb1 | Adrenergic/ Neurotransmitter | Receptor | P08588 | 153 |
| Adrb2 | Adrenergic/ Neurotransmitter | Receptor | P07550 | 154 |
| Adrb3 | Adrenergic/ Neurotransmitter | Receptor | P13945 | 155 |
| Adrbk1 | Adrenergic | Kinase | P25098 | 156 |
| Adrbk2 | Adrenergic | Kinase | P35626 | 157 |
| BACE1 | Neurotransmitter | Biosynthesis | P56817 | 23621 |
| BCHE | Neurotransmitter | Biosynthesis | P06276 | 590 |
| BRS3 | Neuromodulator | Receptor | P32247 | P32247 |
| C6orf89 | Neuromodulator | Receptor | Q6UWU4 | 221477 |
| CHAT | Neurotransmitter | Biosynthesis | P28329 | 1103 |
| CHRFAM7A | Neurotransmitter | Receptor | Q494W8 | 89832 |
| Chrm1 | Cholinergic/ Neurotransmitter | Receptor | P11229 | 1128 |
| Chrm2 | Cholinergic/ Neurotransmitter | Receptor | P08172 | 1129 |
| Chrm3 | Cholinergic/ Neurotransmitter | Receptor | P20309 | 1131 |
| Chrm4 | Cholinergic/ Neurotransmitter | Receptor | P08173 | 1132 |
| Chrm5 | Cholinergic/ Neurotransmitter | Receptor | P08912 | 1133 |

TABLE 4-continued

NEUROTRANSMITTER GENES & PATHWAYS

| Gene | Pathway | Type | Accession Number | Entrez Gene ID |
|---|---|---|---|---|
| Chrna1 | Cholinergic/Neurotransmitter | Receptor | P02708 | 1134 |
| Chrna10 | Cholinergic/Neurotransmitter | Receptor | Q9GZZ6 | 57053 |
| Chrna2 | Cholinergic/Neurotransmitter | Receptor | Q15822 | 1135 |
| Chrna3 | Cholinergic/Neurotransmitter | Receptor | P32297 | 1136 |
| Chrna4 | Cholinergic/Neurotransmitter | Receptor | P43681 | 1137 |
| Chrna5 | Cholinergic/Neurotransmitter | Receptor | P30532 | 1138 |
| Chrna6 | Cholinergic/Neurotransmitter | Receptor | Q15825 | 8973 |
| Chrna7 | Cholinergic/Neurotransmitter | Receptor | P36544 | 1139 |
| Chrna9 | Cholinergic/Neurotransmitter | Receptor | Q9UGM1 | 55584 |
| Chrnb1 | Cholinergic/Neurotransmitter | Receptor | P11230 | 1140 |
| Chrnb2 | Cholinergic/Neurotransmitter | Receptor | P17787 | 1141 |
| Chrnb3 | Cholinergic/Neurotransmitter | Receptor | Q05901 | 1142 |
| Chrnb4 | Cholinergic/Neurotransmitter | Receptor | P30926 | 1143 |
| Chrnd | Cholinergic/Neurotransmitter | Receptor | Q07001 | 1144 |
| Chrne | Cholinergic/Neurotransmitter | Receptor | Q04844 | 1145 |
| Chrng | Cholinergic/Neurotransmitter | Receptor | P07510 | 1146 |
| CNR1 | Cannabinoid/Neurotransmitter | Receptor | P21554 | 1268 |
| CNR2 | Cannabinoid/Neurotransmitter | Receptor | P34972 | 1269 |
| CNRIP1 | Neurotransmitter | Receptor | Q96F85 | 25927 |
| COMT | Neurotransmitter | Biosynthesis | P21964 | 1312 |
| CPA4 | Neurotransmitter | Biosynthesis | Q9UI42 | 51200 |
| CPE | Neuropeptide/Neurotransmitter | Biosynthesis | P16870 | 1363 |
| CREM | Neurotransmitter | Signaling | Q03060 | 1390 |
| DAGLA | Neurotransmitter (Cannabinoid) | Biosynthesis | Q9Y4D2 | 747 |
| DAGLB | Neurotransmitter (Cannabinoid) | Biosynthesis | Q8NCG7 | 221955 |
| DBH | Neurotransmitter | Biosynthesis | P09172 | 1621 |
| DDC | Neurotransmitter | Biosynthesis | P20711 | 1644 |
| DGKI | Neurotransmitter | Biosynthesis | O75912 | 9162 |
| DOPO | Dopaminergic | Receptor | P09172 | 1621 |
| DPP4 | Neurotransmitter | Biosynthesis | P27487 | 1803 |
| Drd1 | Dopaminergic/Neurotransmitter | Receptor | P21728 | 1812 |
| Drd2 | Dopaminergic/Neurotransmitter | Receptor | P14416 | 1813 |
| Drd3 | Dopaminergic/Neurotransmitter | Receptor | P35462 | 1814 |
| Drd4 | Dopaminergic/Neurotransmitter | Receptor | P21917 | 1815 |
| Drd5 | Dopaminergic/Neurotransmitter | Receptor | P21918 | 1816 |
| ECEL1 | Neurotransmitter | Biosynthesis | O95672 | 9427 |
| FAAH | Neurotransmitter | Biosynthesis | O00519 | 2166 |
| FNTA | Neurotransmitter | Signaling | P49354 | 2339 |
| GABARAP | Neurotransmitter | Receptor | O95166 | 11337 |
| GABARAPL1 | Amine Neuromodulator | Receptor | Q9H0R8 | 23710 |
| GABARAPL2 | Amine Neuromodulator | Receptor | P60520 | 11345 |
| GABBR1 | Neurotransmitter | Receptor | Q9UBS5 | 2550 |
| GABBR2 | Amine Neuromodulator | Receptor | O75899 | 9568 |
| GABRA1 | Neurotransmitter | Receptor | P14867 | 2554 |
| GABRA2 | Neurotransmitter | Receptor | P47869 | 2555 |
| GABRA3 | Neurotransmitter | Receptor | P34903 | 2556 |
| GABRA4 | Neurotransmitter | Receptor | P48169 | 2557 |
| GABRA5 | Neurotransmitter | Receptor | P31644 | 2558 |
| GABRA6 | Neurotransmitter | Receptor | Q16445 | 2559 |
| GABRB1 | Neurotransmitter | Receptor | P18505 | 2560 |
| GABRB2 | Neurotransmitter | Receptor | P47870 | 2561 |
| GABRB3 | Neurotransmitter | Receptor | P28472 | 2562 |
| GABRD | Neurotransmitter | Receptor | O14764 | 2563 |
| GABRE | Neurotransmitter | Receptor | P78334 | 2564 |
| GABRG1 | Neurotransmitter | Receptor | Q8N1C3 | 2565 |
| GABRG2 | Neurotransmitter | Receptor | P18507 | 2566 |
| GABRG3 | Neurotransmitter | Receptor | Q99928 | 2567 |
| GABRP | Neurotransmitter | Receptor | O00591 | 2568 |
| GABRQ | Neurotransmitter | Receptor | Q9UN88 | 55879 |
| GABRR1 | Neurotransmitter | Receptor | P24046 | 2569 |
| GABRR2 | Neurotransmitter | Receptor | P28476 | 2570 |
| GABRR3 | Neurotransmitter | Receptor | A8MPY1 | 200959 |
| GAD1 | Neurotransmitter | Biosynthesis | Q99259 | 2571 |
| GAD2 | Neurotransmitter | Biosynthesis | Q05329 | 2572 |
| GCHFR | Neurotransmitter | Biosynthesis | P30047 | 2644 |
| GLRA1 | Neurotransmitter | Receptor | P23415 | 2741 |
| GLRA2 | Neurotransmitter | Receptor | P23416 | 2742 |
| GLRA3 | Neurotransmitter | Receptor | O75311 | 8001 |
| GLRA4 | Neurotransmitter | Receptor | Q5JXX5 | 441509 |
| GLRB | Neurotransmitter | Receptor | P48167 | 2743 |
| GLS | Neurotransmitter | Biosynthesis | O94925 | 2744 |
| GLS2 | Neurotransmitter | Biosynthesis | Q9UI32 | 27165 |
| GluA1 (GluR1) | Amine Neuromodulator | Receptor | P42261 | 2890 |
| GluK1 (GluR5) | Amine Neuromodulator | Receptor | P39086 | 2897 |
| GLUL | Neurotransmitter | Biosynthesis | P15104 | 2752 |
| GluN1(NR1) | Amine Neuromodulator | Receptor | Q05586 | 2902 |
| GNMT | Neurotransmitter | Biosynthesis | Q14749 | 27232 |
| GPER1 | Neurotransmitter | Receptor | Q99527 | 2852 |
| GPR1 | Neurotransmitter | Receptor | P46091 | 2825 |
| GPR139 | Neurotransmitter | Receptor | Q6DWJ6 | 124274 |
| GPR143 | Neurotransmitter | Receptor | P51810 | 4935 |
| GPR149 | Neurotransmitter | Receptor | Q86SP6 | 344758 |
| GPR18 | Neurotransmitter | Receptor | Q14330 | 2841 |
| GPR21 | Neurotransmitter | Receptor | Q99679 | 2844 |
| GPR26 | Neurotransmitter | Receptor | Q8NDV2 | 2849 |
| GPR3 | Neurotransmitter | Receptor | P46089 | 2827 |
| GPR35 | Neurotransmitter | Receptor | Q9HC97 | 2859 |
| GPR52 | Neurotransmitter | Receptor | Q9Y2T5 | 9293 |
| GPR55 | Neurotransmitter | Receptor | Q9Y2T6 | 9290 |
| GPR78 | Neurotransmitter | Receptor | Q96P69 | 27201 |
| GPR83 | Neurotransmitter | Receptor | Q9NYM4 | 10888 |
| GPR84 | Neurotransmitter | Receptor | Q9NQS5 | 53831 |
| GPRASP1 | Neurotransmitter | Receptor | Q5JY77 | 9737 |
| GPR50 | Amine Neuromodulator | Receptor | Q13585 | 9248 |
| GRIA1 | Neurotransmitter | Receptor | P42261 | 2890 |
| GRIA2 | Neurotransmitter | Receptor | P42262 | 2891 |
| GRIA3 | Neurotransmitter | Receptor | P42263 | 2892 |
| GRIA4 | Neurotransmitter | Receptor | P48058 | 2893 |
| GRID1 | Neurotransmitter | Receptor | Q9ULK0 | 2894 |
| GRID2 | Neurotransmitter | Receptor | O43424 | 2895 |
| GRIK1 | Neurotransmitter | Receptor | P39086 | 2897 |
| GRIK2 | Neurotransmitter | Receptor | Q13002 | 2898 |
| GRIK3 | Neurotransmitter | Receptor | Q13003 | 2899 |
| GRIK4 | Neurotransmitter | Receptor | Q16099 | 2900 |
| GRIK5 | Neurotransmitter | Receptor | Q16478 | 2901 |
| GRIN1 | Neurotransmitter | Receptor | Q05586 | 2902 |
| GRIN2A | Neurotransmitter | Receptor | Q12879 | 2903 |
| GRIN2B | Neurotransmitter | Receptor | Q13224 | 2904 |
| GRIN2C | Neurotransmitter | Receptor | Q14957 | 2905 |
| GRIN2D | Neurotransmitter | Receptor | Q15399 | 2906 |
| GRIN3A | Neurotransmitter | Receptor | Q8TCU5 | 116443 |
| GRIN3B | Neurotransmitter | Receptor | O60391 | 116444 |
| GRK2 | Neurotransmitter | Receptor | P25098 | 156 |
| GRK3 | Neurotransmitter | Receptor | P35626 | 157 |
| GRM1 | Neurotransmitter | Receptor | Q13255 | 2911 |
| GRM2 | Neurotransmitter | Receptor | Q14416 | 2912 |
| GRM3 | Neurotransmitter | Receptor | Q14832 | 2913 |

TABLE 4-continued

NEUROTRANSMITTER GENES & PATHWAYS

| Gene | Pathway | Type | Accession Number | Entrez Gene ID |
|---|---|---|---|---|
| GRM4 | Neurotransmitter | Receptor | Q14833 | 2914 |
| GRM5 | Neurotransmitter | Receptor | P41594 | 2915 |
| GRM6 | Neurotransmitter | Receptor | O15303 | 2916 |
| GRM7 | Neurotransmitter | Receptor | Q14831 | 2917 |
| GRM8 | Neurotransmitter | Receptor | O00222 | 2918 |
| HNMT | Neurotransmitter | Biosynthesis | P50135 | 3176 |
| HOMER1 | Neurotransmitter | Receptor | Q86YM7 | 9456 |
| HRH1 | Neurotransmitter | Receptor | P35367 | 3269 |
| HRH2 | Neurotransmitter | Receptor | P25021 | 3274 |
| HRH3 | Neurotransmitter | Receptor | Q9Y5N1 | 11255 |
| HRH4 | Neurotransmitter | Receptor | Q9H3N8 | 59340 |
| Htr1a | Neurotransmitter | Receptor | P08908 | 3350 |
| Htr1b | Neurotransmitter | Receptor | P28222 | 3351 |
| Htr1c | Neurotransmitter | Receptor | P28335 | |
| Htr1d | Neurotransmitter | Receptor | P28221 | 3352 |
| Htr1e | Neurotransmitter | Receptor | P28566 | 3354 |
| Htr1f | Neurotransmitter | Receptor | P30939 | 3355 |
| Htr2a | Neurotransmitter | Receptor | P28223 | 3356 |
| Htr2b | Neurotransmitter | Receptor | P41595 | 3357 |
| Htr2c | Neurotransmitter | Receptor | P28335 | 3358 |
| Htr3a | Neurotransmitter | Receptor | P46098 | 3359 |
| Htr3b | Neurotransmitter | Receptor | O95264 | 9177 |
| Htr3c | Neurotransmitter | Receptor | Q8WXA8 | 170572 |
| Htr3d | Neurotransmitter | Receptor | Q70Z44 | 200909 |
| HTR3E | Neurotransmitter | Receptor | A5X5Y0 | 285242 |
| Htr4 | Neurotransmitter | Receptor | Q13639 | 3360 |
| Htr5a | Neurotransmitter | Receptor | P47898 | 3361 |
| Htr5b | Neurotransmitter | Receptor | P35365 | 79247 |
| HTR5BP | Neurotransmitter | Receptor | | 645694 |
| Htr6 | Neurotransmitter | Receptor | P50406 | 3362 |
| Htr7 | Neurotransmitter | Receptor | P32305 | 3363 |
| ITPR1 | Neurotransmitter | Signaling | Q14643 | 3708 |
| ITPR2 | Neurotransmitter | Signaling | Q14571 | 3709 |
| ITPR3 | Neurotransmitter | Signaling | Q14573 | 3710 |
| LYNX1 | Neurotransmitter | Receptor | Q9BZG9 | 66004 |
| MAOA | Neurotransmitter | Biosynthesis | P21397 | 4128 |
| MAOB | Neurotransmitter | Biosynthesis | P27338 | 4129 |
| NAMPT | Neurotransmitter | Biosynthesis | P43490 | 10135 |
| NISCH | Neurotransmitter | Receptor | Q9Y2I1 | 11188 |
| NOS1 | Neurotransmitter | Biosynthesis | P29475 | 4842 |
| NPTN | Neurotransmitter | Receptor | Q9Y639 | 27020 |
| P2RX1 | Neurotransmitter | Receptor | P51575 | 5023 |
| P2RX2 | Neurotransmitter | Receptor | Q9UBL9 | 22953 |
| P2RX3 | Neurotransmitter | Receptor | P56373 | 5024 |
| P2RX4 | Neurotransmitter | Receptor | Q99571 | 5025 |
| P2RX5 | Neurotransmitter | Receptor | Q93086 | 5026 |
| P2RX6 | Neurotransmitter | Receptor | O15547 | 9127 |
| P2RX7 | Neurotransmitter | Receptor | Q99572 | 5027 |
| P2RY11 | Neurotransmitter | Receptor | Q96G91 | 5032 |
| PAH | Neurotransmitter | Biosynthesis | P00439 | 5053 |
| PC | Neurotransmitter | Biosynthesis | P11498 | 5091 |
| PDE1B | Neurotransmitter | Signaling | Q01064 | 5153 |
| PDE4A | Neurotransmitter | Signaling | P27815 | 5141 |
| PDE4D | Neurotransmitter | Signaling | Q08499 | 5144 |
| PHOX2A | Neurotransmitter | Biosynthesis | O14813 | 401 |
| PHOX2B | Neurotransmitter | Biosynthesis | Q99453 | 8929 |
| PIK3CA | Neurotransmitter | Signaling | P42336 | 5290 |
| PIK3CB | Neurotransmitter | Signaling | P42338 | 5291 |
| PIK3CG | Neurotransmitter | Signaling | P48736 | 5294 |
| PLCB1 | Neurotransmitter | Signaling | Q9NQ66 | 23236 |
| PLCB2 | Neurotransmitter | Signaling | Q00722 | 5330 |
| PLCB3 | Neurotransmitter | Signaling | Q01970 | 5331 |
| PLCB4 | Neurotransmitter | Signaling | Q15147 | 5332 |
| PLCD1 | Neurotransmitter | Signaling | P51178 | 5333 |
| PLCE1 | Neurotransmitter | Signaling | Q9P212 | 51196 |
| PLCG1 | Neurotransmitter | Signaling | P19174 | 5335 |
| PLCL1 | Neurotransmitter | Signaling | Q15111 | 5334 |
| PLCL2 | Neurotransmitter | Signaling | Q9UPR0 | 23228 |
| PPP1CB | Neurotransmitter | Signaling | P62140 | 5500 |
| PPP100 | Neurotransmitter | Signaling | P36873 | 5501 |
| PRIMA1 | Neurotransmitter | Biosynthesis | Q86XR5 | 145270 |
| PRKACG | Neurotransmitter | Signaling | P22612 | 5568 |
| PRKAR2B | Neurotransmitter | Signaling | P31323 | 5577 |
| PRKCG | Neurotransmitter | Signaling | P05129 | 5582 |
| PRKX | Neurotransmitter | Signaling | P51817 | 5613 |
| RIC3 | Neurotransmitter | Receptor | Q7Z5B4 | 79608 |
| SHANK3 | Neurotransmitter | Signaling | Q9BYB0 | 85358 |
| SLC6A1 | Amine Neuromodulator | Transferase | P30531 | 6529 |
| SLC6A13 | Amine Neuromodulator | Transferase | Q9NSD5 | 6540 |
| Slc6a4 | Serotonin | Transporter | P31645 | 6532 |
| SNX13 | Neurotransmitter | Signaling | Q9Y5W8 | 23161 |
| TAAR1 | Amine Neuromodulator | Receptor | Q96RJ0 | 134864 |
| TAAR2 | Amine Neuromodulator | Receptor | Q9P1P5 | 9287 |
| TAAR5 | Neurotransmitter | Receptor | O14804 | 9038 |
| TH | Neurotransmitter | Biosynthesis | P07101 | 7054 |
| TPH1 | Neurotransmitter | Biosynthesis | P17752 | 7166 |
| TPH2 | Neurotransmitter | Biosynthesis | Q8IWU9 | 121278 |
| TRHDE | Neurotransmitter | Biosynthesis | Q9UKU6 | 29953 |

TABLE 5

NEUROTRANSMITTERS

| Ligand | Pathway | Type |
|---|---|---|
| 2-Arachidonoylglycerol | Endocannabinoid | Ligand |
| 2-Arachidonyl glyceryl ether | Endocannabinoid | Ligand |
| 3-methoxytyramine | Amines | Ligand |
| Acetylcholine | Amino Acids | Ligand |
| Adenosine | Purine | Ligand |
| Adenosine triphosphate | Purine | Ligand |
| Agmatine | Amino Acids | Ligand |
| Anandamide | Endocannabinoid | Ligand |
| Aspartate | Amino Acids | Ligand |
| Carbon monoxide | Gas | Ligand |
| D-serine | Amino Acids | Ligand |
| Dopamine | Monoamines | Ligand |
| Dynorphin | Opioids | Ligand |
| Endorphin | Opioids | Ligand |
| Enkephalin | Opioids | Ligand |
| Epinephrine | Monoamines | Ligand |
| Gamma-aminobutyric acid | Amino Acids | Ligand |
| Glutamate | Amino Acids | Ligand |
| Glycine | Amino Acids | Ligand |
| Histamine | Monoamines | Ligand |
| N-Acetylaspartylglutamate | Neuropeptides | Ligand |
| N-Arachidonoyl dopamine | Endocannabinoid | Ligand |
| N-methylphenethylamine | Amines | Ligand |
| N-methyltryptamine | Amines | Ligand |
| Nitric oxide | Gas | Ligand |
| Norepinephrine | Monoamines | Ligand |
| Octopamine | Amines | Ligand |
| Phenethylamine | Amines | Ligand |
| Serotonin | Monoamines | Ligand |
| Synephrine | Amines | Ligand |
| Tryptamine | Amines | Ligand |
| Tyramine | Amines | Ligand |
| Virodhamine | Endocannabinoid | Ligand |

TABLE 6A

AGONISTS AND ANTAGONIST AGENTS

| Gene | Agonist | Antagonist |
| --- | --- | --- |
| Adrb2<br>Accession Number:<br>P07550 | NCX 950<br>Bitolterol<br>Isoetarine<br>Norepinephrine<br>Phenylpropanolamine<br>Dipivefrin<br>Epinephrine<br>Orciprenaline<br>Dobutamine<br>Ritodrine<br>Terbutaline<br>Salmeterol<br>Formoterol<br>Salbutamol<br>Isoprenaline<br>Arbutamine<br>Arformoterol<br>Fenoterol<br>Pirbuterol<br>Ephedra<br>Procaterol<br>Clenbuterol<br>Bambuterol<br>Indacaterol<br>Droxidopa<br>Olodaterol<br>Vilanterol<br>Pseudoephedrine<br>Cabergoline<br>Mirtazepine | Alprenolol<br>Carvedilol<br>Desipramine<br>Nadolol<br>Levobunolol<br>Metipranolol<br>Bevantolol<br>Oxprenolol<br>Nebivolol<br>Asenapine<br>Bupranolol<br>Penbutolol<br>Celiprolol<br>Pindolol<br>Acebutolol<br>Bopindolol |
| Adra1d<br>Accession Number:<br>P25100 | Midodrine<br>Norepinephrine<br>Clonidine<br>Oxymetazoline<br>Pergolide<br>Bromocriptine<br>Droxidopa<br>Xylometazoline<br>Ergotamine<br>Cirazoline<br>Cabergoline<br>Methoxamine<br>Epinephrine | Dapiprazole<br>Amitriptyline<br>Alfuzosin<br>Promazine<br>Prazosin<br>Imipramine<br>Nortriptyline<br>Doxazosin<br>Nicardipine<br>Dronedarone<br>Tamsulosin<br>Propiomazine<br>Phenoxybenzamine<br>Carvedilol<br>Doxepin<br>Terazosin<br>Quetiapine<br>Methotrimeprazine<br>Silodosin |
| Adrb1<br>Accession Number:<br>P08588 | Isoetarine<br>Norepinephrine<br>Phenylpropanolamine<br>Epinephrine<br>Dobutamine<br>Salbutamol<br>Isoprenaline<br>Arbutamine<br>Fenoterol<br>Pirbuterol<br>Ephedra<br>Clenbuterol<br>Droxidopa<br>Pseudoephedrine<br>Carteolol<br>Cabergoline<br>Mirtazapine<br>Loxapine<br>Vortioxetine<br>Desipramine | Esmolol<br>Betaxolol<br>Metoprolol<br>Atenolol<br>Timolol<br>Sotalol<br>Propranolol<br>Labetalol<br>Bisoprolol<br>Alprenolol<br>Amiodarone<br>Carvedilol<br>Nadolol<br>Levobunolol<br>Metipranolol<br>Bevantolol<br>Practolol<br>Oxprenolol<br>Celiprolol<br>Nebivolol<br>Asenapine<br>Bupranolol<br>Penbutolol<br>Pindolol<br>Acebutolol<br>Bopindolol<br>Cartelol |

TABLE 6A-continued

AGONISTS AND ANTAGONIST AGENTS

| Gene | Agonist | Antagonist |
|---|---|---|
| Adrb3<br>Accession Number:<br>P13945 | SR 58611<br>Norepinephrine<br>Epinephrine<br>Isoprenaline<br>Arbutamine<br>Fenoterol<br>Ephedra<br>Clenbuterol<br>Droxidopa<br>Mirabegron | Bopindolol<br>Propranolol<br>Bupranolol |
| Adrbk1<br>Accession Number:<br>P25098 | ATP<br>Carbachol<br>Dopamine<br>Isoproterenol<br>Morphine<br>DAMGO<br>histamine<br>Acetylcholine<br>Etorphine<br>NMDA | Alprenolol<br>Heparin |
| Adrbk2<br>Accession Number:<br>P26819 | Dopamine<br>Isoproterenol<br>DAMGO<br>ATP | Propranolol |
| Chrm3<br>Accession Number:<br>P20309 | cgmp<br>ATP<br>Cevimeline<br>arecoline<br>oxotremorine-M<br>NNC 11-1314<br>xanomeline<br>oxotremorine<br>pentylthio-TZTP<br>arecaidine propargyl ester<br>NNC 11-1607<br>furmethide<br>NNC 11-1585<br>Acetylcholine<br>methylfurmethide<br>Bethanechol<br>Carbachol<br>Succinylcholine<br>ALKS 27<br>itopride<br>methacholine<br>Meperidine<br>Cinnarizine<br>Trimipramine | MT3<br>Hexocyclium<br>Himbacine<br>Biperiden<br>lithocholylcholine<br>AFDX384<br>4-DAMP<br>hexahydrodifenidol<br>VU0255035<br>N-methyl scopolamine<br>Darifenacin<br>Thiethylperazine<br>methoctramine<br>silahexocyclium<br>Strychnine<br>MT7<br>Heparin<br>Olanzapine<br>Pirenzepine<br>Clidinium<br>Ipratropium<br>Propantheline<br>Dicyclomine<br>Darifenacin<br>Tiotropium<br>Atropine<br>Scopolamine<br>Amitriptyline<br>Doxepin<br>Lidocaine<br>Nortriptyline<br>Tropicamide<br>Metixene<br>Homatropine Methylbromide<br>Solifenacin<br>Glycopyrrolate<br>Propiomazine<br>Diphemanil Methylsulfate<br>Promethazine<br>Diphenidol<br>Pancuronium<br>Ziprasidone<br>Quetiapine<br>Imipramine<br>Clozapine<br>Cyproheptadine<br>Aripiprazole<br>Nicardipine<br>Amoxapine<br>Loxapine<br>Promazine<br>Oxyphencyclimine |

TABLE 6A-continued

AGONISTS AND ANTAGONIST AGENTS

| Gene | Agonist | Antagonist |
|---|---|---|
| | | Anisotropine Methylbromide |
| | | Tridihexethyl |
| | | Chlorpromazine |
| | | Ketamine |
| | | Cyclosporin A |
| | | Paroxetine |
| | | Benzquinamide |
| | | Tolterodine |
| | | Oxybutynin |
| | | Alcuronium |
| | | WIN 62, 577 |
| | | Tramadol |
| | | Chlorprothixene |
| | | Aclidinium |
| | | Methotrimeprazine |
| | | Umeclidinium |
| | | Cryptenamine |
| | | Mepenzolate |
| | | Maprotiline |
| | | Brompheniramine |
| | | Isopropamide |
| | | Trihexyphenidyl |
| | | Ipratropium bromide |
| | | Hyoscyamine |
| | | Procyclidine |
| | | Pipecuronium |
| | | Fesoterodine |
| | | Disopyramide |
| | | Desipramine |
| | | Mivacurium |
| Chrna3 Accession Number: P32297 | Nicotine Varenicline Acetylcholine Ethanol Cytisine Levamisole Galantamine | A-867744 NS1738 Hexamethonium Mecamylamine Dextromethorphan Pentolinium Levomethadyl Acetate Bupropion |
| Chrna6 Accession Number: Q15825 | Nicotine Cytisine Varenicline Galantamine | Hexamethonium Mecamylamine |
| Chrna9 Accession Number: Q9UGM1 | Nicotine Galantamine Ethanol ATG003 Lobeline RPI-78M | Hexamethonium Mecamylamine Tetraethylammonium Muscarine Strychnine |
| Chrnb1 Accession Number: P11230 | Galantamine | |
| Chrnb4 Accession Number: P30926 | Nicotine Varenicline PNU-120596 Ethanol Galantamine | Atropine Oxybutynin Pentolinium Dextromethorphan |
| Chrng Accession Number: P07510 | Galantamine | |
| Adcyap1 Accession Number: P18509 | Nicotine CGMP Apomorphine Suramin Nifedipine ATP Dihydrotestosterone Maxadilan Dexamethasone Acetylcholine Histamine Carbachol NMDA | Atropine PPADS Onapristone Muscarine Haloperidol Astressin Melatonin Scopolamine Tetrodotoxin Apamin Hexamethonium Indomethacin Propranolol |

TABLE 6A-continued

AGONISTS AND ANTAGONIST AGENTS

| Gene | Agonist | Antagonist |
|---|---|---|
| | Dopamine | Bumetanide |
| | Isoproterenol | Progesterone |
| | Salbutamol | Charybdotoxin |
| | Morphine | Prazosin |
| | Clonidine | |
| | Nimodipine | |
| | 2,6-Diamino-Hexanoic Acid Amide | |
| CYSLTR1 | Salbutamol | Montelukast |
| Accession Number: | Dexamethasone | Zafirlukast |
| Q9Y271 | Arachidonic acid | Cinalukast |
| | Histamine | Pranlukast |
| | | Nedocromil |
| | | Theophylline |
| | | Indomethacin |
| | | Zileuton |
| | | Iralukast |
| | | Pobilukast |
| | | Sulukast |
| | | Verlukast |
| LTB4R | LTB | U75302 |
| Accession Number: | ATP | CP105696 |
| Q15722 | Dexamethasone | CP-195543 |
| | cholesterol | Etalocib |
| | 20-hydroxy-LTB< | SC-41930 |
| | 12R-HETE | LY255283 |
| | arachidonic acid | Zafirlukast |
| | | ONO-4057 |
| | | RO5101576 |
| | | BILL 260 |
| PENK | Dopamine | Naltrexone |
| Accession Number: | kainate | Naloxone |
| P01210 | NMDA | Progesterone |
| | DAMGO | |
| | Morphine | |
| Htr2c | Apomorphine | Melatonin |
| Accession Number: | Bifeprunox | SB 224289 |
| P28335 | Tramadol | LY334362 |
| | AL-37350A | FR260010 |
| | 5-MeO-DMT | Sulpiride |
| | BW723C86 | Thiethylperazine |
| | CGS-12066 | cyamemazine |
| | DOI | Mesulergine |
| | 5-CT | SB 221284 |
| | YM348 | Zotepine |
| | LSD | Metergoline |
| | xanomeline | methiothepin |
| | WAY-163909 | Spiperone |
| | Dopamine | SB 215505 |
| | LY344864 | Tiospirone |
| | VER-3323 | SB 228357 |
| | TFMPP | Pizotifen |
| | 8-OH-DPAT | SB 206553 |
| | MK-212 | SB 204741 |
| | NMDA | SDZ SER-082 |
| | org 12962 | Ritanserin |
| | 5-MeOT | SB 242084 |
| | RU 24969 | S33084 |
| | Acetylcholine | Roxindole |
| | QUINPIROLE | RS-127445 |
| | quipazine | Terguride |
| | tryptamine | EGIS-7625 |
| | Ro 60-0175 | SB 243213 |
| | Oxymetazoline | RS-102221 |
| | Ergotamine | Olanzapine |
| | Cabergoline | Aripiprazole |
| | Lorcaserin | Agomelatine |
| | Pergolide | Ziprasidone |
| | Methylergonovine | Quetiapine |
| | Renzapride | Sarpogrelate |
| | Pramipexole | Perphenazine |
| | GR-127935 | Thioridazine |
| | BRL-15572 | Sertindole |
| | ipsapirone | Loxapine |
| | SB 216641 | Methysergide |
| | SL65.0155 | Risperidone |
| | S 16924 | Asenapine |

TABLE 6A-continued

| AGONISTS AND ANTAGONIST AGENTS | | |
|---|---|---|
| Gene | Agonist | Antagonist |
| | Bromocriptine | Mianserin |
| | Lisuride | Clozapine |
| | Tegaserod | Trifluoperazine |
| | Epicept NP-1 | Trazodone |
| | dapoxetine | Doxepin |
| | Dexfenfluramine | Nortriptyline |
| | 3,4-Methylenedioxymethamphetamine | Chlorprothixene |
| | Ropinirole | Minaprine |
| | Maprotiline | Propiomazine |
| | Desipramine | Mirtazapine |
| | | Amoxapine |
| | | Yohimbine |
| | | Cyproheptadine |
| | | Imipramine |
| | | Amitriptyline |
| | | Promazine |
| | | Chlorpromazine |
| | | Ketamine |
| | | Propranolol |
| | | Fluoxetine |
| | | Ketanserin |
| | | Mesulergine |
| | | AC-90179 |
| | | Ergoloid mesylate 2 |
| | | Methotrimeprazine |
| | | Paliperidone |
| | | Clomipramine |
| | | Trimipramine |
| | | Captodiame |
| | | Nefazodone |
| GABA Receptor Accession Numbers (Q9UBS5, O95166, O75899, P28472, P18507, P47870, P47869, O14764) | Bamaluzole | bicuculline |
| | GABA | Metrazol |
| | Gabamide | Flumazenil |
| | GABOB | Thiothixine |
| | Gaboxadol | Bupropion |
| | Ibotenic acid | Caffeine |
| | Isoguvacine | |
| | Isonipecotic acid | |
| | Muscimol | |
| | Phenibut | |
| | Picamilon | |
| | Progabide | |
| | Quisqualamine | |
| | SL 75102 | |
| | Thiomuscimol | |
| | Alcohols (e.g., ethanol, isopropanol) | |
| | Avermectins (e.g., ivermectin) | |
| | Barbiturates (e.g., phenobarbital) | |
| | Benzodiazepines | |
| | Bromides (e.g., potassium bromide | |
| | Carbamates (e.g., meprobamate, carisoprodol) | |
| | Chloralose | |
| | Chlormezanone | |
| | Clomethiazole | |
| | Dihydroergolines (e.g., ergoloid (dihydroergotoxine)) | |
| | Etazepine | |
| | Etifoxine | |
| | Imidazoles (e.g., etomidate) | |
| | Kavalactones (found in kava) | |
| | Loreclezole | |
| | Neuroactive steroids (e.g., allopregnanolone, ganaxolone) | |
| | Nonbenzodiazepines (e.g., zaleplon, zolpidem, zopiclone, eszopiclone) | |
| | Petrichloral | |
| | Phenols (e.g., propofol) | |
| | Piperidinediones (e.g., glutethimide, methyprylon) | |
| | Propanidid | |
| | Pyrazolopyridines (e.g., etazolate) | |
| | Quinazolinones (e.g., methaqualone) | |

TABLE 6A-continued

AGONISTS AND ANTAGONIST AGENTS

| Gene | Agonist | Antagonist |
|---|---|---|
| | Skullcap constituents | |
| | Stiripentol | |
| | Sulfonylalkanes (e.g., sulfonmethane, tetronal, trional) | |
| | Valerian constituents (e.g., valeric acid, valerenic acid) | |
| | Volatiles/gases (e.g., chloral hydrate, chloroform, diethyl ether, sevoflurane) | |
| Glutamate Receptor Accession Number: (P42261, P39086, P39086, Q13585, P42261, P42262, P42263, P48058, P39086, Q13002, Q13003, Q13003, Q16478, Q12879, Q14957, Q13224, Q14957, Q15399, Q8TCU5, O60391) | 3,5-dihydroxyphenylglycine eglumegad Biphenylindanone A DCG-IV L-AP4 | APICA EGLU LY-341, 495 |
| CNR1/CNR2 Accession Number: (P21554, P34972) | N-Arachidonoylethanolamine 2-Arachidonoyl-glycerol 2-Arachidonoyl-glycerylether N-Arachidonoyl-dopamine O-Arachidonoyl-ethanolamine N-Arachidonoylethanolamine 2-Arachidonoyl-glycerol 2-Arachidonoyl-glycerylether N-Arachidonoyl-dopamine O-Arachidonoyl-ethanolamine Δ-9-THC CP-55, 940 R(+)-WIN 55, 212-2 HU-210 Levonantradol Nabilone Methanandamide ACEA O-1812 Δ9-THC CP-55, 940 R(+)-WIN 55, 212-2 HU-210 Levonantradol Nabilone Methanandamide JWH-015 JWH-133 | SR 141716A LY-320135 AM251 AM281 SR 144528 AM630 |

TABLE 6B

ADRENERGIC AGONISTS AND ANTAGONISTS

| Receptor | Agonist | Antagonist |
|---|---|---|
| Non-selective | adrenaline (epinephrine), noradrenaline (norepinephrine), isoprenaline (isoproterenol), dopamine, caffeine, nicotine, tyramine, methylphenidate, ephedrine and pseudophedrine. | carvedilol, arotinolol, and labetalol |
| α1 selective (ADRA1A, ADRA1B, ADRA1D) | phenylephrine, methoxamine, midodrine, cirazoline, xylometazoline, metaraminol chloroehtylclonidine, oxymetazoline | acepromazine, alfuzosin, doxazosin, labetalol, phenoxybenzamine, KW3902, phentolamine, prazosin, tamsulosin, terazosin, tolazoline, trazodone, amitriptyline, silodosin, clomipramine, doxepin, trimipramine, typical and atypical antipsychotics, and antihistamines, such as hyroxyzine |

TABLE 6B-continued

| ADRENERGIC AGONISTS AND ANTAGONISTS | | |
|---|---|---|
| Receptor | Agonist | Antagonist |
| α2 selective (ADRA2A, ADRA2B, ADRA2C) | α-methyl dopa, clonidine, brimonidine, agmatine, dexmedetomidine, medetomidine, romifidine chloroethylclonidine, detomidine, lofexidine, xylazine, tizanidine, guanfacine, and amitraz | phentolamine, phenoxybenzamine, yohimbine, idazoxan, atipamezole, mirtazapine, tolazoline, trazodone, and typical and atypical antipsychotics |
| β1 selective (ADRB1) | Dobutamine | metroprolol, atenolol, acebutolol, bisoprolol, betaxolol, levobetaxolol, esmolol, celiprolol, carteolol, landiolol, oxprenolol, propanolol, practolol, penbutolol, timolol, labetalol, nebivolol, levobunolol, nadolol, pindolol, sotalol, metipranolol, tertatolol, vortioxene |
| β2 selective (ADRB2) | salbutamol, albuterol, bitolterol mesylate, levabuterol, ritodrine, metaproterenol, terbutaline, salmeterol, formoterol, and pirbuterol | butaxamine, acebutolol, timolol, propanolol, levobunolol, carteolol, labetalol, pindolol, oxprenolol, nadolol, metipranolol, penbutolol, tertatolol, sotalol |
| β3 selective (ADRB3) | L-796568, amibegron, solabegron, mirabegron | SR 59230A, arotinolol |

TABLE 6C

| DOPAMINE AGONISTS AND ANTAGONISTS | | |
|---|---|---|
| Receptor | Agonist | Antagonist |
| Non-selective | pramipexole, ropinirole, rotigotine, apomorphine, propylnorapomorphine, bromocriptine, cabergoline, ciladopa, dihydrexidine, dinapsoline, doxamthrine, epicriptine, lisuride, pergolide, piribedil, quinagolide, roxindole, dopamine | haloperidol, paliperidone, clozapine, risperidone, olanzapine, quetiapine, ziprasidone, metoclopramide, droperidol, domperidone, amoxapine, clomipramine, trimipramine, choline, melatonin, acepromazine, amisulpride, asenapine, azaperone, benperidol, bromopride, butaclamol, chlorpromazine, clebopride, chlorprothixene, clopenthixol, clocapramine, eticlopride, flupenthixol, fluphenazine, fluspirilene, hydroxyzine, itopride, iodobenzamide, levomepromazine, levosulpiride, loxapine, mesoridazine, metopimazine, mosapramine, nafadotride, nemonapride, penfluridol, perazine, perphenazine, pimozide, prochlorperazine, promazine, pipotiazine, raclopride, remoxipride, spiperone, spiroxatrine, stepholidine, sulpiride, sultopride, tetrahydropalmatine, thiethylperazine, thioridazine, thiothixene, tiapride, trifluoperazine, trifluperidol, triflupromazine, thioproperazine, taractan, zotepine, zuclopenthixol, ziprasidone, ANP-010, NGD-94-4 |
| D1 (DRD1) | Fenoldopam, A-86929, dihydrexidine, dinapsoline, dinoxyline, doxanthrine, SKF-81297, SKF-82958, SKF-38393, G-BR-APB, dopexamine | SCH-23,390, SKF-83,959, Ecopipam, Clebopride, Flupenthixol, Zuclopenthixol, Taractan, PSYRX-101, LuAF-35700, GLC-756, ADX10061, Zicronapine |
| D2 (DRD2) | Cabergoline, pergolide, quinelorane, sumanirole, talipexole, piribedil, quinpirole, quinelorane, dinoxyline, dopexamine | Chloroethylnorapomorphine, desmethoxyfallypride, domperidone, eticlopride, fallypride, hydroxyzine, itopride, L-741,626, SV 293, yohimbine, raclopride, sulpiride, paliperidone, penfluridol, quetiapine, lurasidone, risperidone, olanzapine, blonanserin, perphenazine, metoclopramide, trifluoperazine, clebopride, levosulpiride, flupenthixol, haloperidol, thioridazine, alizapride, |

TABLE 6C-continued

DOPAMINE AGONISTS AND ANTAGONISTS

| Receptor | Agonist | Antagonist |
|---|---|---|
| | | amisulpride, asenapine, bromopride, bromperidol, clozapine, fluphenazine, perphanazine, loxapine, nemonapride, pericyazine, pipamperone, prochlorperazine, thioproperazine, thiethylperazine, tiapride, ziprasidone, zuclopenthixol, taractan, fluanisone, melperone, molindone, remoxipride, sultopride, ALKS 3831, APD-403, ONC201, pridopidine, DSP-1200, NG-101, TAK-906, ADN-1184, ADN-2013, AG-0098, DDD-016, IRL-626, KP303, ONC-206, PF-4363467, PGW-5, CG-209, ABT-925, AC90222, ACP-005, ADN-2157, CB030006, CLR-136, Egis-11150, Iloperidone, JNJ-37822681, DLP-115, AZ-001, S-33138, SLV-314, Y-931, YKP1358, YK-P1447, APD405, CP-903397, ocaperidone, zicronapine, TPN-902 |
| D3 (DRD3) | Piribedil, quinpirole, captodiame, compound R, R-16, FAUC 54, FAUC 73, PD-128,907, PF-219,061, PF-592,379, CJ-1037, FAUC 460, FAUC 346, cariprazine | Domperidone, FAUC 365, nafadotride, raclopride, PNU-99,194, SB-277011-A, sulpiride, risperidone, YQA14, U99194, SR 21502, levosulpiride, amisulpride, nemonapride, ziprasidone, taractan, sultopride, APD-403, F17464, ONC201, NG-101, TAK-906, ONC-206, PF-4363467, ABT-127, ABT-614, GSK-598809, GSK-618334, S-14297, S-33138, YKP1358, YK-P1447 |
| D4 (DRD4) | WAY-100635, A-412,997, ABT-724, ABT-670, FAUC 316, PD-168, 077, CP-226,269 | A-381393, FAUC 213, L-745,870, L-570,667, ML-398, fananserin, clozapine, PNB-05, SPI-376, SPI-392, Lu-35-138, NGD-94-1 |
| D5 (DRD5) Partial | Dihydrexidine, rotigotine, SKF-83,959, fenoldopam, aplindore, brexpiprazole, aripiprazole, CY-208,243, pardoprunox, phencyclidine, and salvinorin A | SCH 23390 |

TABLE 6D

GABA AGONISTS AND ANTAGONISTS

| Receptor | Agonist | Antagonist |
|---|---|---|
| GABA$_A$ | barbiturates (e.g., allobarbital, amobarbital, aprobarbital, alphenal, barbital, brallobarbital, phenobarbital, secobarbital, thiopental), bamaluzole, GABA, GABOB, gaboxadol, ibotenic acid, isoguvacine, isonipecotic acid, muscimol, phenibut, picamilon, progabide, quisqualamine, SL 75102, thiomuscimol, positive allosteric modulators (PAMs) (e.g., alcohols, such as ethanol and isopropanol; avermectins, such as ivermectin; benzodiazepines, such as diazepam, alprazolam, chlordiazepoxide, clonazepam, flunitrazepam, lorazepam, midazolam, oxazepam, prazepam, brotizolam, triazolam, estazolam, lormetazepam, nitrazepam, temazepam, flurazepam, clorazepate halazepam, prazepam, nimetazepem, adinazolam, and climazolam; bromides, such as potassium bromide; carbamates, such as meprobamate and carisoprodol; chloralose; | bicuculline, gabazine, hydrastine, pitrazepin, sinomenine, tutin, thiocolchicoside, metrazol, securinine, gabazine |

TABLE 6D-continued

GABA AGONISTS AND ANTAGONISTS

| Receptor | Agonist | Antagonist |
|---|---|---|
| | chlormezanone; chlomethiazole; dihydroergolines, such as ergoloid; etazepine; etifoxine; imidazoles, such as etomidate; imidazopyridines, such as alpidem and necopdiem; kavalactones; loreclezole; neuroactive steroids, such as allogregnanolone, pregnanolone, dihydrodeoxycorticosterone, tetrahydrodeoxycortisosterone, androstenol, androsterone, etiocholanolone, 3α-androstanediol, 5α, 5β, or 3α-dihydroprogesterone, and ganaxolone; nonbenzodiazepines, such as zalepon, zolpidem, zopiclone, and eszopiclone; petrichloral; phenols, such as propofol; piperidinediones, such as glutethimide and methyprylon; propanidid; pyrazolopyridines, such as etazolate; pyrazolopyrimidines, such as divaplon and fasiplon; cyclopyrrolones, sush as pagoclone and suproclone; β-cabolines, such as abecarnil and geodecarnil; quinazolinones, such as methaqualone; *Scutellaria* constituents; stiripentol; sulfonylalkanes, such as sulfonomethane, teronal, and trional; Valerian constituents, such as valeric acid and valerenic acid; and gases, such as chloral hydrate, chloroform, homotaurine, diethyl ether, and sevoflurane. | |
| $GABA_B$ | 1,4-butanediol, baclofen, GABA, Gabamide, GABOB, gamma-butyrolactone, gamma-hydroxybutyric acid, gamma-hyrdoxyvaleric acid, gamma-valerolactone, isovaline, lesogaberan, phenibut, picamilon, progabide, homotaurine, SL-75102, tolgabide | CGP-35348, homotaurine, phaclofen, saclofen, and SCH-50911 |
| $GABA_A$-p | CACA, CAMP, GABA, GABOB, N4-chloroacetylcytosine arabinoside, picamilon, progabide, tolgabide, and neuroactive steroids, such as allopregnanolone, THDOC, and alphaxol one | gabazine, gaboxadol, isonipecotic acid, SKF-97,541, and (1,2,5,6-Tetrahydropyridin-4-yl)methylphosphinic acid |

TABLE 6E

MUSCARINC AGONISTS AND ANTAGONISTS

| Receptor | Agonist | Antagonist |
|---|---|---|
| Chrm1 | AF102B, AF150(S), AF267B, acetylcholine, carbachol, cevimeline, muscarine, oxotremorine, pilocarpine, vedaclidine, 77-LH-28-1, CDD-0097, McN-A-343, L689,660, and xanomeline | atropine, dicycloverine, hyoscyamine, ipratropium, mamba toxin muscarinic toxin 7 (MT7), olanzapine, oxybutynin, pirenzepine, telenzepine, and tolterodine |
| Chrm2 | acetylcholine, methacholine, iper-8-naph, berbine, and (2S,2'R,3'S,5'R)-1-methyl-2-(2-methyl-1,3-oxathiolan-5-yl)pyrrolidine 3-sulfoxide methyl iodide | atropine, dicycloverine, hyoscyamine, otenzepad, AQRA-741, AFDX-384, thorazine, diphenhydramine, dimenhydrinate, ipratropium, oxybutynin, pirenzepine, methoctramine, tripitramine, gallamine, and tolterodine |

TABLE 6E-continued

MUSCARINC AGONISTS AND ANTAGONISTS

| Receptor | Agonist | Antagonist |
|---|---|---|
| Chrm3 | acetylcholine, bethanechol, carbachol, L689, 660, oxotremorine, pilocarpine, aceclidine, arecoline, and cevimeline | atropine, dicycloverine, hyoscyamine, alcidium bromide, 4-DAMP, darifenacin, DAU-5884, HL-031,120, ipratropium, J-104,129, oxybutynin, tiotropium, zamifenacin, and tolterodine |
| Chrm4 | acetylcholine, carbachol, and oxotremorine), and Chrm5 agonists (e.g., acetylcholine, milameline, sabcomeline | AFDX-384, dicycloverine, himbacine, mamba toxin 3, PD-102,807, PD-0298029, and tropicamide |
| Chrm5 | acetylcholine, milameline, sabcomeline | VU-0488130, xanomeline |
| Non-selective | | scopolamine, hydroxyzine, doxylamine, dicyclomine, flavoxate, cyclopentolate, atropine methonitrate, trihexyphenidyl/benzhexol, solifenacin, benzatropine, mebeverine, and procyclidine |

TABLE 6F

NICOTINIC AGONISTS AND ANTAGONISTS

| Receptor | Agonist | Antagonist |
|---|---|---|
| Chrna receptors | choline, acetylcholine, carbachol, methacholine, nicotine, varenicline tartrate, galantamine hydrobromide, suxamethonium chloride (succinylcholine chloride), epibatidine, iobeline, decamethonium, isopronicline/TC-1734/AZD3480 (TC-1734), AZD1446 (TC-6683), TC-5619, TC-5214, MEM 3454 (RG3487), ABT-894, ABT-560, EVP-6124, EVP-4473, PNU-282987, AR-R17779, SSR 189711, JN403, ABBF, PHA-543613, SEN12333, GTS-21/DMXB-A, AZD0328, A-582941, ABT-418, 5-iodo-A-85380, SIB-1765F, ABT-089, and ABT-594 | turbocurarine, bupropion, mecamylamine, 18-methozycoronaridine, hexamethonium, trimethaphan, atraciurium, doxacurium, mivacurium, pancuronium, vecuronium, succinylcholine, dextromethorphan, neramexane, dextrophan, and 3-methoxymorphinan |

TABLE 6G

SEROTONIN AGONISTS AND ANTAGONISTS

| Receptor | Agonist | Antagonist |
|---|---|---|
| 5-HT$_{1A}$ | azapirones, such as alnespirone, binosperone, buspirone, enilospirone, etaperone, geprione, ipsaprione, revospirone, zalospirone, perospirone, tiosperone, umespirone, and tandospirone; 8-OH-DPAT, befiradol, F-15,599, lesopitron, MKC-242, LY-283,284, osemozotan, repinotan U-92,016-A, RU-24969, 2C-B, 2C-E, 2C-T-2, aripiprazole, asenapine, bacoside, befiradol, brexpiprazole, bufotenin, cannabidiol, and fibanserin | pindolol, tertatolol, alprenolol, AV-965, BMY-7,378, cyanopindolol, dotarizine, flopropione, GR-46,611, iodocyanopindolol, isamoltane, lecozotan, mefway, methiothepin, methysergide, MPPF, NAN-190, oxprenolol, pindobind, propanolol, risperidone, robalzotan, SB-649,915, SDZ-216,525, spiperone, spiramide, spiroxatrine, UH-301, WAY-100,135, WAY-100,635, and xylamidine |

TABLE 6G-continued

SEROTONIN AGONISTS AND ANTAGONISTS

| Receptor | Agonist | Antagonist |
|---|---|---|
| $5\text{-}HT_{1B}$ | triptans, such as sumatriptan, rizatriptan, eletriptan, donitriptan, almotriptan, frovatriptan, avitriptan, zolmitriptan, and naratriptan; ergotamine, 5-carboxamidotryptamine, CGS-12066A, CP-93,129, CP-94,253, CP-122,288, CP-135,807, RU-24969, vortioxetine, ziprasidone, and asenapine | methiothepin, yohimbine, metergoline, aripiprazole, isamoltane, AR-A000002, SB-216,641, SB-224,289, GR-127,935, SB-236,057 |
| $5\text{-}HT_{1D}$ | triptans, such as sumatriptan, rizatriptan, and naratriptan; ergotamine, 5-(nonyloxy)tryptaime, 5-(t-butyl)-N-methyltryptamine, CP-286,601, PNU-109,291, PNU-142,633, GR-46611, L-694,247, L-772,405, CP-122,288, and CP-135,807 | ziprasidone, methiothepin, yohimbine, metergoline, ergotamine, BRL-15572, vortioxetine, GR-127,935, LY-310,762, LY-367,642, LY-456,219, and LY-456,220 |
| $5\text{-}HT_{1E}$ | BRL-54443, eletriptan | |
| $5\text{-}HT_{1F}$ | LY-334,370, 5-n-butyryloxy-DMT, BRL-54443, eletriptan, LY-344,864, naratriptan, and lasmiditan | |
| $5\text{-}HT_{2A}$ | 25I-NBOH, 25I-NBOMe, (R)-DOI, TCB-2, mexamine, O-4310, PHA-57378, OSU-6162, 25CN-NBOH, juncosamine, efavirenz, mefloquine, lisuride, and 2C-B | cyproheptadine, methysergide, quetiapine, nefazodone, olanzapine, asenapine, pizotifen, LY-367,265, AMDA, hydroxyzine, 5-MeO-NBpBrT, and niaprazine |
| $5\text{-}HT_{2B}$ | fenfluramine, pergolide, cabergoline, mefloquine, BW-723086, Ro60-0175, VER-3323, 6-APB, guanfacine, norfenfluramine, 5-MeO-DMT, DMT, mCPP, aminorex, chlorphentermine, MEM, MDA, LSD, psilocin, MDMA | agomelatine, aripiprazole, sarpogrelate, lisuride, tegaserod, metadoxine, RS-127,445, SDZ SER-082, EGIS-7625, PRX-08066, SB-200,646, SB-204,741, SB-206,553, SB-215,505, SB-228,357, LY-266,097, and LY-272,015 |
| $5\text{-}HT_{2C}$ | lorcaserin, lisuride, A-372,159, AL-38022A, CP-809,101, fenfluramine, mesulergine, MK-212, naphthyllisopropylamine, norfenfluramine, ORG-12,962, ORG-37,684, oxaflozane, PNU-22395, PNU-181731, lysergamides, phenethylamines, piperazines, tryptamines, Ro60-0175, vabicaserin, WAY-629, WAY-161,503, WAY-163,909, and YM-348 | agomelatine, CPC, eltoprazine, etoperidone, fluoxetine, FR-260,010, LU AA24530, methysergide, nefazodone, norfluoxetine, O-desmethyltramadol, RS-102,221, SB-200,646, SB-221,284, SB-242,084, SDZ SER-082, tramadol, and trazodone |
| $5\text{-}HT_{2A/2C}$ | | ketanserin, risperidone, trazodone, mirtazapine, clozapine |
| $5\text{-}HT_3$ | 2-methyl-5-HT, alpha-methyltryptamine, bufotenin, chlorophenylbiguanide, ethanol, ibogaine, phenylbiguanide, quipazine, RS-56812, SR-57227, varenicline, and YM-31636 | dolasetron, granisetron, ondansetron, palonosetron, tropisetron, alosetron, cilanosetron, mirtazapine, AS-8112, bantopride, metroclopramide, renzapride, zacopride, mianserin, vortioxetine, clozapine, olanzapine, quetiapine, menthol, thujone, lamotigrine, and 3-tropanyl indole-3-carboxylate |
| $5\text{-}HT_4$ | cisapride, tegaserod, prucalopride, BIMU-8, CJ-033,466, ML-10302, mosapride, renzapride, RS-67506, RS-67333, SL65.1055, zacopride, metoclopramide, and sulpride | piboserod, GR-113,808, GR-125,487, RS-39604, SB-203,186, SB-204,070, and chamomile |
| $5\text{-}HT_{5A}$ | valeronic acid | ASP-5736, AS-2030680, AS-2674723, latrepiridine, risperidone, and SB-699,551 |
| $5\text{-}HT_6$ | EMDT, WAY-181,187, WAY-208,466, N-(inden-5-yl)imidazothiazole-5-sulfonamide, E-6837, E-6801, and EMD-386,088 | ALX-1161, AVN-211, BVT-5182, BVT-74316, cerlapiridine, EGIS-12233, idalopiridine, interpridine, latrepiridine, MS-245, PRX-07034, SB-258,585, SB-271,046, SB-357,134, SB-339,885, Ro 04-6790, Ro-4368554, sertindole, olanzapine, asenapine, clozapine, rosa rugosa extract, and WAY-255315 |

TABLE 6G-continued

SEROTONIN AGONISTS AND ANTAGONISTS

| Receptor | Agonist | Antagonist |
|---|---|---|
| $5\text{-HT}_7$ | AS-19, 5-CT, 5-MeOT, 8-OH-DAPT, aripiprazole, E-55888, E-57431, LP-12, LP-44, MSD-5a, RA-7, and N,N-Dimethyltryptamine | amisulpride, amitriptyline, amoxapine, clomipramine, clozapine, DR-4485, fluphenazine, fluperlapine, ICI 169,369, imipramine, ketanserine, JNJ-18038683, loxapine, lurasidone, LY-215,840, maprotiline, methysergide, mesulergine, mianserin, olanzepine, pimozide, ritanserin, SB-258,719, SB-258,741, SB-269,970, SB-656,104-A, SB-691,673, sertindole, spiperone, tenilapine, TFMPP, vortioxetine, trifluoperazine, ziprasidone, and zotepine |
| Non-selective 5-HT antagonists | | chlorpromazine, cyproheptadine, pizotifen, oxetorone, spiperone, ritanserin, parachlorophenylalanine, metergoline, propranolol, mianserin, carbinoxamine, methdilazine, promethazine, pizotifen, oxatomide, feverfew, fenclonin, and reserpine |

TABLE 6H

GLUATAMATE RECEPTOR AGONISTS AND ANTAGONISTS

| Receptor | Agonist | Antagonist |
|---|---|---|
| Ionotropic (GRIA-14, GRIK1-5, and GRIN1-3B) | AMPA, glutamic acid, ibotenic acid, kainic acid, NMDA, quisqualic acid | AP5, AP7, CPPene, selfotel, HU-211, Huperzine A, gabapentin, remacemide, amantadine, atomoxetine, AZD6765, agmatine, chloroform, dextrallorphan, dextromethorphan, dextrorphan, diphenidine, dizocilpine (MK-801), ethanol, eticyclidine, gacyclidine, ibogaine, ifenprodil, ketamine, kynurenic acid, memantine, magnesium, methoxetamine, nitromemantine, nitrous oxide, PD-137889, perampanel, phencyclidine, rolicyclidine, tenocyclidine, methoxydine, tiletamine, neramexane, eliprodil, etoxadrol, dexoxadrol, WMS-2539, NEFA, delucemine, 8A-PDHQ, aptiganel, rhynchophylline |
| Metabotropic (GRM1-8) | L-AP4, ACPD, L-QA, CHPG, LY-379,268, LY-354,740, ACPT, VU0155041 | AIDA, fenobam, MPEP, LY-367,385, EGLU, CPPG, MAP4, MSOP, LY-341,495 |
| Glycine antagonists | | rapastinel, NRX-1074, 7-chlorokynurenic acid, 4-chlorokynurenine, 5,7-dichlorokynurenic acid, kynurenic acid, TK-40, 1-aminocyclopropanecarboxylic acid (ACPC), L-phenylalanine, and xenon |

TABLE 6I

HISTAMINE AGONISTS AND ANTAGONISTS

| Receptor | Agonist | Antagonist |
|---|---|---|
| Non-selective | histamine dihydrochloride, HTMT dimaleate, 2-pyridylethlyamine dihydrochloride | |
| $H_1$ | | acrivastine, azelastine, astemizole, bilastine, bromodiphenhydramine, brompheniramine, buclizine, carbinoxamine, cetirizine, cetirizine dihydrochloride, clemastine fumarate, clemizole hydrochloride, chlorodiphenhydramine, chlorphenamine, chlorpromazine, clemastine, cyclizine, cyproheptadine, dexbrompheniramine, dexchlorpheniramine, dimenhydrinate, dimethindene maleate, dimethindene, diphenhydramine, diphenhydramine |

TABLE 6I-continued

HISTAMINE AGONISTS AND ANTAGONISTS

| Receptor | Agonist | Antagonist |
|---|---|---|
| | | hydrochloride, doxepin hydrochloride, doxylamine, ebastine, embramine, fexofenadine, fexofenadine hydrochloride, hydroxyzine, ketotifen fumarate, loratadine, meclizine, meclizine dihydrochloride, mepyramine maleate, mirtazapine, olopatadine, olopatadine hydrochloride, orphenadrine, phenindamine, pheniramine, phenyltoloxamine, promethazine, quetiapine, rupatadine, terfenadine, tripelennamine, zotepine, trans-triprolidine hydrochloride, and triprolidine |
| $H_1$ inverse agonists | | cetirizine, levocetirizine, desloratadine, and pyrilamine |
| $H_2$ | betazole, impromidine, dimaprit dihydrochloride, and amthamine dihyrdobromide | aminopotentidine, cimetidine, famotidine, ICI 162,846, lafutidine, nizatidine, ranitidine, ranitidine hyrdochloride, roxatidine, zolantadine dimaleate, and toitidine |
| $H_3$ | imetit dihydropbromide, immepip dihyrdrobromide, immethridine dihyrobromide, a-Methylhistamine dihydrobromide, N-methylhistamine dihydrochloride, proxyfan oxalate, and betahistine | clobenpropit, clobenpropit dihydrobromide, A 3314440 dihyrdochloride, BF 2649 hydrochloride, carcinine ditrifluoroacetate, ABT-239, ciprofaxin, conessine, GT 2016, A-349,821, impentamine dihydrobromide, iodophenpropit dihydrobromide, JNJ 10181457 dihydrochloride, JNJ 5207852 dihydrochloride, ROS 234 dioxalate, SEN 12333, VUF 5681 dihydrobromide, and thioperamide |
| $H_4$ | imetit dihydropbromide, immepip dihyrdrobromide, 4-methylhistamine dihydrochloride, clobenpropit dihydrobromide, VUF 10460, and VUF 8430 dihydrobromide | thioperamide, JNJ 7777120, A 943931 dihydrochloride, A 987306, JNJ 10191584 maleate, and VUF-6002 |

TABLE 6J

CANNABINOID AGONISTS AND ANTAGONISTS

| Receptor | Agonist | Antagonist |
|---|---|---|
| Cannabinoid receptor (non-selective) | Anandamide, N-Arachidonoyl dopamine, 2-Arachidonoylglycerol (2-AG), 2-Arachidonyl glyceryl ether, Δ-9-Tetrahydrocannabinol, EGCG, Yangonin, AM-1221, AM-1235, AM-2232, UR-144, JWH-007, JWH-015, JWH-018_ACEA, ACPA, arvanil, CP 47497, DEA, leelamine, methanandamide, NADA, noladin ether, oleamide, CB 65, GP-1a, GP-2a, GW 405833, HU 308, JWH-133, L-759,633, L-759,656, LEI 101, MDA 19, and SER 601 | |
| $CB_1$ receptor | ACEA, ACPA, RVD-Hpα, (R)-(+)-methanandamide | rimonabant, cannabidiol, Δ$^9$-tetrahydrocannabivarin (THCV), taranabant, otenabant, surinabant, rosonabant, SLV-319, AVE1625, V24343, AM 251, AM 281, AM 6545, hemopressin, LY 320135, MJ 15, CP 945598, NIDA 41020, PF 514273, SLV 319, SR 1141716A, and TC-C 14G |

TABLE 6J-continued

CANNABINOID AGONISTS AND ANTAGONISTS

| Receptor | Agonist | Antagonist |
| --- | --- | --- |
| $CB_2$ receptor | CB 65, GP 1a, GP 2a, GW 405833, HU 308, JWH 133, L-759,656, L-759,633, SER 601, LEI 101 | cannabidiol, $\Delta^9$-tetrahydrocannabivarin (THCV), AM 630, COR 170, JTE 907, and SR 144528 |

TABLE 6K

PURINERGIC RECEPTOR AGONISTS AND ANTAGONISTS

| Receptor | Agonist | Antagonist |
| --- | --- | --- |
| ADORA1 (P1 adenosine receptor) | Adenosine, N6-Cyclopentyladenosine, N6-3-methoxyl-4-hydroxybenzyl adenine riboside (B2), CCPA, tecadenoson, selodenoson, Certain Benzodiazepines and Barbiturates, 2'-MeCCPA, GR 79236, and SDZ WAG 994 | Caffeine, theophylline, 8-Cyclopentyl-1,3-dimethylxanthine (CPX), 8-Cyclopentyl-1,3-dipropylxanthine (DPCPX), 8-Phenyl-1,3-dipropylxanthine, bamifylline, BG-9719, BG09928, FK-453, FK838, rolofylline, N-0861, and PSB 36 |
| ADORA2A (P1 adenosine receptor) | Adenosine, N6-3-methoxyl-4-hydroxybenzyl adenine riboside (B2), YT-146, DPMA, UK-423,097, limonene, NECA, CV-3146, binodenoson, ATL-146e, CGS-21680, and Regadenoson | Caffeine, theophylline, istradefylline, SCH-58261, SCH-442,416, ATL-444, MSX-3, preladenant, SCH-412,348, VER-6623, VER-6947, VER-7835, vipadenant, and ZM-241,385 |
| ADORA2B (P1 adenosine receptor) | Adenosine, 5'-N-ethylcarboxamidoadenosine, BAY 60-6583, LUF-5835, NECA, (S)-PHPNECA, and LUF-5845 | Caffeine, theophylline, CVT-6883, ATL-801, compound 38, MRS-1706, MRS-1754, OSIP-339,391, PSB-603, PSB-0788, and PSB-1115 |
| ADORA3 (P1 adenosine receptor) | Adenosine, 2-(1-Hexynyl)-N-methyladenosine, CF-101 (IB-MECA), CF-102, 2-Cl-IB-MECA, CP-532,903, inosine, LUF-6000, and MRS-3558 | Caffeine, theophylline, MRS-1191, MRS-1220, MRS-1334, MRS-1523, MRS-3777, MRE3008F20, MRE3005F20, OT-7999, SSR161421, KF-26777, PSB-10, PSB-11, and VUF-5574 |
| P2Y receptor | ATP, ADP, UTP, UDP, UDP-glucose, 2-methylthioladenosine 5' diphosphate (2-MeSADP), lysophosphatidic acid, PSB 1114, PSB 0474, NF 546, MRS 2365, MRS 2690, MRS 2693, MRS 2768, MRS 2905, MRS 2957, MRS 4062, and denufosol ($P2Y_2$ agonist) | clopidogrel, elinogrel, prasugrel, ticlopidine, ticagrelor, AR-C 118925XX, AR-C 66096, AR-C 69931, AZD 1283, MRS 2179, MRS 2211, MRS 2279, MRS 2500, MRS 2578, NF 157, NF 340, PPADS, PPTN hydrochloride, PSD 0739, SAR 216471, and suramin |
| P2X receptor | ATP | A 438079, A 740003, A 804598, A 839977, AZ 10606120, AZ 11645373, 5-BDBD, BX 430, Evans Blue, JNJ 47965567, KN-62, NF 023, NF 110, NF 157, NF 279, NF 449, PPADS, iso-PPADS, PPNDS, Ro 0437626, Ro 51, RO-3, TC-P 262, suramin, TNP-ATP, and P2X7 antagonists NF279, calmidazolium, and KN-62 |

TABLE 7

NEUROTRANSMISSION MODULATORS

| Type | Modulators |
|---|---|
| Norepinephrine reuptake inhibitors (increase adrenergic neurotransmission) | amedalin, atomoxetine, CP-39,332, daledalin, edivoxetine, esreboxetine, lortalamine, nisoxetine, reboxetine, talopram, talsupram, tandamine, viloxazine, bupropion, ciclazindol, manifaxine, maprotiline, radafaxine, tapentadol, teniloxazine, protriptyline, nortriptyline, and desipramine |
| Norepineprhine-dopamine reuptake inhibitors (increase adrenergic and dopamine neurotransmission) | amineptine, bupropion, desoxypipradrol, dexmethylphenidate, difemetorex, diphenylprolinol, ethylphenidate, fencamfamine, fencamine, lefetamine, methylenedioxypyrovalerone, methylphenidate, nomifensine, O-2172, oxolinic acid, pipradrol, prolintane, pyrovalerone, tametraline, and WY-46824 |
| Serotonin-norepinephrine-dopamine reuptake inhibitors (SNDRIs) and serotonin-norepinephrine reuptake inhibitors (SNRIs) (increase adrengergic, dopamine, and serotonin neurotransmission) | mazindol, nefazodone, sibutramine, venlafaxine, esketamine, duloxetine, ketamine, phencyclidine, tripelennamine, mepiprazole, amitifadine, AN788, ansofaxine, centanafadine, atomoxetine, desvenlafaxine, milnacipran, levomilnacipran, dasotraline, Lu AA34893, Lu AA37096, NS-2360, tedatioxetine, tesofensine, bicifadine, BMS-866,949, brasofensine, diclofensine, DOV-216,303, EXP-561, liafensine, NS-2359, RG-7166, SEP-227,162, SEP-228,425, SEP-228,432, naphyrone, 3,3-Diphenylcyclobutanamine, 3,4-Dichlorotametraline, D-161, desmethylsertraline, DMNPC, DOV-102,677, fezolamine, GSK1360707F, indatraline, JNJ-7925476, JZ-IV-10, JZAD-IV-22, LR-5182, methylnaphthidate, MI-4, PRC200-SS, PRC050, PR0025, SKF-83,959, TP1, phenyltropanes (e.g., WF-23, dichloropane, and RTI-55), *Ginkgo biloba* extract, St John's Wort, hyperforin, adhyperforin, and uliginosin B |
| Dopamine reuptake inhibitors (increase dopamine neurotransmission) | Dopamine reuptake inhbiitors (e.g., altropane, amfonelic acid, amineptine, BTCP, 3C-PEP, DBL-583, difluoropine, GBR-12783, GBR-12935, GBR-13069, GBR-13098, GYKI-52895, lometopane, methylphenidate, ethylphenidate, modafinil, armodafinil, RTI-229, vanoxerine, adrafinil, benztropine, bupropion, fluorenol, medifoxamine, metaphit, rimcazole, venlafaxine, *Chaenomeles speciosa*, and oroxylin A), dopamine releasing agents (e.g., p-Tyramine), dextroamphetamine, lisdexamfetamine, dexmethylphenidate, and cathinone |
| Dopamine prodrugs (increase dopamine neurotransmission) | Levopoda, docarpamine |
| GABA reuptake inhibitors (increase GABA neurotransmission) | CL-996, deramciclane, gabaculine, guvacine, nipecotic acid, NNC-711, NNC 05-2090, SKF-89976A, SNAP-5114, tiagabine, and hyperforin |
| GABA analogs (increase GABA neurotransmission) | gabapentin, butyric acid, valproic acid, valpromide, valnoctamide, 3-hydroxybutanal, GHB, sodium, oxybate, aceburic acid, GBL, GHBAL, GHV, GVL, GHC, GCL, HOCPCA, UMB68, pregabalin, tolibut, phaclofen, sacolfen, arecaidine, gaboxadol, isonipecotic acid, 3-Methyl-GABA, AABA, BABA, DAVA, GAVA, Glutamic acid, hopantenic acid, piracetam, and vigabatrin |
| GABA prodrugs (increase GABA neurotransmission) | L-Glutamine, N-Isonicotinoyl-GABA, picamilon, progabide, tolgabide |
| Acetylcholinesterase inhibitors (increase nicotinic and muscarinic neurotransmission) | carbamates, physostigmine, neostigmine, pyridostigmine, ambenonium, demecarium, rivastigmine, phenanthrene derivatives, galantamine, caffeine, rosmarinic acid, alpha-pinene, piperidines, donepezil, tacrine, edrophonium, Huperzine A, ladostigil, ungeremine, lactucopicrin, dyflos, echothiophate, parathion, and quasi-irreversible acetylcholinesterase inhibitors |
| Serotonin reuptake inhibitors (increase serotonin neurotransmission) | alaproclate, cericlamine, citalopram, dapoxetine, escitalopram, femoxetine, fluoxetine, fluvoxamine, ifoxetine, indalpine, omiloxetine, panuramine, paroxetine, pirandamine, RTI-353, sertraline, zimelidine, desmethylcitalopram, didesmethylcitalopram, seproxetine ((S)-norfluoxetine), desvenlafaxine, cianopramine, litoxetine, lubazodone, SB-649,915, trazodone, vilazodone, vortioxetine, dextromethorphan, |

TABLE 7-continued

| Type | Modulators |
|---|---|
| Serotonin releasing agents (increase serotonin neurotransmission) | dextropropoxyphene, dimenhydrinate, diphenhydramine, mepyramine (pyrilamine), mifepristone, delucemine, mesembrenone, mesembrine, roxindole, duloxetine, levomilnacipran, milnacipran, dapoxetine, sibutramine, chlorpheniramine, dextropmethorphan, and methadone chlorphentermine, cloforex, dexfenfluramine, etolorex, fenfluramine, flucetorex, indeloxazine, levofenfluramine, tramadol, carbamazepine, amiflamine (FLA-336), viqualine (PK-5078), 2-Methyl-3,4-methylenedioxyamphetamine (2-Methyl-MDA), 3-Methoxy-4-methylamphetamine (MMA), 3-Methyl-4,5-methylenedioxyamphetamine (5-Methyl-MDA), 3,4-Ethylenedioxy-N-methylamphetamine (EDMA), 4-Methoxyamphetamine (PMA), 4-Methoxy-N-ethylamphetamine (PMEA), 4-Methoxy-N-methylamphetamine (PMMA), 4-Methylthioamphetamine (4-MTA), 5-(2-Aminopropyl)-2,3-dihydrobenzofuran (5-APDB), 5-Indanyl-2-aminopropane (IAP), 5-Methoxy-6-methylaminoindane (MMAI), 5-Trifluoromethyl-2-aminoindane (TAI), 5,6-Methylenedioxy-2-aminoindane (MDAI), 5,6-Methylenedioxy-N-methyl-2-aminoindane (MDMAI), 6-Chloro-2-aminotetralin (6-CAT), 6-Tetralinyl-2-aminopropane (TAP), 6,7-Methylenedioxy-2-aminotetralin (MDAT), 6,7-Methylenedioxy-N-methyl-2-aminotetralin (MDMAT), N-Ethyl-5-trifluoromethyl-2-aminoindane (ETAI), N-Methyl-5-indanyl-2-aminopropane, aminorex, MDMA, MDEA, MDA, MBDB, and tryptamines, such as DMT, αMT, 5MeO-NMT, NMT, NETP, Dimethyl-Serotonin, 5MeO-NET, αET and αMT |
| Excitatory amino acid reuptake inhibitors (increase Glutamate receptor neurotransmission) | didydrokanic acid, WAY-213,613, L-trans-2,4-PDC, amphetamine, and L-Theanine |
| Glycine reuptake inhibitors (increase Glutamate receptor neurotransmission) | bitopertin, Org 24598, Org 25935, ALX-5407, sacrosine, Org 25543, and N-arachidonylglycerine |
| Histidine decarboxylase inhibitors (decrease histamine neurotransmission) | Tritoqualine, catechin |
| Endocannabinoid enhancers (increase cannabinoid neurotransmission) | AM404, fatty acid amide hydrolase inhibitors (e.g., AM374, ARN2508, BIA 10-2472, BMS-469908, CAY-10402, JNJ-245, JNJ-1661010, JNJ-28833155, JNJ-40413269, JNJ-42119779, JNJ-42165279, MK-3168, MK-4409, MM-433593, OL-92, OL-135, PF-622, PF-750, PF-3845, PF-04457845, PF-04862853, RN-450, SA-47, SA-73, SSR-411298, ST-4068, TK-25, URB524, URB597, URB694, URB937, VER-156084, and V-158866 |
| Monoacylglycerol lipase inhibitors (increase cannabinoid neurotransmission) | N-arachidonoyl maleimide, JZL184 |
| Endocannabinoid transporter inhibitors (increase cannabinoid neurotransmission) | SB-FI-26 |
| Endocannabinoid reuptake inhibitors (increase cannabinoid neurotransmission) | AM404, AM1172, LY-2183240, O-2093, OMDM-2, UCM-707, VDM-11, guineensine, ETI-T-24_B_I, WOBE437, and RX-055 |
| Adenosine uptake inhibitors (increase purinergic neurotransmission) | cilostazol, dilazep, and dipyramidole |
| Nucleoside transporter inhibitors (increase purinergic neurotransmission) | 8MDP, Decynium 22, 5-iodotubercidin, NBMPR, and TC-T 6000 |

In some embodiments, the neurotransmission modulator is a neurotoxin listed in Table 8, or a functional fragment or variant thereof. Neurotoxins include, without limitation, convulsants, nerve agents, parasympathomimetics, and uranyl compounds. Neurotoxins may be bacterial in origin, or fungal in origin, or plant in origin, or derived from a venom or other natural product. Neurotoxins may be synthetic or engineered molecules, derived de novo or from a natural product. Suitable neurotoxins include but are not limited to botulinum toxin and conotoxin. Exemplary neurotoxins are listed in Table 8.

TABLE 8

NEUROTOXINS 2,4,5-Trihydroxyamphetamine
2,4,5-Trihydroxymethamphetamine
3,4-Dichloroamphetamine
5,7-Dihydroxytryptamine
5-Iodowillardiine
Ablomin
Aconitine
Aconitum

TABLE 8-continued

NEUROTOXINS

Aconitum anthora
AETX
Agelenin
Agitoxin
Aldrin
Alpha-Methyldopamine
Alpha-neurotoxin
Altitoxin
Anatoxin-a
Androctonus australis hector insect toxin
Anisatin
Anthopleurin
Antillatoxin
Anuroctoxin
Apamin
Arum italicum
Arum maculatum
Babycurus toxin 1
Batrachotoxin
BDS-1
Bestoxin
Beta-Methylamino-L-alanine
BgK
Birtoxin
BmKAEP
BmTx3
BotIT2
BotIT6
Botulinum toxin
Brevetoxin
Bukatoxin
Butantoxin
Calcicludine
Calciseptine
Calitoxin
Caramboxin
Carbon disulfide
CgNa toxin
Charybdotoxin
Cicutoxin
Ciguatoxin
CII1
Clostridium botulinum
Conantokins
Conhydrine
Coniine
Conotoxin
Contryphan
CssII
CSTX
Curare
Cyanide poisoning
Cylindrospermopsin
Cypermethrin
Delta atracotoxin
Dendrotoxin
Dieldrin
Diisopropyl fluorophosphates
Dimethylmercury
Discrepin
Domoic acid
Dortoxin
DSP-4
Ergtoxin
Falcarinol
Fenpropathrin
Gabaculine
Ginkgotoxin
Grammotoxin
Grayanotoxin
Hainantoxin
Halcurin
Hefutoxin
Helothermine
Heteroscodratoxin-1
Histrionicotoxin
Homoquinolinic acid
Hongotoxin

TABLE 8-continued

NEUROTOXINS

Huwentoxin
Ibotenic acid
Ikitoxin
inhibitor cystine knot
Jingzhaotoxin
Kainic acid
Kaliseptine
Kappa-bungarotoxin
Kodaikanal mercury poisoning
Kurtoxin
Latrotoxin
Lq2
Maitotoxin
Margatoxin
Maurotoxin
Mercury (element)
Methanol
Meth iocarb
MPP+
MPTP
Nemertelline
Neosaxitoxin
Nicotine
N-Methylconiine
Oenanthotoxin
Oxalyldiaminopropionic acid
Oxidopamine
Oxotoxin
Pahutoxin
Palytoxin
Pandinotoxin
Para-Bromoamphetamine
Para-Chloroamphetamine
Para-Chloromethamphetamine
Para-Iodoamphetamine
Penitrem A
Phaiodotoxin
Phenol
Phoneutria nigriventer toxin-3
Phrixotoxin
Polyacrylamide
Poneratoxin
Psalmotoxin
Pumiliotoxin
Quinolinic acid
Raventoxin
Resiniferatoxin
Samandarin
Saxitoxin
Scyllatoxin
Sea anemone neurotoxin
Slotoxin
SNX-482
Stichodactyla toxin
Taicatoxin
Taipoxin
Tamapin
Tertiapin
Tetanospasmin
Tetraethylammonium
Tetramethylenedisulfotetramine
Tetrodotoxin
Tityustoxin
Tricresyl phosphate
TsIV
Vanillotoxin
Veratridine

Antibodies

Neurotransmission modulators also include antibodies that bind to neurotransmitters or neurotransmitter receptors listed in Tables 4 and 5 and decrease neurotransmission. These antibodies include blocking and neutralizing antibodies. Antibodies to neurotransmitters or neurotransmitter receptors listed in Tables 4 and 5 can be generated by those of skill in the art using well established and routine methods.

Neuronal Growth Factor Modulator

In some embodiments, the calcitonin receptor inhibitor is administered with a neuronal growth factor modulator (e.g., an agent that decreases or increases neurogenic/axonogenic signals, e.g., a neuronal growth factor or neuronal growth factor mimic, or an agonist or antagonist of a neuronal growth factor or neuronal growth factor receptor). For example, the neuronal growth factor modulator is a neuronal growth factor listed in Table 9, e.g., a neuronal growth factor having the sequence referenced by accession number or Entrez Gene ID in Table 9, or an analog thereof, e.g., a sequence having at least 75%, 80%, 85%, 90%, 90%, 98%, 99% identity to the sequence referenced by accession number or Entrez Gene ID in Table 9. Neuronal growth factor modulators also include agonists and antagonists of neuronal growth factors and neuronal growth factor receptors listed in Table 9. A neuronal growth factor modulator may increase or decrease neurogenesis, neuronal growth, neuronal differentiation, neurite outgrowth, synapse formation, synaptic maturation, synaptic refinement, or synaptic stabilization. Neuronal growth factor modulators regulate tissue innervation (e.g., innervation of a lymph node or site of inflammation) and the formation of synaptic connections between two or more neurons and between neurons and non-neural cells (e.g., between neurons and immune cells). A neuronal growth factor modulator may block one or more of these processes (e.g., through the use of antibodies that block neuronal growth factors or their receptors) or promote one or more of these processes (e.g., through the use of neuronal growth factors or analogs thereof). Neuronal growth factor modulators can increase or decrease one of the abovementioned processes by 10%, 20%, 30%, 40%, 50%, 60%, 70%, 80%, 90%, 95%, 98%, 200%, 500% or more.

In some embodiments, the neuronal growth factor modulator is one that increases neurogenic/axonogenic signals, e.g., the method includes administering to the subject or contacting a cell with a neuronal growth factor modulator in an amount and for a time sufficient to increase neurogenesis or axonogenesis. For example, the neuronal growth factor modulator that leads to an increase in neurogenesis or axonogenesis is a neurotrophic factor. Relevant neurotrophic factors include NGF, BDNF, ProNGF, Sortilin, TGFβ and TGFβ family ligands and receptors (e.g., TGFβR1, TGFβR2, TGFβ1, TGFβ2 TGFβ4), GFRα family ligands and receptors (e.g., GFRα1, GFRα2, GFRα3, GFRα4, GDNF), CNTF, LIF, neurturin, artemin, persephin, neurotrophin, chemokines, cytokines, and others listed in Table 9. Receptors for these factors may also be targeted, as well as downstream signaling pathways including Jak-Stat inducers, and cell cycle and MAPK signaling pathways. In some embodiments, the neuronal growth factor modulator increases neurogenesis, axonogenesis or any of the processes mentioned above by administering, locally delivering, or stabilizing a neuronal growth factor listed in Table 9, or by upregulating, agonizing, or stabilizing a neuronal growth factor receptor listed in Table 9. In some embodiments, the neuronal growth factor modulator increases neurogenesis, axonogenesis or any of the processes mentioned above by stabilizing, agonizing, overexpressing, or upregulating a signaling protein encoded by a gene that is downstream of a neuronal growth factor. In some embodiments, the neuronal growth factor modulator increases neurogenesis, axonogenesis or any of the processes mentioned above by stabilizing, overexpressing, or upregulating a synaptic or structural protein. Neurogenesis, axonogenesis, neuronal growth, neuronal differentiation, neurite outgrowth, synapse formation, synaptic maturation, synaptic refinement, or synaptic stabilization can be increased in the subject at least 1%, 2%, 5%, 10%, 15%, 20%, 25%, 30%, 35%, 40%, 50%, 60%, 70%, 80% or more, compared to before the administration. Neurogenesis, axonogenesis, neuronal growth, neuronal differentiation, neurite outgrowth, synapse formation, synaptic maturation, synaptic refinement, or synaptic stabilization can be increased in the subject between 5-20%, between 5-50%, between 10-50%, between 20-80%, between 20-70%.

In some embodiments, the neuronal growth factor modulator decreases neurogenic/axonogenic signals, e.g., the method includes administering to the subject or contacting a cell with a neuronal growth factor modulator in an amount and for a time sufficient to decrease neurogenesis, axonogenesis, or innervation. For example, the neuronal growth factor modulator that leads to a decrease in neurogenesis or axonogenesis is a blocking or neutralizing antibody against a neurotrophic factor. Relevant neurotrophic factors include NGF, BDNF, ProNGF, Sortilin, TGFβ and TGFβ family ligands and receptors (e.g., TGFβR1, TGFβR2, TGFβ1, TGFβ2 TGFβ4), GFRα family ligands and receptors (e.g., GFRα1, GFRα2, GFRα3, GFRα4, GDNF), CNTF, LIF, neurturin, artemin, persephin, neurotrophin, chemokines, cytokines, and others listed in Table 9. Receptors for these factors can also be targeted, as well as downstream signaling pathways including Jak-Stat inducers, and cell cycle and MAPK signaling pathways. In some embodiments, the neuronal growth factor modulator decreases neurogenesis, axonogenesis or any of the processes mentioned above by sequestering, blocking, antagonizing, degrading, or downregulating a neuronal growth factor or a neuronal growth factor receptor listed in Table 9. In some embodiments, the neuronal growth factor modulator decreases neurogenesis, axonogenesis or any of the processes mentioned above by blocking or antagonizing a signaling protein that is downstream of a neuronal growth factor. In some embodiments, the neuronal growth factor modulator decreases neurogenesis, axonogenesis or any of the processes mentioned above by blocking, disrupting, or antagonizing a synaptic or structural protein. Neurogenesis, axonogenesis, neuronal growth, neuronal differentiation, neurite outgrowth, synapse formation, synaptic maturation, synaptic refinement, synaptic stabilization, or tissue innervation can be decreased in the subject at least 1%, 2%, 5%, 10%, 15%, 20%, 25%, 30%, 35%, 40%, 50%, 60%, 70%, 80% or more, compared to before the administration. Neurogenesis, axonogenesis, neuronal growth, neuronal differentiation, neurite outgrowth, synapse formation, synaptic maturation, synaptic refinement, synaptic stabilization, or tissue innervation can be decreased in the subject between 5-20%, between 5-50%, between 10-50%, between 20-80%, between 20-70%. Neuronal growth factor blockers can be administered in any of the modalities described herein (e.g., antibody, small molecule, nucleic acid, polypeptide, or viral vector).

In some embodiments, the neuronal growth factor modulator decreases the number of nerves in an affected tissue (e.g., a lymph node or site of inflammation). For example, the neuronal growth factor blocker is administered in an amount and for a time sufficient to decrease neurogenesis/axonogenesis.

Neuronal growth factor blockers include antibodies that bind to neuronal growth factors or neuronal growth factor receptors and decrease their signaling (e.g., blocking antibodies). Exemplary neuronal growth factor blocking antibodies are listed below in Table 10. Antibodies to neuronal growth factors listed in Table 9 can also be generated by those of skill in the art using well established and routine methods.

TABLE 9

NEURONAL GROWTH FACTORS

| Gene | Type | Accession Number | Entrez Gene ID |
|---|---|---|---|
| ARTN | Ligand | Q5T4W7 | 9048 |
| BDNF | Ligand | P23560 | 627 |
| BDNF-AS | Ligand |  | 497258 |
| BEX1 | Signaling | Q9HBH7 | 55859 |
| BEX3 | Signaling | Q00994 | 27018 |
| CD34 | Receptor | P28906 | 947 |
| CDNF | Ligand | Q49AH0 | 441549 |
| CNTF | Ligand | P26441 | 1270 |
| CNTFR | Receptor | P26992 | 1271 |
| CRLF1 | Receptor | O75462 | 9244 |
| CSPG5 | Ligand | O95196 | 10675 |
| DCLK1 | Signaling | O15075 | 9201 |
| DISC1 | Signaling | Q9NRI5 | 27185 |
| DNAJC5 | Signaling | Q9H3Z4 | 80331 |
| DPYSL2 | Signaling | Q16555 | 1808 |
| DVL1 | Signaling | O14640 | 1855 |
| EFNA5 | Ligand | P52803 | 1946 |
| EGR3 | Signaling | Q06889 | 1960 |
| ENO2 | Signaling | P09104 | 2026 |
| EphA1 | Receptor | P21709 | 2041 |
| EphA10 | Receptor | Q5JZY3 | 284656 |
| EphA2 | Receptor | P29317 | 1969 |
| EphA3 | Receptor | P29320 | 2042 |
| EphA4 | Receptor | P29317 | 2043 |
| EphA5 | Receptor | P54756 | 2044 |
| EphA6 | Receptor | Q9UF33 | 285220 |
| EphA7 | Receptor | Q15375 | 2045 |
| EphA8 | Receptor | P29322 | 2046 |
| EphB1 | Receptor | P54762 | 2047 |
| EphB2 | Receptor | P29323 | 2048 |
| EphB3 | Receptor | P54753 | 2049 |
| EphB4 | Receptor | P54760 | 2050 |
| EphB6 | Receptor | O15197 | 2051 |
| ETBR2 | Receptor | O60883 | 9283 |
| FSTL4 | Receptor | Q6MZW2 | 23105 |
| GDNF | Ligand | P39905 | 2668 |
| GFRA1 | Receptor | P56159 | 2674 |
| GFRA2 | Receptor | O00451 | 2675 |
| GFRA3 | Receptor | O60609 | 2676 |
| GFRA4 | Receptor | Q9GZZ7 | 64096 |
| GPR37 | Receptor | O15354 | 2861 |
| GPRIN1 | Signaling | Q7Z2K8 | 114787 |
| GPRIN2 | Signaling | O60269 | 9721 |
| GPRIN3 | Signaling | Q6ZVF9 | 285513 |
| GRB2 | Signaling | P62993 | 2885 |
| GZF1 | Signaling | Q9H116 | 64412 |
| IFNA1 | Ligand | P01562 | 3439 |
| IGF1 | Ligand | P05019 | 3479 |
| IGF2 | Ligand | P01344 | 3481 |
| IL11RA | Receptor | Q14626 | 3590 |
| IL1B | Ligand | P01584 | 3553 |
| IL3 | Ligand | P08700 | 3562 |
| IL4 | Ligand | P05112 | 3565 |
| IL6 | Ligand | P05231 | 3569 |

TABLE 9-continued

NEURONAL GROWTH FACTORS

| Gene | Type | Accession Number | Entrez Gene ID |
|---|---|---|---|
| IL6R | Receptor | P08887 | 3570 |
| IL6ST | Signaling | P40189 | 3572 |
| INS | Ligand | P01308 | 3630 |
| L1CAM | Signaling | P32004 | 3897 |
| LIF | Ligand | P15018 | 3976 |
| LIFR | Receptor | P42702 | 3977 |
| MAGED1 | Signaling | Q9Y5V3 | 9500 |
| MANF | Ligand | P55145 | 7873 |
| NDNF | Ligand | Q8TB73 | 79625 |
| NENF | Ligand | Q9UMX5 | 29937 |
| NENFP1 | Ligand |  | 106480294 |
| NENFP2 | Ligand |  | 100129880 |
| NENFP3 | Ligand |  | 106481703 |
| NGF | Ligand | P01138 | 4803 |
| NGFR | Receptor | P08138 | 4804 |
| NRG1 | Ligand | Q02297 | 3084 |
| NRP1 | Receptor | O14786 | 8829 |
| NRTN | Ligand | Q99748 | 902 |
| NTF3 | Ligand | P20783 | 4908 |
| NTF4 | Ligand | P34130 | 4909 |
| NTRK1 | Receptor | P04629 | 4914 |
| NTRK2 | Receptor | Q16620 | 4915 |
| NTRK3 | Receptor | Q16288 | 4916 |
| PDPK1 | Signaling | O15530 | 5170 |
| PEDF | Ligand | P36955 | 5176 |
| PLEKHH3 | Signaling | Q7Z736 | 79990 |
| PSAP | Ligand | P07602 | 5660 |
| PSEN1 | Signaling | P49768 | 5663 |
| PSPN | Ligand | O70300 | 5623 |
| PTN | Ligand | P21246 | 5764 |
| RELN | Ligand | P78509 | 5649 |
| RET | Signaling | P07949 | 5979 |
| ROR1 | Receptor | Q01973 | 4919 |
| ROR2 | Receptor | Q01974 | 4920 |
| RPS6KA3 | Signaling | P51812 | 6197 |
| SDC3 | Receptor | O75056 | 9672 |
| SEMA3E | Ligand | O15041 | 9723 |
| SERPINE2 | Ligand | P07093 | 5270 |
| SERPINF1 | Ligand | P36955 | 5176 |
| SHC1 | Signaling | P51812 | 6464 |
| SNTG1 | Biosynthesis | P07602 | 54212 |
| SORCS1 | Receptor | O75056 | 114815 |
| SORCS2 | Receptor | O15041 | 57537 |
| SORCS3 | Receptor | P07093 | 22986 |
| SORT1 | Receptor | Q99523 | 6272 |
| SULF1 | Signaling | Q8IWU6 | 23213 |
| SULF2 | Signaling | Q8IWU5 | 55959 |
| TGFB1 | Ligand | P01137 | 7040 |
| TGFB2 | Ligand | P61812 | 7042 |
| TGFB3 | Ligand | P10600 | 7043 |
| TMEM158 | Receptor | Q8WZ71 | 25907 |
| TNF | Ligand | P01375 | 7124 |
| TPM3 | Receptor | P06753 | 7170 |
| VEGFA | Ligand | P15692 | 7422 |
| VEGFB | Ligand | P49765 | 7423 |
| VGF | Ligand | O15240 | 7425 |
| XCR1 | Receptor | P46094 | 2829 |
| ZN274 | Signaling | Q96G06 | 10782 |

TABLE 10

NEURONAL GROWTH FACTOR ANTIBODIES

| Neuronal Growth Factor | Antibody | Company |
|---|---|---|
| BDNF | 3868 (agonist antibody) | Pfizer |
| BDNF | 29D7 (agonist antibody) | Pfizer |
| EphA3 | KB004 | KaloBios Pharmaceuticals, Inc. |
| IFNA1 | Faralimomab | Creative Biolabs |
| IFNA1 | Sifalimumab (MEDI-545) | MedImmune |
| IFNA1 | Rontalizumab | Genentech |

TABLE 10-continued

NEURONAL GROWTH FACTOR ANTIBODIES

| Neuronal Growth Factor | Antibody | Company |
|---|---|---|
| IGF | Figitumumab (CP-751,871)-an IGR-1R MAb | Pfizer |
| IGF | SCH717454 (Robatumamab, inhibits IGF initiated phosphorylation) | Merck |
| IGF | Cixutumumab (IGF-1R antibody) | Eli Lilly |
| IGF | Teprotumumab (IGF-1R blocking antibody) | Genmab/Roche |
| IGF-2 | Dusigitumab | MedImmune/AstraZeneca |
| IGF-2 | DX-2647 | Dyax/Shire |
| IGF | Xentuzumab | Boehringer Ingelheim/Eli Lilly |
| IGF | Dalotuzumab (IGFR1 blocking antibody) | Merck & Co. |
| IGF | Figitumumab (IGFR1 blocking antibody) | Pfizer |
| IGF | Ganitumab (IGFR1 blocking antibody) | Amgen |
| IGF | Robatumumab (IGFR1 blocking antibody) | Roche/Schering-Plough |
| IL1B | Canakinumab | Novartis |
| IL1B | APX002 | Apexigen |
| IL1B | Gevokizumab | XOMA |
| IL4 | Pascolizumab | GlaxoSmithKline |
| IL4 | Dupilumab | Regeneraon/Sanofi |
| IL6 | Siltuximab | Janssen Biotech, Inc. |
| IL6 | Olokizumab | UCB/R-Pharm |
| IL6 | Elsilimomab | Orphan Pharma International |
| IL6 | Sirukumab | Centocor |
| IL6 | Clazakizumab | Bristol Myers Squib/Alder Biopharmaceuticals |
| IL6 | Gerilimzumab (ARGX-109) | arGEN-X/RuiYi |
| IL6 | FE301 | Ferring Pharmaceuticals |
| IL6 | FM101 | Femta Pharmaceuticals |
| IL-6R | Sarilumab (directed against IL6R) | Regeneron/Sanofi |
| IL-6R | Tocilizumab | Hoffmann-La Roche/Chugai |
| IL-6R | Sapelizumab | Chugai |
| IL-6R | Vobarilizumab | Ablynx |
| L1CAM | AB417 | Creative biolabs |
| L1CAM | L1-9.3 | Creative biolabs |
| L1CAM | L1-14.10 | Biolegend |
| NGF | Tanezumab | Pfizer |
| NGF | Fulranumab (JNJ-42160443), | Amgen |
| NGF | MNAC13 (anti-TrkA, the NGF receptor) | Creative Biolabs |
| NGF | mAb 911 | Rinat/Pfizer |
| NGF | Fasinumab | Regeneron/Teva |
| NRG1 | 538.24 | Hoffman-La Roche |
| NRP1 | Vesencumab | Genentech/Roche |
| ROR1 | Cirmtuzumab | Oncternal Therapeutics |
| SAP | GSK2398852 | GlaxoSmithKline |
| TGFβ | Fresolimumab (pan-TGFβ antibody) | Genzyme/Aventis |
| TGFβ | IMC-TR1 (LY3022859) (MAb against TGFβRII) | Eli Lilly |
| TGFβ | TβM1 (anti-TGFβ1 MAb) | Eli Lilly |
| TGFβ2 | Lerdelimumab (CAT-152) | Genzyme |
| TGFβ1 | Metelimumab | Genzyme |
| TGFβ1 | LY2382770 | Eli Lilly |
| TGFβ | PF-03446962 (MAb against TGFβRI) | Pfizer |
| TNF | Infliximab | Janssen Biotech, Inc. |
| TNF | Adalimumab | AbbVie Inc. |
| TNF | Certolizumab pegol | UCB |
| TNF | Golimumab | Janssen Biotech, Inc. |
| TNF | Afelimomab | |
| TNF | Placulumab | Teva Pharmaceutical Industries, Inc. |
| TNF | Nerelimomab | Chiron/Celltech |
| TNF | Ozoralizumab | Pfizer/Ablynx |
| VEGFA | Bevacizumab | Genentech |
| VEGFA | Ranibizumab | Genentech |
| VEGF | Alacizumab pegol (anti-VEGFR2) | UCB |
| VEGFA | Brolucizumab | Novartis |
| VEGF | Icrucumab (anti-VEGFR1) | Eli Lilly |
| VEGF | Ramucirumab (anti-VEGFR2) | Eli Lilly |

Neuronal growth factor modulators also include agents that agonize or antagonize neuronal growth factors and neuronal growth factor receptors. For example, neuronal growth factor modulators include TNF inhibitors (e.g., etanercept, thalidomide, lenalidomide, pomalidomide, pentoxifylline, bupropion, and DOI), TGFβ1 inhibitors, (e.g., disitertide (P144)), TGFβ2 inhibitors (e.g., trabedersen (AP12009)). Exemplary neuronal growth factor agonists and antagonists are listed in Table 11.

TABLE 11

NEURONAL GROWTH FACTOR AGONISTS AND ANTAGONISTS

|  | Agonist | Antagonist |
|---|---|---|
| TrkA | NGF, amitriptyline, and gambogic amide, gambogic acid | ALE-0540 |
| TrkB | BDNF, NT3, NT4, 3,7-Dihydroxyflavone, 3,7,8,2'-Tetrahydroxyflavone, 4'-Dimethylamino-7,8-dihydroxyflavone, 7,3'-Dihydroxyflavone, 7,8-Dihydroxyflavone, 7,8,2'-Trihydroxyflavone, 7,8,3'-Trihydroxyflavone, Amitriptyline, Deoxygedunin, Diosmetin, HIOC, LM22A-4, N-Acetylserotonin, Norwogonin (5,7,8-THF), R7, LM22A4, and TDP6 | ANA-12, cyclotraxin B, and gossypetin |
| Pan-Trk receptor |  | entrectinib (RXDX-101), AG 879, GNF 5837, GW 441756, and PF 06273340 |
| GFRα1R | GDNF and XIB4035 |  |
| VEGF receptor |  | AEE 788, AG 879, AP 24534, axitinib, DMH4, GSK 1363089, Ki 8751, RAF 265, SU 4312, SU 5402, SU 5416, SU 6668, sunitinib, toceranib, vatalanib, XL 184, ZM 306416, and ZM 323881 |
| TGFβRI |  | galunisertib (LY2157299), TEW-7197, SB-431542, A 83-01, D 4476, GW 788388, LY 364947, R 268712, RepSox, SB 505124, SB 525334, and SD 208 |

In any of the combination therapy approaches described herein, the first and second therapeutic agent (e.g., a calcitonin receptor activator described herein and the additional therapeutic agent) are administered simultaneously or sequentially, in either order. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

Diagnosis and Prognosis of Calcitonin Receptor-Associated Inflammatory or Autoimmune Diseases or Conditions The methods described herein include methods of diagnosing or identifying patients with a calcitonin receptor-associated inflammatory or autoimmune disease or condition. Subjects who can be diagnosed or identified as having a calcitonin receptor-associated inflammatory or autoimmune disease or condition are subjects who have an inflammatory or autoimmune disease or condition (e.g., subjects identified as having an inflammatory or autoimmune disease or condition), or subjects suspected of having an inflammatory or autoimmune disease or condition. Subjects can be diagnosed or identified as having a calcitonin receptor-associated inflammatory or autoimmune disease or condition based on screening of patient samples (e.g., immune cells collected from a subject, e.g., macrophages). Calcitonin receptor expression (e.g., expression of CALCR and/or RAMP1) can be assessed in a sample of immune cells isolated from a subject using standard techniques known in the art, such as immunohistochemistry, western blot analysis, quantitative RT-PCR, RNA sequencing, fluorescent in situ hybridization, cDNA microarray, and droplet digital PCR. Calcitonin receptor expression (e.g., expression of CALCR and/or RAMP1) can be assessed by comparing measurements obtained from immune cells collected from a subject having or suspected of having an inflammatory or autoimmune disease or condition to measurements of calcitonin receptor expression obtained from a reference sample (e.g., immune cells of the same type collected from a subject that does not have an inflammatory or autoimmune disease or condition or a cell that does not express calcitonin receptors, e.g., a HEK cell). Reference samples can be obtained from healthy subjects (e.g., subjects without an inflammatory or autoimmune disease or condition), or they can be obtained from databases in which average measurements of calcitonin receptor expression (e.g., expression of CALCR and/or RAMP1) are cataloged for immune cells from healthy subjects (e.g., subjects without an inflammatory or autoimmune disease or condition).

Subjects are diagnosed or identified as having a calcitonin receptor-associated inflammatory or autoimmune disease or condition if calcitonin receptor expression (e.g., expression of CALCR and/or RAMP1) is decreased in the sample of immune cells from the subject compared to the reference sample. A decrease of calcitonin receptor expression of 1.1-fold or more (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) in the inflammatory or autoimmune disease or condition sample compared to the reference indicates that the subject has a calcitonin receptor-associated inflammatory or autoimmune disease or condition. Subjects can also be diagnosed or identified as having a calcitonin receptor-associated inflammatory or autoimmune disease or condition (e.g., an inflammatory or autoimmune disease or condition in which a calcitonin receptor is functional in immune cells) by contacting (e.g., incubating) an immune cell (e.g., a macrophage) isolated from the subject with a calcitonin receptor activator (e.g., agonist) and evaluating immune cell cytokine production. A decrease in pro-inflammatory cytokine production (e.g., IFNγ or IL6 release) by 10% or more (e.g., 10%, 15%, 20%, 25%, 30%, 40%, 50%, 60%, 70%, 80%, 90%, 99%, or more) indicates that the immune cell expresses a function calcitonin receptor (e.g., the subject has a calcitonin receptor-associated inflammatory or autoimmune disease or condition). Subjects diagnosed or identified as having a calcitonin receptor-associated inflammatory or autoimmune disease or condition can be treated with the methods and compositions described herein (e.g., calcitonin receptor activators). Subjects with an autoimmune or inflammatory disease or condition can also be treated with the methods and compositions described herein if an immune cell from the subject (e.g., a macrophage) is found to express a calcitonin receptor (e.g., CALCR and/or RAMP1).

The methods described herein also include methods of predicting patient response (e.g., the response of an inflammatory or autoimmune disease or condition in a subject) to calcitonin receptor activators in order to determine whether calcitonin receptor activators can be used for treatment of an inflammatory or autoimmune disease or condition. In some embodiments, a sample (e.g., an immune cell or tissue sample) is isolated from a subject and contacted with one or more calcitonin receptor activators or calcitonin receptor-specific activators (e.g., samples are cultured and contacted with one or more activators in vitro). The response of the sample (e.g., immune cell or tissue sample) to the one or more calcitonin receptor activators or calcitonin receptor-specific activators is evaluated to predict response to treatment. Responses that are evaluated include immune cell migration, proliferation, recruitment, lymph node homing, lymph node egress, differentiation, activation, polarization, cytokine production, degranulation, maturation, ADCC, ADCP, antigen presentation, or immune cell calcitonin receptor expression (e.g., expression of CALCR and/or RAMP1). A decrease of at least 5% or more (e.g., 5%, 10%, 15%, 20%, 25%, 30%, 40%, 50%, 60%, 70%, 80%, 90%, 99%, or more) in migration, proliferation, recruitment, lymph node egress, activation, pro-inflammatory cytokine production (e.g., production of IL-6 and/or IFNγ), polarization, degranulation, maturation, ADCC, ADCP, antigen presentation, calcitonin receptor expression (e.g., expression of CALCR and/or RAMP1), or markers of inflammation in treated cells compared to untreated or control-treated cells, or an increase of at least 5% or more (e.g., 5%, 10%, 15%, 20%, 25%, 30%, 40%, 50%, 60%, 70%, 80%, 90%, 99%, or more) in lymph node homing in treated cells compared to untreated or control-treated cells indicates that the inflammatory or autoimmune disease or condition would respond to treatment with a calcitonin receptor activator.

The methods used above to diagnose or identify a subject with a calcitonin receptor-associated inflammatory or autoimmune disease or condition can also be used to predict patient response (e.g., the response of an inflammatory or autoimmune disease or condition in a subject) to treatment with a calcitonin receptor activator. If the expression of a calcitonin receptor (e.g., expression of CALCR and/or RAMP1) is decreased in an immune cell sample compared to a reference (e.g., 1.1, 1.2, 1.3, 1.4, 1.5, 2.0, 2.5, 3.0, 3.5, 4.0, 4.5, 5.0, 6.0, 7.0, 8.0, 9.0, 10.0-fold or more) lower in the inflammatory or autoimmune disease or condition sample compared to the reference), the subject can be predicted to respond to treatment with a calcitonin receptor activator. Subjects predicted to respond to treatment with a calcitonin receptor activator or calcitonin receptor-specific activator can be treated using the methods and compositions described herein (e.g., calcitonin receptor activators).

Methods of Treatment

Administration

An effective amount of a calcitonin receptor activator described herein for treatment of inflammatory or autoimmune disease or condition can be administered to a subject by standard methods. For example, the agent can be administered by any of a number of different routes including, e.g., intravenous, intradermal, subcutaneous, percutaneous injection, oral, transdermal (topical), or transmucosal. The calcitonin receptor activator can be administered orally or administered by injection, e.g., intramuscularly, or intravenously. The most suitable route for administration in any given case will depend on the particular agent administered, the patient, the particular disease or condition being treated, pharmaceutical formulation methods, administration methods (e.g., administration time and administration route), the patient's age, body weight, sex, severity of the diseases being treated, the patient's diet, and the patient's excretion rate. The agent can be encapsulated or injected, e.g., in a viscous form, for delivery to a chosen site, e.g., a lymph node, lymphoid organ, gut, barrier tissue, spleen, skin, airway, wound, or site of inflammation. The agent can be provided in a matrix capable of delivering the agent to the chosen site. Matrices can provide slow release of the agent and provide proper presentation and appropriate environment for cellular infiltration. Matrices can be formed of materials presently in use for other implanted medical applications. The choice of matrix material is based on any one or more of: biocompatibility, biodegradability, mechanical properties, and cosmetic appearance and interface properties. One example is a collagen matrix.

The agent (e.g., calcitonin receptor activator, e.g., polypeptide, small molecule, nucleic acid, or antibody) can be incorporated into pharmaceutical compositions suitable for administration to a subject, e.g., a human. Such compositions typically include the agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances are known. Except insofar as any conventional media or agent is incompatible with the active compound, such media can be used in the compositions of the invention. Supplementary active compounds can also be incorporated into the compositions.

A pharmaceutical composition can be formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a calcitonin receptor activator described herein) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Systemic administration can also be by transmucosal or transdermal means. For transmucosal or transdermal administration, penetrants appropriate to the barrier to be permeated are used in the formulation. Such penetrants are generally known, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. Liposomal suspensions (including liposomes targeted to infected cells with monoclonal antibodies to viral antigens) can also be used as pharmaceutically acceptable carriers. These can be prepared according to methods known to those skilled in the art.

Nucleic acid molecule agents described herein can be administered directly (e.g., therapeutic mRNAs) or inserted into vectors used as gene therapy vectors. Gene therapy vectors can be delivered to a subject by, for example, intravenous injection, local administration (see U.S. Pat. No. 5,328,470) or by stereotactic injection (see, e.g., Chen et al., PNAS 91:3054 1994). The pharmaceutical preparation of the gene therapy vector can include the gene therapy vector in an acceptable diluent, or can include a slow release matrix in which the gene delivery vehicle is embedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of formulating pharmaceutical agents are known in the art, e.g., Niazi, Handbook of Pharmaceutical Manufacturing Formulations (Second Edition), CRC Press 2009, describes formulation development for liquid, sterile, compressed, semi-compressed and OTC forms. Transdermal and mucosal delivery, lymphatic system delivery, nanoparticles, controlled drug release systems, theranostics, protein and peptide drugs, and biologics delivery are described in Wang et al., Drug Delivery: Principles and Applications (Second Edition), Wiley 2016; formulation and delivery of peptide and protein agent is described, e.g., in Banga, Therapeutic Peptides and Proteins: Formulation, Processing, and Delivery Systems (Third Edition), CRC Press 2015.

Local Administration

The calcitonin receptor activators described herein can be administered locally, e.g., to the site of inflammatory or autoimmune disease or condition in the subject. Examples of local administration include epicutaneous, inhalational, intra-articular, intrathecal, intravaginal, intravitreal, intra-uterine, intra-lesional administration, lymph node administration, intratumoral administration and administration to a mucous membrane of the subject, wherein the administration is intended to have a local and not a systemic effect. As an example, for the treatment of an inflammatory or autoimmune disease or condition described herein, the calcitonin receptor activator may be administered locally (e.g., to or near a lymph node, lymphoid organ, spleen, barrier tissue, skin, gut, airway, or wound) in a compound-impregnated substrate such as a wafer, microcassette, or resorbable sponge placed in direct contact with the affected tissue. Alternatively, the calcitonin receptor activator is infused into the brain or cerebrospinal fluid using standard methods. As another example, for a cardiac infection, the calcitonin receptor activator may be delivered locally, for example, to the cardiac tissue (e.g., myocardium, pericardium, or endocardium) by direct intracoronary injection through the chest wall or using standard percutaneous catheter based methods. As yet another example, a chronic infection or autoimmune or inflammatory disease or condition described herein (e.g., asthma) may be treated, for example, by administering the calcitonin receptor activator locally by inhalation, e.g., in the form of an aerosol spray from a pressured container or dispenser which contains a suitable propellant, e.g., a gas such as carbon dioxide or a nebulizer. A calcitonin receptor activator for use in the methods described herein can be administered to or near a lymph node, the spleen, a secondary lymphoid organ, a tertiary lymphoid organ, barrier tissue, skin, the gut, an airway, or a wound. In certain embodiments, the agent is administered to a mucous membrane of the subject.

Combination Therapy

The calcitonin receptor activators described herein may be administered in combination with one or more additional therapies (e.g., 1, 2, 3 or more additional therapeutic agents). The two or more agents can be administered at the same time (e.g., administration of all agents occurs within 15 minutes, 10 minutes, 5 minutes, 2 minutes or less). The agents can also be administered simultaneously via co-formulation. The two or more agents can also be administered sequentially, such that the action of the two or more agents overlaps and their combined effect is such that the reduction in a symptom, or other parameter related to the disorder is greater than what would be observed with one agent or treatment delivered alone or in the absence of the other. The effect of the two or more treatments can be partially additive, wholly additive, or greater than additive (e.g., synergistic). Sequential or substantially simultaneous administration of each therapeutic agent can be effected by any appropriate route including, but not limited to, oral routes, intravenous routes, intramuscular routes, local routes, and direct absorption through mucous membrane tissues. The therapeutic agents can be administered by the same route or by different routes. For example, a first therapeutic agent of the combination may be administered by intravenous injection while a second therapeutic agent of the combination can be administered locally in a compound-impregnated microcassette. The first therapeutic agent may be administered immediately, up to 1 hour, up to 2 hours, up to 3 hours, up to 4 hours, up to 5 hours, up to 6 hours, up to 7 hours, up to, 8 hours, up to 9 hours, up to 10 hours, up to 11 hours, up to 12 hours, up to 13 hours, 14 hours, up to hours 16, up to 17 hours, up 18 hours, up to 19 hours up to 20 hours, up to 21 hours, up to 22 hours, up to 23 hours up to 24 hours or up to 1-7, 1-14, 1-21 or 1-30 days before or after the second therapeutic agent.

For use in treating inflammatory and autoimmune related diseases or conditions, the second agent may be a disease-modifying anti-rheumatic drug (DMARD), a biologic response modifier (a type of DMARD), a corticosteroid, a nonsteroidal anti-inflammatory medication (NSAID). In some embodiments, the second agent is prednisone, prednisolone, methylprednisolone, methotrexate, hydroxycholorquine, sulfasalazine, leflunomide, cyclophosphamide, azathioprine, or a biologic such as tofacitinib, adalimumab, abatacept, anakinra, kineret, certolizumab, etanercept, golimumab, infliximab, rituximab or tocilizumab. For example, if the disease is RA, the second agent may be one or more of: prednisone, prednisolone and methylprednisolone, methotrexate, hydroxycholorquine, sulfasalazine, leflunomide, cyclophosphamide and azathioprine, tofacitinib, adalimumab, abatacept, anakinra, kineret, certolizumab, etanercept, golimumab, infliximab, rituximab or tocilizumab. In some embodiments, the second agent is 6-mercaptopurine, 6-thioguanine, abatacept, adalimumab, alemtuzumab (Lemtrada), aminosalicylates (5-aminoalicylic acid, sulfasalazine, mesalamine, balsalazide, olsalazine), antibiotics, anti-histamines, anti-TNFα (infliximab, adalimumab, certolizumab pegol, natalizumab) Ustekinumab), azathioprine, belimumab, beta interferon, calcineurin inhibitors, certolizumab, corticosteroids (prednisone, methylprednisolone), cromolyn, cyclosporin A, cyclosporine, dimethyl fumarate (tecfidera), etanercept, fingolimod (Gilenya), fumaric acid esters, glatiramer acetate (Copaxone), golimumab, hydroxyurea, IFNγ, IL-11, infliximab, leflunomide, leukotriene receptor antagonist, long-acting beta2 agonist, methotrexate, mitoxantrone, mycophenolate mofetil, natalizumab (tysabri), NSAIDs, ocrelizumab, pimecrolimus, probiotics (VSL #3), retinoids, rituximab, salicylic acid, short-acting beta2 agonist, sulfasalazine, tacrolimus, teriflunomide (Aubagio), theophylline, tocilizumab, ustekinumab (anti-IL12/IL23), or vedolizumab (Anti alpha3 beta7 integrin).

For use in treating infectious disease, the second agent may be an antiviral compound (e.g., vidarabine, acyclovir, gancyclovir, valgancyclovir, nucleoside-analog reverse transcriptase inhibitor (NRTI) (e.g., AZT (Zidovudine), ddI (Didanosine), ddC (Zalcitabine), d4T (Stavudine), or 3TC (Lamivudine)), non-nucleoside reverse transcriptase inhibitor (NNRTI) (e.g., (nevirapine or delavirdine), protease inhibitor (saquinavir, ritonavir, indinavir, or nelfinavir), ribavirin, or interferon); an antibacterial compound; an antifungal compound; an antiparasitic compound.

Dosing

Subjects that can be treated as described herein are subjects with an inflammatory or autoimmune disease or condition, or subjects with an infection. The methods described herein may include a step of selecting a treatment for a patient. The method includes (a) identifying (e.g., diagnosing) a patient who has an autoimmune or inflammatory disease or condition or an infection, and (b) selecting a calcitonin receptor activator, e.g., a calcitonin receptor activator described herein, to treat the condition in the patient. In some embodiments, the method includes administering the selected treatment (e.g., an effective amount of a calcitonin receptor activator) to the subject. In some embodiments, the subject has had denervation (e.g., surgical denervation or traumatic denervation such as from spinal cord injury).

In some embodiments, the method includes administering the selected treatment to the subject.

In some embodiments, the agent is administered in an amount and for a time effective to result in one of (or more, e.g., 2 or more, 3 or more, 4 or more of): (a) reduced auto-antibody levels, (b) reduced inflammation, (c) improved organ function (d) reduced pain, (e) decreased rate or number of relapses or flare-ups of the disease, (f) increased quality of life.

The methods described herein can include profiling an immune cell to determine whether it expresses a calcitonin receptor (e.g., CALCR and/or RAMP1). Profiling can be performed using RNA sequencing, microarray analysis, or serial analysis of gene expression (SAGE). Other techniques that can be used to assess calcitonin receptor expression include quantitative RT-PCR. Profiling results can be confirmed using other methods such as immunohistochemistry, western blot analysis, flow cytometry, or southern blot analysis. Profiling results can be used to determine which calcitonin receptor activator should be administered to treat the patient.

Subjects with an inflammatory or autoimmune disease or condition or infection are treated with an effective amount of a calcitonin receptor activator. The methods described herein also include contacting immune cells with an effective amount of a calcitonin receptor activator. In some embodiments, an effective amount of a calcitonin receptor activator is an amount sufficient to increase or decrease lymph node innervation, nerve firing in a lymph node, the development of HEVs or TLOs, immune cell migration, proliferation, recruitment, lymph node homing, lymph node egress, differentiation, activation, polarization, cytokine production, degranulation, maturation, ADCC, ADCP, or antigen presentation. In some embodiments, an effective amount of a calcitonin receptor activator is an amount sufficient to treat the autoimmune or inflammatory condition or infection, reduce symptoms of an autoimmune or inflammatory condition, reduce inflammation, reduce auto-antibody levels, improve organ function, decrease rate or number of relapses or flare-ups, reduce viral load, or control infection.

In some embodiments, a calcitonin receptor activator administered according to the methods described herein does not have a direct effect on the central nervous system (CNS) or gut. Any effect on the CNS or gut is reduced compared to the effect observed if the calcitonin receptor activator is administered directly to the CNS or gut. In some embodiments, direct effects on the CNS or gut are avoided by modifying the calcitonin receptor activator not to cross the BBB, as described herein above, or administering the agent locally to a subject.

The methods described herein may also include a step of assessing the subject for a parameter of immune response, e.g., assessing the subject for one or more (e.g., 2 or more, 3 or more, 4 or more) of: Tregs, Th2 cells, T cells, circulating monocytes, neutrophils, peripheral blood hematopoietic stem cells, macrophages, mast cell degranulation, activated B cells, NKT cells, macrophage phagocytosis, macrophage polarization, antigen presentation, immune cell activation, immune cell proliferation, immune cell lymph node homing or egress, T cell differentiation, immune cell recruitment, immune cell migration, lymph node innervation, dendritic cell maturation, HEV development, TLO development, or cytokine production. In embodiments, the method includes measuring a cytokine or marker associated with the particular immune cell type, as listed in Table 1 (e.g., performing an assay listed in Table 1 for the cytokine or marker). In some embodiments, the method includes measuring a chemokine, receptor, or immune cell trafficking molecule, as listed in Tables 2 and 3 (e.g., performing an assay to measure the chemokine, marker, or receptor). The assessing may be performed after the administration, before the first administration and/or during a course a treatment, e.g., after a first, second, third, fourth or later administration, or periodically over a course of treatment, e.g., once a month, or once every 3 months. In one embodiment, the method includes assessing the subject prior to treatment or first administration and using the results of the assessment to select a subject for treatment. In certain embodiments, the method also includes modifying the administering step (e.g., stopping the administration, increasing or decreasing the periodicity of administration, increasing or decreasing the dose of the calcitonin receptor activator) based on the results of the assessment. For example, in embodiments where increasing a parameter of immune response described herein is desired (e.g., in inflammatory or autoimmune disease-related embodiments where, e.g., an increase in Treg cells is desired), the method includes stopping the administration if a marker of Treg cells is not increased at least 5%, 10%, 15%, 20%, 30%, 40%, 50% or more; or the method includes increasing the periodicity of administration if the marker of Treg cells is not increased at least 5%, 10%, 15%, 20%, 30%, 40%, 50% or more; or the method includes increasing the dose of the calcitonin receptor activator if the marker of Treg cells is not increased at least 5%, 10%, 15%, 20%, 30%, 40%, 50% or more. For example, in embodiments where decreasing a parameter of immune response described herein is desired (e.g., embodiments where a decrease in macrophage cells is desired), the method includes stopping the administration if a marker of macrophage cells is not decreased at least 5%, 10%, 15%, 20%, 30%, 40%, 50% or more; or the method includes increasing the periodicity of administration if the marker of macrophage cells is not decreased at least 5%, 10%, 15%, 20% or more; or the method includes increasing the dose of the calcitonin receptor activator if the marker of macrophage cells is not decreased at least 5%, 10%, 15%, 20% or more.

In certain embodiments, immune effects (e.g., immune cell activities) are modulated in a subject (e.g., a subject having an inflammatory or autoimmune condition) or in a cultured cell by at least 1%, 2%, 5%, 10%, 15%, 20%, 25%, 30%, 35%, 40%, 50%, 60%, 70%, 80%, compared to before an administration, e.g., of a dosing regimen, of a calcitonin receptor activator such as those described herein. In certain embodiments, the immune effects are modulated in the subject or a cultured cell between 5-20%, between 5-50%, between 10-50%, between 20-80%, between 20-70%, between 50-100%, between 100-500%. The immune effects described herein may be assessed by standard methods:

The calcitonin receptor activators described herein are administered in an amount (e.g., an effective amount) and for a time sufficient to effect one of the outcomes described above. The calcitonin receptor activator may be administered once or more than once. The calcitonin receptor activator may be administered once daily, twice daily, three times daily, once every two days, once weekly, twice weekly, three times weekly, once biweekly, once monthly, once bimonthly, twice a year, or once yearly. Treatment may be discrete (e.g., an injection) or continuous (e.g., treatment via an implant or infusion pump). Subjects may be evaluated for treatment efficacy 1 week, 2 weeks, 1 month, 2 months, 3 months, 4 months, 5 months, 6 months or more following administration of a calcitonin receptor activator depending on the calcitonin receptor activator and route of administration used for treatment. Depending on the outcome of the evaluation, treatment may be continued or ceased, treatment frequency or dosage may change, or the patient may be treated with a different calcitonin receptor activator. Subjects may be treated for a discrete period of time (e.g., 1, 2, 3, 4, 5, 6, 7, 8, 9, 10, 11, or 12 months) or until the disease or condition is alleviated, or treatment may be chronic depending on the severity and nature of the disease or condition being treated.

Kits

The invention also features a kit including (a) a pharmaceutical composition including a calcitonin receptor activator described herein, and (b) instructions for administering the pharmaceutical composition to treat an inflammatory or autoimmune disease or condition.

In some embodiments, the kit includes (a) a unit dose of a calcitonin receptor activator that increases an immune response described herein, (b) a vaccine against an infectious agent, and (c) instructions for administering the unit dose to prevent or treat an infection caused by the infectious agent.

EXAMPLES

The following examples are provided to further illustrate some embodiments of the present invention, but are not intended to limit the scope of the invention; it will be understood by their exemplary nature that other procedures, methodologies, or techniques known to those skilled in the art may alternatively be used.

Example 1—Identification of Calcitonin Receptors on Immune Cells

CD14+ monocytes were isolated from human PBMCs using negative magnetic bead selection (Stemcell Technologies) on day 0. Cells were cultured two days with M-CSF to differentiate monocytes to macrophages. On day 3, macrophages were polarized to M1-like macrophages with IFNγ and LPS; and M2-like macrophages with IL4, IL10, and TGFβ. Cells were harvested on day 6. The cells were lysed and RNA was extracted using an RNA extraction kit (Qiagen). qPCR was performed using integrated fluidic circuits (IFCs) run on a real-time PCR machine (Fluidigm) with primers specific for CALCR and RAMP1 (Life Technologies). Gene expression was normalized to HPRT1. Expression level was calculated by 2^(−delta CT), where delta CT is (GOI Ct—HPRT Ct).

Gene expression for CALCR in M2-like macrophages and RAMP1 in both M1-like and M2-like macrophages was determined. RAMP1 expression was higher in M2-like macrophages compared to M1-like macrophages, as shown in Table 12 below.

TABLE 12

EXPRESSION OF CALCITONIN RECEPTORS IN MACROPHAGES

| Cell Type | Gene Name | Expression Level (Relative to HPRT1) |
|---|---|---|
| M1-like Macrophages | CALCR (Entrez: 799) | Not detected |
| M2-like Macrophages | CALCR (Entrez: 799) | 0.0304 |
| M1-like Macrophages | RAMP1 (Entrez: 10267) | 0.01045 |
| M2-like Macrophages | RAMP1 (Entrez: 10267) | 5.7757 |

Example 2—Modulation of Calcitonin Receptors with a Small Molecule Agonist

CD14+ monocytes were isolated from human PBMCs using negative magnetic bead selection (Stemcell Technologies) on day 0. Cells were cultured with M-CSF to differentiate monocytes to macrophages. On day 6, cells were treated with SUN-B-8155, a non-peptide calcitonin receptor agonist (Sigma-Aldrich), at concentrations 2 µM and 20 µM overnight. Supernatant was collected and bead-based immunoassays (Biolegend) were performed to detect changes in cytokine secretion.

Across multiple donors, secretion of the inflammatory cytokine, IL6, by macrophages was decreased after addition of small molecule agonist to calcitonin receptor, as shown in Table 13 below.

TABLE 13

EFFECT OF CALCITONIN RECEPTOR AGONISM ON CYTOKINE SECRETION IN HUMAN MACROPHAGES

| Sample | Fold change of IL6(Normalized to Macs + LPS with no compound treatment) |
|---|---|
| Macs + LPS | 1.00 |
| Macs + LPS + SUN-B-8155 (2 µM) | 0.92 |
| Macs + LPS + SUN-B-8155 (20 µM) | 0.09 |

Example 3—Administration of a Calcitonin Receptor Activator to Treat Local Intestinal Inflammation According to the methods disclosed herein, a physician of skill in the art can treat a patient, such as a human patient with an inflammatory condition (e.g., intestinal inflammation, such as IBD, ulcerative colitis (UC), or Hirschsprung's disease-associated enterocolitis (HAEC)), so as to reduce the inflammation that contributes to the condition. Before treating the patient, a physician can perform an endoscopy or colonoscopy to diagnose a patient with intestinal inflammation, or identify a patient as having intestinal inflammation based on results from an endoscopy or colonoscopy. To treat the patient, a physician of skill in the art can administer to the human patient a calcitonin receptor activator that decreases macrophage activation (e.g., an agent that increases calcitonin receptor signaling, such as calcitonin receptor-specific activating antibodies). The calcitonin receptor-specific activating antibody can be and administered parenterally (e.g., by subcutaneous injection or intravenous infusion) to treat intestinal inflammation. The calcitonin receptor-specific activating antibody is administered in a therapeutically effective amount, such as from 10 µg/kg to 500 mg/kg (e.g., 10 µg/kg, 100 µg/kg, 500 µg/kg, 1 mg/kg, 10 mg/kg, 50 mg/kg, 100 mg/kg, 250 mg/kg, or 500 mg/kg). In some embodiments, the calcitonin receptor-specific activating antibody is administered bimonthly, once a month, once every two weeks, or at least once a week or more (e.g., 1, 2, 3, 4, 5, 6, or 7 times a week or more).

The calcitonin receptor-specific activating antibody decreases macrophage production of one or more pro-inflammatory cytokines (e.g., IL6 or IFNγ). The calcitonin receptor-specific activating antibody is administered to the patient in an amount sufficient to decrease pro-inflammatory cytokine levels by 10% or more (e.g., 10%, 20%, 30%, 40%, 50%, 60%, 70%, 80%, 90%, 95% or more), or improve symptoms of intestinal inflammation (e.g., abdominal pain, diarrhea, fever, and fatigue). Cytokine production can be assessed by collecting a blood sample from the patient and evaluating one or more pro-inflammatory cytokines (e.g., IL6 or IFNγ). The blood sample can be collected one day or more after administration of the calcitonin receptor-specific activating antibody (e.g., 1, 2, 3, 4, 5, 6, 7, 10, 14, 21, or 30 or more days after administration). The blood sample can be compared to a blood sample collected from the patient prior to administration of the calcitonin receptor-specific activating antibody (e.g., a blood sample collected earlier the same day, 1 day, 1 week, 2 weeks, one month or more before administration of the calcitonin receptor-specific activating antibody). A restoration in intestinal health as evaluated using a colonoscopy, endoscopy or tissue biopsy, reduction in the symptoms of intestinal inflammation (e.g., abdominal pain, diarrhea, fever, and fatigue), a reduction in the markers of intestinal inflammation in a blood sample (e.g., CRP, ESR, calprotectin, or lactoferrin, as compared to levels in a blood sample before treatment), reduced pro-inflammatory cytokine levels, or increased IL-10, TGFβ, Arg1, IDO, PF4, CCL24, or IL4Ralpha indicate that the calcitonin receptor-specific activating antibody reduces inflammation, reduces macrophage activation, or treats intestinal inflammation.

Other Embodiments

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims. Other embodiments are within the claims.

What is claimed is:

1. A method comprising administering to a subject in need thereof a small molecule calcitonin receptor agonist in an amount effective to reduce interleukin-6 (IL-6) secretion by macrophages, wherein IL-6 is elevated in the human subject, relative to a control.

2. The method of claim 1, wherein the small molecule calcitonin receptor agonist is a non-peptide calcitonin receptor agonist.

3. The method of claim 2, wherein the non-peptide calcitonin receptor agonist is SUN-B-8155.

4. The method of claim 1, wherein the subject has ulcerative colitis.

5. The method of claim 1, wherein the subject has Crohn's disease.

6. The method of claim 1, wherein the subject has inflammatory bowel disease.

7. The method of claim 1, wherein the small molecule calcitonin receptor agonist is administered to the subject in amount effective to reduce IL-6 secretion by macrophages by at least 10%, relative to a control.

8. The method of claim 1, wherein the small molecule calcitonin receptor agonist is administered to the subject via a route selected from intravenous, intradermal, subcutaneous, percutaneous injection, oral, transdermal, and transmucosal.

9. A method comprising administering to a subject in need thereof a non-peptide calcitonin receptor agonist in an amount effective to reduce interleukin-6 (IL-6) secretion by macrophages, wherein IL-6 is elevated in the human subject, relative to a control, the subject has inflammatory bowel disease, Crohn's disease, or ulcerative colitis, and the non-peptide calcitonin receptor agonist is administered locally.

10. A method comprising culturing human macrophages with a calcitonin receptor agonist and measuring IL-6 secreted by the human macrophages.

* * * * *